US012651286B2

(12) United States Patent
Simpson

(10) Patent No.: US 12,651,286 B2
(45) Date of Patent: Jun. 9, 2026

(54) SYSTEM AND METHOD FOR DETERMINING OPTIMIZED FOOD COMBINATIONS

(71) Applicant: CirclesX LLC, Houston, TX (US)

(72) Inventor: Erik M Simpson, Houston, TX (US)

(73) Assignee: CIRCLESX LLC, Houston, TX (US)

( * ) Notice: Subject to any disclaimer, the term of this patent is extended or adjusted under 35 U.S.C. 154(b) by 1506 days.

(21) Appl. No.: 16/380,771

(22) Filed: Apr. 10, 2019

(65) Prior Publication Data

US 2019/0304000 A1 Oct. 3, 2019

Related U.S. Application Data

(63) Continuation-in-part of application No. 15/484,059, filed on Apr. 10, 2017, now Pat. No. 12,039,585.

(51) Int. Cl.

| | |
|---|---|
| ***G06Q 30/0601*** | (2023.01) |
| ***G01N 33/487*** | (2006.01) |
| ***G01N 33/49*** | (2006.01) |
| ***G06N 3/042*** | (2023.01) |
| ***G06N 3/08*** | (2023.01) |
| ***G16B 40/00*** | (2019.01) |
| ***G16H 20/60*** | (2018.01) |

(52) U.S. Cl.

CPC ... *G06Q 30/0631* (2013.01); *G01N 33/48792* (2013.01); *G01N 33/492* (2013.01); *G06N 3/042* (2023.01); *G06N 3/08* (2013.01); *G06Q 30/0633* (2013.01); *G16B 40/00* (2019.02); *G16H 20/60* (2018.01)

(58) Field of Classification Search

None

See application file for complete search history.

(56) References Cited

U.S. PATENT DOCUMENTS

| | | | | |
|---|---|---|---|---|
| D209,710 | S | 12/1967 | Bruce | |
| 4,476,954 | A | 10/1984 | Johnson et al. | |
| D318,073 | S | 7/1991 | Jang | |
| 5,249,259 | A * | 9/1993 | Harvey | G06N 3/126 706/13 |
| 5,412,560 | A | 5/1995 | Dennison | |
| 5,604,676 | A | 2/1997 | Penzias | |
| 5,726,885 | A | 3/1998 | Klein et al. | |
| 5,751,245 | A | 5/1998 | Janky et al. | |
| 5,948,040 | A | 9/1999 | DeLorme | |
| 5,973,619 | A | 10/1999 | Paredes | |
| 6,175,831 | B1 | 1/2001 | Weinreich et al. | |
| 6,240,396 | B1 | 5/2001 | Walker et al. | |
| 6,285,999 | B1 | 9/2001 | Page | |
| D453,945 | S | 2/2002 | Shan | |
| 6,356,838 | B1 | 3/2002 | Paul | |
| 6,400,996 | B1 | 6/2002 | Hoffberg | |
| D460,952 | S | 7/2002 | Kataoka | |
| 6,421,606 | B1 | 7/2002 | Asai et al. | |
| 6,434,530 | B1 | 8/2002 | Sloane et al. | |
| D468,738 | S | 1/2003 | Lin | |
| D469,089 | S | 1/2003 | Lin | |
| 6,609,103 | B1 | 8/2003 | Kolls | |
| 6,618,062 | B1 | 9/2003 | Brown et al. | |
| 6,646,659 | B1 | 11/2003 | Brown et al. | |
| 6,663,564 | B2 | 12/2003 | Miller-Kovach et al. | |
| 6,708,879 | B2 | 3/2004 | Hunt | |
| 6,850,907 | B2 | 2/2005 | Lutnick et al. | |
| 7,010,472 | B1 | 3/2006 | Vasey-Glandon et al. | |
| 7,090,638 | B2 | 8/2006 | Vidgen | |
| 7,373,320 | B1 | 5/2008 | Mcdonough | |
| D590,396 | S | 4/2009 | Lo | |
| 7,584,123 | B1 | 9/2009 | Karonis et al. | |
| 7,634,442 | B2 | 12/2009 | Alvarado et al. | |
| 7,680,690 | B1 | 3/2010 | Catalano | |
| 7,680,770 | B1 | 3/2010 | Buyukkokten et al. | |
| 7,711,629 | B2 | 5/2010 | Laurent et al. | |

(Continued)

FOREIGN PATENT DOCUMENTS

| | | | |
|---|---|---|---|
| CN | 107341968 | A | 11/2017 |
| GB | 2539556 | A | 12/2016 |

(Continued)

OTHER PUBLICATIONS

Sauelle et al. (Nutrients (2013) vol. 5:4566-4586).*

PCT International Search Report and Written Opinion; PCT/US2020/027543; Jul. 1, 2020.

PCT International Search Report and Written Opinion; PCT/US2020/023223; Jun. 19, 2020.

PCT International Search Report and Written Opinion; PCT/US2020/023729; Jun. 18, 2020.

PCT International Search Report and Written Opinion; PCT/US2020/021546; Jun. 8, 2020.

PCT International Search Report and Written Opinion; PCT/US2020/018012; Apr. 21, 2020.

(Continued)

*Primary Examiner* — Lori A. Clow

(74) *Attorney, Agent, or Firm* — Pramudji Law Group PLLC; Ari Pramudji

(57) ABSTRACT

A computer implemented method for use in conjunction with a computing device, system, network, and cloud with touch screen two dimension display or augmented/mixed reality three dimension display comprising: obtaining, analyzing and detecting user blood, saliva, hair, urine, stool, fingernail, height, weight and skin sampling analysis chemistry data, mapping the blood, saliva, hair, urine, stool, fingernail, height, weight and skin data into a database associated with a specific user, applying the data with optimization equations, mapping equations to food and beverage chemistry, scoring or ranking a plurality of optimized results such that a user may order food and beverage from a food/beverage distribution point or have food/beverage delivered to the user which has been specifically optimized for their specific biochemistry characteristic target ranges. The method is particularly useful in enhancing online internet search engine results.

20 Claims, 50 Drawing Sheets

(56) References Cited

U.S. PATENT DOCUMENTS 7,747,739 B2 6/2010 Bridges et al.
7,756,633 B2 7/2010 Huang et al.
7,788,207 B2 8/2010 Alcorn et al.
D628,171 S 11/2010 Hakopian
7,886,166 B2 2/2011 Shnekendorf et al.
D638,879 S 5/2011 Suto
7,987,110 B2 7/2011 Cases et al.
8,024,234 B1 9/2011 Thomas et al.
8,065,191 B2 11/2011 Senior
D650,385 S 12/2011 Chiu
8,121,780 B2 2/2012 Gerdes et al.
8,249,946 B2 8/2012 Froseth et al.
8,296,335 B2 10/2012 Bouve et al.
8,388,451 B2 3/2013 Auterio et al.
8,570,244 B2 10/2013 Mukawa
8,762,035 B2 6/2014 Levine et al.
8,798,593 B2 8/2014 Haney
8,918,411 B1 12/2014 Latif et al.
8,920,175 B2 12/2014 Black et al.
8,930,490 B2 1/2015 Brown et al.
8,968,099 B1 3/2015 Hanke et al.
9,011,153 B2 4/2015 Bennett et al.
9,020,763 B2 4/2015 Faaborg et al.
9,077,204 B2 7/2015 More et al.
9,092,826 B2 7/2015 Deng et al.
9,159,088 B2 10/2015 Dillahunt et al.
9,213,957 B2 12/2015 Stefik et al.
9,274,540 B2 3/2016 Anglin et al.
9,292,764 B2 3/2016 Yun et al.
9,387,928 B1 7/2016 Gentry et al.
9,389,090 B1 7/2016 Levine et al.
9,389,094 B2 7/2016 Brenner et al.
9,410,963 B2 8/2016 Martin et al.
9,436,923 B1 9/2016 Sriram et al.
9,450,817 B1 9/2016 Bahadur et al.
D772,828 S 11/2016 Kusumoto
9,528,972 B2 12/2016 Minvielle
9,558,515 B2 1/2017 Babu et al.
9,665,983 B2 5/2017 Spivack
9,880,577 B2 1/2018 Dyess et al.
9,952,042 B2 4/2018 Abovitz et al.
9,960,637 B2 5/2018 Sanders et al.
9,978,282 B2 5/2018 Lambert et al.
10,082,793 B1 9/2018 Glaser
D832,355 S 10/2018 Castro
10,216,367 B1 2/2019 Patel
10,262,289 B2 4/2019 Vaananen
10,395,332 B1 8/2019 Konrardy et al.
10,403,050 B1 9/2019 Beall et al.
10,408,489 B1 9/2019 Trishaun et al.
10,452,978 B2 10/2019 Shazeer et al.
10,460,520 B2 10/2019 Simpson et al.
10,533,850 B2 1/2020 Abovitz et al.
10,586,084 B2 3/2020 Burch et al.
10,642,887 B2 5/2020 Chen et al.
10,685,503 B2 6/2020 Ricci
10,719,764 B2 7/2020 Shazeer et al.
10,737,585 B2 8/2020 Chaudhary et al.
D896,315 S 9/2020 Castro
10,832,337 B1 11/2020 Floyd et al.
D903,657 S 12/2020 Catania
D903,658 S 12/2020 Catania
D903,659 S 12/2020 Catania
10,872,381 B1 12/2020 Leise et al.
D910,758 S 2/2021 Leong
10,956,819 B2 3/2021 Shazeer et al.
11,035,682 B2 6/2021 Simpson
11,113,602 B2 9/2021 Shazeer et al.
11,138,661 B2 10/2021 Simpson
11,138,827 B2 10/2021 Simpson
11,157,852 B2 10/2021 Simpson
11,183,080 B2 * 11/2021 Wolf ...................... G16H 50/70
D938,375 S 12/2021 Zhang
11,215,466 B2 1/2022 Simpson
11,288,563 B2 3/2022 Lee et al.
11,296,897 B2 4/2022 Endress et al.
11,298,017 B2 4/2022 Tran
11,298,591 B2 4/2022 Evancha
11,398,299 B2 7/2022 Chen et al.
11,410,756 B2 8/2022 Oren et al.
11,537,953 B2 12/2022 Beaurepaire
11,555,709 B2 1/2023 Simpson
11,586,993 B2 2/2023 Handler et al.
D980,210 S 3/2023 Wu
11,651,464 B2 5/2023 Park
D993,316 S 7/2023 Lin
11,704,219 B1 7/2023 Lerner et al.
11,722,500 B2 8/2023 Singh
11,734,618 B2 8/2023 Ogden
D1,000,137 S 10/2023 Shuster
D1,007,451 S 12/2023 Im
11,893,483 B2 2/2024 Shazeer et al.
11,935,634 B2 3/2024 Mossin et al.
D1,024,065 S 4/2024 Kim
12,001,999 B2 6/2024 Simpson
12,217,173 B2 2/2025 Shazeer et al.
2002/0004788 A1 1/2002 Gros et al.
2002/0013718 A1 1/2002 Cornwell
2002/0013761 A1 1/2002 Bundy
2002/0017997 A1 2/2002 Wall
2002/0065738 A1 5/2002 Riggs et al.
2002/0065766 A1 5/2002 Brown et al.
2002/0128952 A1 9/2002 Melkomaian
2002/0133456 A1 9/2002 Lancaster et al.
2002/0161689 A1 10/2002 Segal
2003/0055776 A1 3/2003 Samuelson
2003/0191725 A1 10/2003 Ratliff et al.
2003/0233311 A1 12/2003 Bramnick et al.
2004/0019552 A1 1/2004 Tobin
2004/0115596 A1 6/2004 Snyder et al.
2004/0249742 A1 12/2004 Laurent et al.
2004/0254819 A1 12/2004 Halim
2004/0260581 A1 12/2004 Baranowski et al.
2005/0021346 A1 1/2005 Nadan et al.
2005/0027637 A1 2/2005 Kohler
2005/0132070 A1 6/2005 Redlich et al.
2005/0288974 A1 12/2005 Baranowski et al.
2005/0288986 A1 12/2005 Barts et al.
2006/0104224 A1 5/2006 Singh
2006/0184321 A1 8/2006 Kawakami
2007/0005224 A1 1/2007 Sutardja
2007/0260723 A1 11/2007 Cohen
2008/0033833 A1 2/2008 Senior
2008/0040232 A1 2/2008 Perchthaler
2008/0077309 A1 3/2008 Cobbold
2008/0129490 A1 6/2008 Linville et al.
2008/0140557 A1 6/2008 Bowlby et al.
2008/0157990 A1 7/2008 Belzer et al.
2008/0195428 A1 8/2008 O'Sullivan
2008/0195432 A1 8/2008 Fell et al.
2008/0262892 A1 10/2008 Prager et al.
2009/0221338 A1 9/2009 Stewart
2009/0231687 A1 9/2009 Yamamoto
2009/0271236 A1 10/2009 Ye et al.
2009/0275002 A1 11/2009 Hoggle
2009/0276154 A1 11/2009 Subramanian et al.
2009/0287401 A1 11/2009 Levine et al.
2009/0309729 A1 12/2009 Nichols
2010/0042421 A1 2/2010 Bai et al.
2010/0042453 A1 2/2010 Scaramellino et al.
2010/0081548 A1 4/2010 Labedz
2010/0114790 A1 5/2010 Strimling et al.
2010/0191834 A1 7/2010 Zampiello
2010/0208029 A1 8/2010 Marti
2010/0211441 A1 8/2010 Sprigg et al.
2010/0217680 A1 8/2010 Fusz et al.
2010/0228574 A1 9/2010 Mundinger et al.
2010/0280748 A1 11/2010 Mundinger et al.
2010/0280884 A1 11/2010 Levine et al.
2010/0306078 A1 12/2010 Hwang
2010/0318373 A1 12/2010 Harris
2011/0025267 A1 2/2011 Kamen et al.
2011/0059693 A1 3/2011 O'Sullivan
2011/0098056 A1 4/2011 Rhoads et al.

(56) References Cited

U.S. PATENT DOCUMENTS

2011/0106660 A1 5/2011 Ajjarapu et al.
2011/0184784 A1 7/2011 Rudow
2011/0191248 A1 8/2011 Bishop
2011/0202418 A1 8/2011 Kempton et al.
2012/0023032 A1 1/2012 Visdomini
2012/0072925 A1 3/2012 Jenkins et al.
2012/0075067 A1 3/2012 Attaluri
2012/0078743 A1 3/2012 Betancourt
2012/0101629 A1 4/2012 Olsen et al.
2012/0130556 A1 5/2012 Marhoefer
2012/0136527 A1 5/2012 McQuade
2012/0158762 A1 6/2012 IwuchukWu
2012/0303259 A1 11/2012 Prosser
2012/0323645 A1 12/2012 Spiegel et al.
2013/0024041 A1 1/2013 Golden et al.
2013/0035973 A1 2/2013 Desai et al.
2013/0132261 A1 5/2013 Ebersole
2013/0147820 A1 6/2013 Kalai et al.
2013/0173326 A1 7/2013 Anglin et al.
2013/0179205 A1 7/2013 Slinin
2013/0191237 A1 7/2013 Tenorio
2013/0211863 A1 8/2013 White
2013/0265174 A1 10/2013 Scofield et al.
2013/0268325 A1 10/2013 Dembo
2013/0275156 A1 10/2013 Kinkaid et al.
2013/0304522 A1 11/2013 Cundle
2013/0311264 A1 11/2013 Solomon et al.
2014/0032034 A1 1/2014 Raptopoulos
2014/0038781 A1 2/2014 Foley
2014/0052500 A1 2/2014 Vallapuzha et al.
2014/0075528 A1 3/2014 Matsuoka
2014/0098009 A1 4/2014 Prest et al.
2014/0122190 A1 5/2014 Wolfson et al.
2014/0129302 A1 5/2014 Amin et al.
2014/0149157 A1 5/2014 Shaam et al.
2014/0162598 A1 6/2014 Villa-Real
2014/0180732 A1 6/2014 Rotchin
2014/0220516 A1 8/2014 Marshall et al.
2014/0229258 A1 8/2014 Seriani
2014/0236641 A1 8/2014 Dawkins
2014/0244413 A1 8/2014 Senior
2014/0282586 A1 9/2014 Shear et al.
2014/0310019 A1 10/2014 Blander et al.
2014/0310149 A1 10/2014 Singh
2014/0324633 A1 10/2014 Pollak et al.
2014/0349672 A1 11/2014 Kern et al.
2014/0358431 A1 12/2014 Isert
2015/0006428 A1 1/2015 Miller et al.
2015/0016777 A1 1/2015 Abovitz et al.
2015/0058051 A1 2/2015 Movshovich
2015/0097864 A1 4/2015 Alaniz
2015/0154516 A1 6/2015 Joachim
2015/0161564 A1 6/2015 Sweeney et al.
2015/0178642 A1 6/2015 Abboud
2015/0198459 A1 7/2015 MacNeille et al.
2015/0206443 A1 7/2015 Aylesworth et al.
2015/0220916 A1 8/2015 Prakash et al.
2015/0241236 A1 8/2015 Slusar et al.
2015/0248689 A1 9/2015 Paul et al.
2015/0260474 A1 9/2015 Rublowsky et al.
2015/0269865 A1 9/2015 Volach et al.
2015/0324831 A1 11/2015 Barua et al.
2015/0348282 A1 12/2015 Gibbon et al.
2015/0371186 A1 12/2015 Podgurny et al.
2016/0018969 A1 1/2016 Sundarraman
2016/0026253 A1 1/2016 Bradski et al.
2016/0034305 A1 2/2016 Shear et al.
2016/0041628 A1 2/2016 Verma
2016/0063436 A1 3/2016 Coles
2016/0117657 A1 4/2016 Forbes, Jr. et al.
2016/0117756 A1 4/2016 Carr et al.
2016/0148289 A1 5/2016 Altschuler
2016/0162989 A1 6/2016 Cole et al.
2016/0171891 A1 6/2016 Banatwala et al.
2016/0203422 A1 7/2016 Demarchi et al.
2016/0221935 A1 8/2016 Jaworska-Maslanka
2016/0224935 A1 8/2016 Burnett
2016/0225115 A1 8/2016 Levy et al.
2016/0253662 A1 9/2016 Sriram
2016/0297316 A1 10/2016 Penilla et al.
2016/0298977 A1 10/2016 Newlin
2016/0300296 A1 10/2016 Alonso Cembrano
2016/0307276 A1 10/2016 Young
2016/0307288 A1 10/2016 Yehuda et al.
2016/0307373 A1 10/2016 Dean et al.
2016/0321609 A1 11/2016 Dube et al.
2016/0349835 A1 12/2016 Shapira
2016/0364679 A1 12/2016 Cao
2017/0019496 A1 1/2017 Orbach
2017/0039770 A1 2/2017 Lanier et al.
2017/0046658 A1 2/2017 Jones et al.
2017/0046664 A1 2/2017 Haldenby et al.
2017/0046799 A1 2/2017 Chan et al.
2017/0046806 A1 2/2017 Haldenby et al.
2017/0048216 A1 2/2017 Chow et al.
2017/0053461 A1 2/2017 Pal et al.
2017/0061509 A1 3/2017 Rosenberg et al.
2017/0089710 A1 3/2017 Slusar
2017/0122746 A1 5/2017 Howard et al.
2017/0146360 A1 5/2017 Averbuch
2017/0232300 A1 8/2017 Tran et al.
2017/0243286 A1 8/2017 Castinado et al.
2017/0243310 A1 8/2017 Dawkins
2017/0249626 A1 8/2017 Marlatt
2017/0276500 A1 9/2017 Margalit et al.
2017/0293881 A1 10/2017 Narkulla
2017/0293950 A1 10/2017 Rathod
2017/0318325 A1 11/2017 Ortiz
2017/0330274 A1 11/2017 Conant, II et al.
2017/0356749 A1 12/2017 Shelby
2017/0357914 A1 12/2017 Tulabandhula
2017/0373509 A1 12/2017 Betzin
2018/0012149 A1 1/2018 Yust
2018/0013211 A1 1/2018 Ricci
2018/0025417 A1 1/2018 Brathwaite et al.
2018/0046431 A1 2/2018 Thagadur Shivappa et al.
2018/0053226 A1 2/2018 Hutton et al.
2018/0053237 A1 2/2018 Hayes et al.
2018/0068355 A1 3/2018 Garry
2018/0075695 A1 3/2018 Simpson
2018/0088455 A1 3/2018 Cippant
2018/0095471 A1 4/2018 Allan et al.
2018/0102053 A1 4/2018 Hillman et al.
2018/0111494 A1 4/2018 Penilla et al.
2018/0117447 A1 5/2018 Bao et al.
2018/0121958 A1 5/2018 Aist et al.
2018/0129276 A1 5/2018 Nguyen et al.
2018/0140903 A1 5/2018 Poure
2018/0143029 A1 5/2018 Nikulin et al.
2018/0157999 A1 6/2018 Arora
2018/0165354 A1 6/2018 Mehta et al.
2018/0165364 A1 6/2018 Mehta et al.
2018/0173742 A1 6/2018 Liu et al.
2018/0173800 A1 6/2018 Chang et al.
2018/0188715 A1 7/2018 Cella et al.
2018/0190026 A1 7/2018 Barnett et al.
2018/0209801 A1 7/2018 Stentz
2018/0209803 A1 7/2018 Rakah
2018/0238705 A1 8/2018 O'Herlihy
2018/0240542 A1* 8/2018 Grimmer ................ A61P 25/00
2018/0278984 A1 9/2018 Aimone et al.
2018/0293638 A1 10/2018 Simpson
2018/0313798 A1 11/2018 Chokshi et al.
2018/0342106 A1 11/2018 Rosado
2018/0348863 A1 12/2018 Aimone et al.
2018/0357899 A1 12/2018 Krivacic et al.
2018/0365598 A1 12/2018 Jamail
2018/0365904 A1 12/2018 Holmes
2018/0374268 A1 12/2018 Niles
2019/0019144 A1 1/2019 Gillen
2019/0020973 A1 1/2019 Harish
2019/0047427 A1 2/2019 Pogorelik
2019/0050634 A1 2/2019 Nerayoff et al.
2019/0066528 A1 2/2019 Hwang et al.

(56) References Cited

U.S. PATENT DOCUMENTS

| | | | |
|---|---|---|---|
| 2019/0102946 | A1 | 4/2019 | Spivack et al. |
| 2019/0108686 | A1 | 4/2019 | Spivack et al. |
| 2019/0139448 | A1 | 5/2019 | Marshall et al. |
| 2019/0143828 | A1 | 5/2019 | Sawada et al. |
| 2019/0146974 | A1 | 5/2019 | Chung et al. |
| 2019/0158603 | A1 | 5/2019 | Nelson et al. |
| 2019/0160958 | A1 | 5/2019 | Chaudhary et al. |
| 2019/0178654 | A1 | 6/2019 | Hare |
| 2019/0180862 | A1 | 6/2019 | Wisser et al. |
| 2019/0186942 | A1 | 6/2019 | Rubin |
| 2019/0188450 | A1 | 6/2019 | Spivack et al. |
| 2019/0202448 | A1 | 7/2019 | Pal et al. |
| 2019/0204110 | A1 | 7/2019 | Dubielzyk |
| 2019/0205798 | A1 | 7/2019 | Rosas-Maxemin et al. |
| 2019/0228269 | A1 | 7/2019 | Brent et al. |
| 2019/0236741 | A1 | 8/2019 | Bowman et al. |
| 2019/0236742 | A1 | 8/2019 | Tomskii et al. |
| 2019/0251503 | A1 | 8/2019 | Simpson |
| 2019/0251509 | A1 | 8/2019 | Simpson |
| 2019/0259008 | A1 | 8/2019 | Lindsey |
| 2019/0271553 | A1 | 9/2019 | Simpson |
| 2019/0272589 | A1 | 9/2019 | Simpson |
| 2019/0293438 | A1 | 9/2019 | Simpson |
| 2019/0304000 | A1 | 10/2019 | Simpson |
| 2019/0311431 | A1 | 10/2019 | Simpson |
| 2019/0318286 | A1 | 10/2019 | Simpson |
| 2019/0324989 | A1 | 10/2019 | Borochoff et al. |
| 2019/0325541 | A1 | 10/2019 | Simpson |
| 2019/0333166 | A1 | 10/2019 | Simpson |
| 2019/0333181 | A1 | 10/2019 | Simpson |
| 2019/0353499 | A1 | 11/2019 | Stenneth |
| 2020/0005388 | A1 | 1/2020 | Lim |
| 2020/0013498 | A1 | 1/2020 | Gelber |
| 2020/0027096 | A1 | 1/2020 | Cooner |
| 2020/0047055 | A1 | 2/2020 | Ward |
| 2020/0098071 | A1 | 3/2020 | Jackson |
| 2020/0125999 | A1 | 4/2020 | Simpson |
| 2020/0151816 | A1 | 5/2020 | Simpson |
| 2020/0156495 | A1 | 5/2020 | Lindup |
| 2020/0160461 | A1 | 5/2020 | Kaniki |
| 2020/0173808 | A1 | 6/2020 | Beaurepaire et al. |
| 2020/0184416 | A1 | 6/2020 | Javaheri |
| 2020/0219017 | A1 | 7/2020 | Simpson |
| 2020/0226853 | A1 | 7/2020 | Ahmed et al. |
| 2020/0317074 | A1 | 10/2020 | Miller et al. |
| 2020/0317075 | A1 | 10/2020 | Yokoyama et al. |
| 2020/0389301 | A1 | 12/2020 | Detres et al. |
| 2021/0004909 | A1 | 1/2021 | Farmer et al. |
| 2021/0012278 | A1 | 1/2021 | Alon et al. |
| 2021/0041258 | A1 | 2/2021 | Simpson |
| 2021/0042835 | A1 | 2/2021 | Simpson |
| 2021/0065100 | A1 | 3/2021 | Hwang |
| 2021/0158447 | A1 | 5/2021 | Simpson |
| 2021/0166317 | A1 | 6/2021 | Simpson |
| 2021/0248633 | A1 | 8/2021 | Simpson |
| 2021/0318132 | A1 | 10/2021 | Simpson |
| 2021/0326872 | A1 | 10/2021 | Robotham |
| 2021/0379447 | A1 | 12/2021 | Lee |
| 2021/0382924 | A1 | 12/2021 | Aaltonen et al. |
| 2022/0012432 | A1 | 1/2022 | Chen |
| 2022/0020073 | A1 | 1/2022 | Farmer |
| 2022/0058578 | A1 | 2/2022 | Javaheri |
| 2022/0068081 | A1 | 3/2022 | Pariseau |
| 2022/0100731 | A1 | 3/2022 | Tirapu Azpiroz et al. |
| 2022/0122026 | A1 | 4/2022 | Okabe et al. |
| 2023/0157579 | A1 | 5/2023 | Sato |
| 2023/0377409 | A1 | 11/2023 | Rye |
| 2024/0144006 | A1 | 5/2024 | Shazeer et al. |
| 2025/0217644 | A1 | 7/2025 | Shazeer et al. |

FOREIGN PATENT DOCUMENTS

| | | | |
|---|---|---|---|
| JP | 2003177034 | A | 12/2001 |
| JP | 7030853 | B2 | 3/2022 |
| KR | 20170078094 | A1 | 12/2015 |
| WO | 9508240 | A2 | 3/1995 |
| WO | 2001041084 | A2 | 6/2001 |
| WO | 2015059691 | A1 | 4/2015 |
| WO | 2015161307 | A1 | 4/2015 |
| WO | 2018024844 | A1 | 2/2018 |
| WO | 2019/134005 | A1 | 7/2019 |
| WO | 2019183468 | A1 | 9/2019 |
| WO | 2021/163675 | A1 | 8/2021 |

OTHER PUBLICATIONS

PCT International Search Report and Written Opinion; PCT/US2020/012208; Mar. 24, 2020.

Sun, et al.; Real-Time MUAV Video Augmentation with Geo-Information for Remote Monitoring; 2013 Fifth International Conference on Geo-Information Technologies for Natural Disaster Management; pp. 114-118; IEEE; 2013.

The Wayback Machine, Interest Rate Swaps, https://web.archive.org/web/20171006212154/https://global.pimco.com/en/gbl/resources/education/understanding-interest-rate-swaps, 2016, pp. 1-7.

Freight Derivatives—a Vital Tool For YOur Business, https://www.reedsmith.com/-/media/files/perspectives/2007/02/ freight-derivatives--a-vital-tool-for-your-business/files/freight-derivatives--a vital-tool-for-your-business/fileattachment/ etcfreightderivativesavitaltoolforyourbusiness.pdf (Year: 2007), Energy, Trade & Commodities, pp. 1-3.

Barry, Kieth, App lets drivers auction public parking spaces, Wired, Aug. 11, 2011, pp. 1-4.

Jiang, Landu, et al., Sun Chase: Energy-Efficient Route Planning for solar-powered Evs, IEEE 37th international conference on distrubuted computing systems, 2017, pp. 1-11.

Directed Graph, https://en.wikipedia.org/wiki/Directed_graph, pp. 1-6, 2022.

About IBM Food Trust, https://www.ibm.com/downloads/cas/E9DBNDJG, pp. 1-17, 2019.

IBM Blockchain Transparent Supply, https://www.ibm.com/downloads/cas/BKQDK0M2, pp. 1-14, Aug. 2020.

Radocchia, Samantha, 3 Innovative Ways Blockchain Will Build Trust In The Food Industry, https://www.forbes.com/sites/samantharadocchia/2018/04/26/3-innovative-ways-blockchain-will-build-trust-in-the-food-industry/?sh=65bc79f42afc, Forbes, pp. 1-5, Apr. 26, 2018.

Change the World, https://fortune.com/change-the-world/2019/ibm/, Fortune Media IP Limited, pp. 1-5, 2022.

IBM Food Trust, https://www.constellationr.com/node/17601/vote/application/view/588, Constellation Research Inc., pp. 1-4, 2010-2022.

Dey, Somdip, et al., FoodSQRBlock: Digitizing Food Production and the Supply Chain with Blockchain and QR Code in the Cloud, https://www.mdpi.com/2071-1050/13/6/3486/htm, MDPI, pp. 1-27, Mar. 22, 2021.

Ramasubramanian, Vasant, "Quadrasense: Immersive UAV-based cross-reality environmental sensor networks," phD diss., Massachusetts Institute of Technology, pp. 1-75, 2015.

Wyzant, https://web.archive.org/web/20190327185429/https://www.wyzant.com/hotitworks/students, Wyzant tutoring, pp. 1-13 , Mar. 27, 2019.

PCT International Search Report and Written Opinion; PCT/US2021/065855; Mar. 29, 2022.

PCT International Search Report and Written Opinion; PCT/US2022/012717; Mar. 30, 2022.

Zhao, et al., Incentives in Ridesharing with Deficit Control, Proceedings of the 13th International Conference on Autonomous Agents and Multiagent Systems (AAMAS 2014), May 5-9, 2014, pp. 1021-1028.

PCT International Search Report and Written Opinion; PCT/US2022/027077; Nov. 1, 2022.

Wei, et al. "impact of aircraft size and seat availability on airlines demand and market share in duopoly markets" Published by Elsevier, 2005, pp. 315-327.

PCT International Search Report and Written Opinion; PCT/US2022/052969; Mar. 21, 2023.

Little, T.D., et al., On the Joys of Missing Data, Journal of pediatric psychology, 2014, pp. 151-162.

(56) References Cited

OTHER PUBLICATIONS

Honaker, J., et al., What to do About Missing Values in Time-Series Cross-Section Data, American Journal of Political Science, Sep. 6, 2008, pp. 561-581.
Westerhoff, Market Depth and Price Dynamics: A Note, University of Osnabrueck, Department of Economics Rolandstrasse 8, D-49069 Osnabrueck, German, Mar. 30, 2004, pp. 1-8.
PCT International Search Report and Written Opinion; PCTUS2022/051998; Mar. 8, 2023.
EP23153137.7 European Search Report, May 24, 2023, pp. 1-10.
EP20787830.7 European Search Report, May 12, 2023, pp. 1-10.
Zheyong, Bian, et al., "Planning the Ridesharing Route for the First-Mile Service Linking to Railway Passenger Transportation," Joint Rail Conference, Apr. 2017, pp. 1-11.
EP23168879.7 European Search Report, Jul. 5, 2023, pp. 1-13.
Papa, U., & Del Core, G., "Design of Sonar Sensor Model for Safe Landing of an UAV," IEEE Metrology for Aerospace, 2015, pp. 346-350.
Li, Jundong, et al., "Multi-network Embedding", pp. 1-9, 2018.
Speediance, All-in-One Smart Home Gym; retrieved from internet: https://www.amazon.com/Speediance-Equipment-Resistance-Training-Machine-Works/dp/B0C4KF7844/?th=1; May 8, 2023; p. 1.
Freebeat, Smart Exercise Bike; retrieved from internet: https://www.amazon.com/Resistance-Cushioned-Detection-Altorithm-Instructors/dp/B0BZKKZ6B3/?th=1; Mar. 3, 2023; p. 1.
"Node Influence Metric", Wikipedia, Nov. 6, 2020, pp. 1-5.
EP21916571 European Search Report, May 29, 2024, pp. 1-9.
Bortolini, et al.; "Fresh food sustainable distribution: cost, delivery time and carbon footprint three-objective optimization," 2016, pp. 1-12.
Fulldomepro, VR Aquatic Simulator with a Dome, Pub. Sep. 3, 2018, https://www.youtube.com/watch?v=k_53G5DksjQ, pp. 1-2.
Randomoneh, Dome Screens & Displays, Pub. Oct. 12, 2012, https:// hardforum.com/threads/dome-screens-displays, p. 1.
Borgobello, Bridget, TOOB Personal Dome Screen Revamped, Pub. Jan. 12, 2012, https:// newatlas.com/toob-earth-personal-dome-screen/21082, p. 1.
Asghari, et al; "Price-aware Real-time Ride-sharing at Scale-An Auction-based Approach", Oct. 31, 2016, SIGSPACIAL'16: Proceedings of the 24th ACM SIGSPATIAl International Conference on Advances in Geographic Information Systems, Article No. 3, pp. 1-10.
EP22740218.7 European Search Report, Nov. 12, 2024, pp. 1-29.
EP23153137.7 Exam Report (Communication pursuant to Article 94(3) EPC), Mar. 5, 2025, pp. 1-11.
Chang, et al., "Estimating Real-Time Traffic Carbon Dioxide Emissions Based on Intelligent Transportation System Technologies," IEEE Mar. 1, 2013, vol. 14, pp. 1-11.
Karbassi, et al.; "Vehicle Route Prediction and Time of Arrival Estimation Techniques for Improved Transportation System Management" Published by IEEE; 2003, pp. 511-516.
Valdes, J. J., et al.; (Sep. 2007). Virtual reality high dimensional objective spaces for multi-objective optimization: An improved representation. In 2007 IEEE Congress on Evolutionary Computation (pp. 4191-4198). IEEE., pp. 1-11.
Valdes, J. J., et al.; (2007). Multi-objective evolutionary optimization for constructing neural networks for virtual reality visual data mining: Application to geophysical prospecting. Neural networks, 20(4), pp. 498-508.
Zhao, et al., Deshpande, P. M., Naughton, J. F., & Shukla, A (Jun. 1998). Simultaneous optimization and evaluation of multiple dimensional queries. In Proceedings of the 1998 ACM SIGMOD international conference on Management of data (pp. 271-282).
Aratani, Lori, "This app wants to reward you for smart commuting choices," The Washington Post, Aug. 18, 2018, pp. 1-3.
Yu, Haicong et al.; "A Multi-Modal Route Planning Approach with an Improved Genetic Algorithm", The International Archives of the Photogrammetry, Remote Sensing and Spaital Information Sciences, vol. 38, Part I, 2010, pp. 343-348.
B. P. Yuhas, M. H. Goldstein, and T. J. Sejnowski, "Integration of acoustic and visual speech signals using neural networks," IEEE Commun. Mag., vol. 27, No. 11, pp. 65-71, Nov. 1989.
W. Guo, J. Wang, and S. Wang, "Deep multimodal representation learning: A survey," IEEE Access, vol. 7, pp. 63373-63394, 2019.
L. Wu, S. L. Oviatt, and P. R. Cohen, "Multimodal integration-a statistical view," IEEE Trans. Multimedia, vol. 1, No. 4, pp. 334-341, Dec. 1999.
J. Shang, T. Ma, C. Xiao, and J. Sun, "Pre-training of graph augmented transformers for medication recommendation," 2019, arXiv: 1906.00346, 8 pages.
K. Gavrilyuk, R. Sanford, M. Javan, and C. G. Snoek, "Actor transformers for group activity recognition," inProc. IEEE Conf. Comput. Vis. Pattern Recognit., 2020, pp. 836-845.
Beltagy, M. E. Peters, and A. Cohan, "Longformer: The long-document transformer," 2020, arXiv:2004.05150, 17 pages.
D. Shin, Z. Ren, E. B. Sudderth, and C. C. Fowlkes, "3D scene reconstruction with multi-layer depth and epipolar transformers," in Proc. IEEE Int. Conf. Comput. Vis., 2019, pp. 2172-2182.
P. Xu et al., "SketchMate: Deep hashing for million-scale human sketch retrieval," in Proc. IEEE Conf. Comput. Vis. Pattern Recognit., 2018, pp. 8090-8098.
K. Gupta, J. Lazarow, A. Achille, L. Davis, V. Mahadevan, and A. Shrivastava, "LayoutTransformer: Layout generation and completion with self-attention," 2020, arXiv:2006.14615, Gupta et al.
T. Hastie, R. Tibshirani, J. H. Friedman, and J. H. Friedman, The Elements of Statistical Learning: Data Mining, Inference, and Prediction, vol. 2. Berlin, Germany: Springer, 2009, 9 pages.
C. Zhang, Z. Yang, X. He, and L. Deng, "Multimodal intelligence: Representation learning, information fusion, and applications," IEEE J. Sel. Topics Signal Process., vol. 14, No. 3, pp. 478-493, Mar. 2020.
C. Sun, A. Myers, C. Vondrick, K. Murphy, and C. Schmid, "VideoBERT: A joint model for video and language representation learning," in Proc. IEEE Int. Conf. Comput. Vis., 2019, pp. 7463-7472.
N. Carion, F. Massa, G. Synnaeve, N. Usunier, A. Kirillov, and S. Zagoruyko, "End-to-end object detection with transformers," in Proc. Eur. Conf. Comput. Vis., 2020, pp. 213-229.
J. Devlin, M.-W. Chang, K. Lee, and K. Toutanova, "BERT: Pretraining of deep bidirectional transformers for language understanding," 2018, arXiv: 1810.04805, 16 pages.
Vaswani et al., "Attention is all you need," in Proc. Int. Conf. Neural Inf. Process. Syst., 2017, pp. 5998-6008.
T. Baltrušaitis, C. Ahuja, and L.-P. Morency, "Multimodal machine learning: A survey and taxonomy." IEEE Trans. Pattern Anal. Mach. Intell., vol. 41, No. 2, pp. 423-443, Feb. 2019.
Cai, et al.; Incorporating Visual Information in Audio Based Self-Supervised Speaker Recognition; IEEE/ACM Transactions on Audio, Speech and Language Processing; vol. 30; pp. 1422-1435; Mar. 24, 2022.
Nikonowicz, et al., "Virtual Power Plants", Published by Open Acess Journal, 2012, pp. 135-149.
Garamvolgyi et al.; Towards_Model-Driven_Engineering_of_Smart_Contracts; IEEE/IFIP; pp. 134-139; 2018.
Khan et al; "A Distri buted-Ledger Consortium Model for Collaborative_Innovation" ; IEEE pp. 29-37; 2017.
Meiklejohn S.; Top Ten Obstacles along Distributed Ledgers Path to Adoption; UCL; pp. 13-19; 2017.
Muttavarapu et al.; Distributed_Ledger_for_Spammers_Resume; IEEE; 9 pages, 2018.
S. Pramanik, P. Agrawal, and A. Hussain, "OmniNet: A unified architecture for multi-modal multi-task learning," Jul. 3, 2020 v2 , arXiv:1907.07804, 16 pages.
R. Akula, S. Gella, Y. Al-Onaizan, S.-C. Zhu, and S. Reddy, "Words aren't enough, their order matters: On the robustness of grounding visual referring expressions," 2020, arXiv:2005.01655, 11 pages.
R. Child, S. Gray, A. Radford, and I. Sutskever, "Generating long sequences with sparse transformers," 2019, arXiv:1904.10509, 10 pages.

(56) References Cited

OTHER PUBLICATIONS

Y. Xian, C. H. Lampert, B. Schiele, and Z. Akata, "Zero-shot learning—A comprehensive evaluation of the good, the bad and the ugly," IEEE Trans. Pattern Anal. Mach. Intell., vol. 41, No. 9, pp. 2251-2265, Sep. 2019.
Owens and A. A. Efros, "Audio-visual scene analysis with selfsupervised multisensory features," inProc. Eur. Conf. Comput. Vis., 2018, pp. 639-658.
T. Chen and R. R. Rao, "Audio-visual integration in multimodal communication," Proc. IEEE, vol. 86, No. 5, pp. 837-852, May 1998.
N. Li, S. Liu, Y. Liu, S. Zhao, and M. Liu, "Neural speech synthesis with transformer network," in Proc. AAAI Conf. Artif. Intell., 2019, pp. 6706-6713.
M. Chen, Y. Li, Z. Zhang, and S. Huang, "TVT: Two-view transformer network for video captioning," in Proc. 10th Asian Conf. Mach. Learn., 2018, pp. 847-862.
X. Lin, C. Ding, J. Zeng, and D. Tao, "GPS-Net: Graph property sensing network for scene graph generation," in Proc. IEEE Conf. Comput. Vis. Pattern Recognit., 2020, pp. 3743-3752.
W. Hao, C. Li, X. Li, L. Carin, and J. Gao, "Towards learning a generic agent for vision-and-language navigation via pre-training," in Proc. IEEE Conf. Comput. Vis. Pattern Recognit., 2020, pp. 13134-13143.
S. Ren, K. He, R. Girshick, and J. Sun, "Faster R-CNN: Towards realtime object detection with region proposal networks," in Proc. Int. Conf. Neural Inf. Process. Syst., 2015, pp. 91-99.
Y.-H. H. Tsai, S. Bai, P. P. Liang, J. Z. Kolter, L.-P. Morency, and R. Salakhutdinov, "Multimodal transformer for unaligned multimodal language sequences," in Proc. Conf. Assoc. Comput. Linguistics, 2019, pp. 6558-6569.
J. Lin, A. Yang, Y. Zhang, J. Liu, J. Zhou, and H. Yang, "InterBERT: Vision-and-language interaction for multi-modal pretraining," 2020, arXiv:2003.13198. 11 pages.
D. Tran, H.Wang, L. Torresani, J. Ray, Y. LeCun, and M. Paluri, "A closer look at spatiotemporal convolutions for action recognition," inProc. IEEE Conf. Comput. Vis. Pattern Recognit., 2018, pp. 6450-6459.
S. Xie, C. Sun, J. Huang, Z. Tu, and K. Murphy, "Rethinking spatiotemporal feature learning for video understanding," 2017, arXiv:1712.04851, 17 pages.
L. Zhou, Y. Zhou, J. J. Corso, R. Socher, and C. Xiong, "End-to-end dense video captioning with masked transformer," in Proc. IEEE Conf. Comput. Vis. Pattern Recognit., 2018, pp. 8739-8748.
X. Wang, R. Girshick, A. Gupta, and K. He, "Non-local neural networks," in Proc. IEEE Conf. Comput. Vis. Pattern Recognit., 2018, pp. 7794-7803.
J. L. Ba, J. R. Kiros, and G. E. Hinton, "Layer normalization," 2016, arXiv:1607.06450, 14 pages.
S. Ioffe and C. Szegedy, "Batch normalization: Accelerating deep network training by reducing internal covariate shift," in Proc. Int. Conf. Mach. Learn., 2015, pp. 448-456.
K. He, X. Zhang, S. Ren, and J. Sun, "Deep residual learning for image recognition," in Proc. IEEE Conf. Comput. Vis. Pattern Recognit., 2016, pp. 770-778.
J. Malmaud, J. Huang, V. Rathod, N. Johnston, A. Rabinovich, and K. Murphy, "What's Cookin'? Interpreting cooking videos using text, speech and vision," 2015, arXiv:1503.01558, 10 pages.
L. Zhou, C. Xu, and J. J. Corso, "Towards automatic learning of procedures from web instructional videos," in Proc. AAAI Conf. Artif. Intell., 2018, pp. 7590-7598.
D. Kiela et al., The hateful memes challenge: Detecting hate speech in multimodal memes, 2020, arXiv:2005.04790, 17 pages.
Miech, D. Zhukov, J.-B. Alayrac, M. Tapaswi, I. Laptev, and J. Sivic, "HowTo100M: Learning a text-video embedding by watching hundred million narrated video clips," in Proc. IEEE Int. Conf. Comput. Vis., 2019, pp. 2630-2640.
Das et al., "Visual dialog," in Proc. IEEE Conf. Comput. Vis. Pattern Recognit., 2017, pp. 1080-1089.
R. Krishna, K. Hata, F. Ren, L. Fei-Fei, and J. C. Niebles, "Densecaptioning events in videos," in Proc. IEEE Int. Conf. Comput. Vis., 2017, pp. 706-715.
V. Ordonez, G. Kulkarni, and T. Berg, "Im2Text: Describing images using 1 million captioned photographs," in Proc. Int. Conf. Neural Inf. Process. Syst., 2011, pp. 1143-1151.
R. Krishna et al., "Visual genome: Connecting language and vision using crowdsourced dense image annotations," Int. J. Comput. Vis., vol. 123, pp. 32-73, 2017.
S. Antol et al., "VQA: Visual question answering," in Proc. IEEE Int. Conf. Comput. Vis., 2015, pp. 2425-2433.
T.-Y. Lin et al., "Microsoft COCO: Common objects in context," in Proc. Eur. Conf. Comput. Vis., 2014, pp. 740-755.
P. Sharma, N. Ding, S. Goodman, and R. Soricut, "Conceptual captions: A cleaned, hypernymed, image alt-text dataset for automatic image captioning," in Proc. Conf. Assoc. Comput. Linguistics, 2018, pp. 2556-2565.
H. Luo et al., "UniVL: A unified video and language pre-training model for multimodal understanding and generation," 2020, arXiv:2002.06353, 15 pages.
D. Qi, L. Su, J. Song, E. Cui, T. Bharti, and A. Sacheti, "ImageBERT: Cross-modal pre-training with large-scale weak-supervised image-text data," 2020, arXiv:2001.07966, 12 pages.
Z. Huang, Z. Zeng, B. Liu, D. Fu, and J. Fu, "Pixel-BERT: Aligning image pixels with text by deep multi-modal transformers," 2020, arXiv:2004.00849, 17 pages.
X. Li et al., "Oscar: Object-semantics aligned pre-training for vision-language tasks," in Proc. Eur. Conf. Comput. Vis., 2020, pp. 121-137.
J. Lu, V. Goswami, M. Rohrbach, D. Parikh, and S. Lee, "12-in-1: Multitask vision and language representation learning," in Proc. IEEE Conf. Comput. Vis. Pattern Recognit., 2020, pp. 10434-10443.
L. Zhou, H. Palangi, L. Zhang, H. Hu, J. Corso, and J. Gao, "Unified vision-language pre-training for image captioning and VQA," in Proc. AAAI Conf. Artif. Intell., 2020, pp. 13041-13049.
C. Alberti, J. Ling, M. Collins, and D. Reitter, "Fusion of detected objects in text for visual question answering," 2019, arXiv:1908.05054, 10 pages.
G. Li, N. Duan, Y. Fang, M. Gong, and D. Jiang, "Unicoder-VL: A universal encoder for vision and language by cross-modal pre-training," in Proc. AAAI Conf. Artif. Intell., 2020, pp. 11336-11344.
C. Sun, F. Baradel, K. Murphy, and C. Schmid, "Learning video representations using contrastive bidirectional transformer," 2019, arXiv:1906.05743, 12 pages.
Y.-C. Chen et al., "UNITER: Universal image-text representation learning," in Proc. Eur. Conf. Comput. Vis., 2020, pp. 104-120.
W. Su et al., "VL-BERT: Pre-training of generic visual-linguistic representations," 2019, arXiv:1908.08530.
L. H. Li, M. Yatskar, D. Yin, C.-J. Hsieh, and K.-W. Chang, "VisualBERT: A simple and performant baseline for vision and language," 2019, arXiv:1908.03557, 16 pages.
H. Tan and M. Bansal, "LXMERT: Learning cross-modality encoder representations from transformers," 2019, arXiv:1908.07490.
J. Lu, D. Batra, D. Parikh, and S. Lee, "ViLBERT: Pretraining taskagnostic visiolinguistic representations for vision-and-language tasks," 2019, arXiv:1908.02265, 11 pages.
Z. Yang, Z. Dai, Y. Yang, J. Carbonell, R. R. Salakhutdinov, and Q. V. Le, "XLNet: Generalized autoregressive pretraining for language understanding," in Proc. Int. Conf. Neural Inf. Process. Syst., 2019, Art. No. 517, 18 pages.
Z. Dai, Z. Yang, Y. Yang, J. Carbonell, Q. V. Le, and R. Salakhutdinov, "Transformer-XL: Attentive language models beyond a fixed-length context," 2019, arXiv:1901.02860, 20 pages.
Radford, K. Narasimhan, T. Salimans, and I. Sutskever, "Improving language understanding by generative pre-training," 2018. [Online]. Available: https://s3-us-west-2.amazonaws.com/openai-assets/research-covers/language-unsupervised/language_understanding_ paper.pdf, 12 pages.
M. Lewis et al., "BART: Denoising sequence-to-sequence pre-training for natural language generation, translation, and comprehension," 2019, arXiv: 1910.13461, 10 pages.

(56) References Cited

OTHER PUBLICATIONS

Y. Li et al., "BEHRT: Transformer for electronic health records," Sci. Rep., vol. 10, 2020, Art. No. 7155, 12 pages.
Chen, M., et al.; What may visualization processes optimize ?. IEEE transactions on visualization and computer. 2015, pp. 1-10.
Meneghini, et al.; Information to the Eye of the Beholder: Data Visualization for Many-Objective Optimization; Institute for polymers and Composites, University of Minho, pp. 1-9; 2018.
Franco, et al.; "Road vehicle emission factors development: A review" Published by Elsevier (Year: 2013); pp. 84-97.
Westerman; Longitudinal Analysis of Biomarker Data from a Personalized Nutrition Platform in Healthy Subjects; Nature, Scientific Reports; vol. 8; Oct. 2, 2018 (retrieved Jun. 10, 2020). https://www.nature.com/articles/s41598-018-33008-7, 10 pages.
Ahmed, et al.; Energy Trading with Electric Vehicles in Smart Campus Parking Lots; Applied Sciences; Sep. 7, 2018, 17 pages.
Fitzsimmons; Uber Hit with Cap as New York City Takes Lead in Crackdown; New York Times; Aug. 8, 2018 (retrieved Feb. 29, 2020). https://www.wral.com/uber-hit-with-cap-as-new-york-city-takes-lead-in-crackdow/17755819/?version=amp?, 6 pages.
Peters, et al.; Student Support Services for Online Learning Re-Imagined and Re-Invigorated: Then, Now and What's To Come; Contact North | Contact Nord; Sep. 2017, 17 pages.
Soccer ball-shaped drone might be the safest flying robot yet; Dec. 21, 2015 (retrieved Feb. 24, 2021). https://mashable.com/2015/12/21/soccer-ball-drone/, 2 pages.
Fleishman; Use Parking Apps to Find Lots, Garages, Valet, and Meters; Macworld; Jul. 19, 2015, 9 pages.
Borras, et al. Intelligent Tourism Reminder Systems: A Survey; Expert Systems with Applications 41; pp. 7370-7389; Elsevier; Jun. 9, 2014.
Pentland; After Decades of Doubt, Deregulation Delivers Lower Electricity Rates; Forbes; Oct. 13, 2013 (retrieved Feb. 29, 2020). https://www.forbes.com/sites/williampentland/2013/10/13/after-decades-of-doubt-deregulation-delivers-lower-electricity-prices/#201d4a9c1d13, 3 pages.
Page, Lawrence; U.S. Appl. No. 60/035,205, filed Jan. 10, 1997.
Electronic Exchange; NetLingo, The Internet Dictionary; Oct. 22, 2017. https://web.archive.org/web/20170122184857/https://www.netlingo.com/word/electronic-exchange.php, 1 page.
Laseter, et al.; "B2B benchmark: The State of Electronic Exchanges"; Strategy + Business; Fourth Quarter 2001, Issue 25, Tech & Innovation; Oct. 1, 2001. https://www.strategy-business.com/article/14300, 25 pages.
Luong, et al.; Effective Approaches to Attention-based Neural Machine Translation; EMNLP 2015; Aug. 17, 2015, pp. 1-11. https://arxiv.org/abs/1508.04025.
Bahdanau, et al.; Neural Machine Translation by Jointly Learning to Align and Translate; ICLR 2015; Sep. 1, 2014, pp. 1-15. https://arxiv.org/abs/1409.0473.
Silverman, "New App Will Let You Buy Or Sell A Parking Space In Nyc", Cbs News, Jul. 20, 2011; https://www.cbsnews.com/newyork/news/new-app-will-let-you-buy-or-sell-a-parking-space/ (Year: 2011) 6 pages.
Kazemi, et al., "Time2Vec: Learning a Vector Representation of Time," arXiv preprint arXiv:1907.05321, pp. 1-16. (2019).
Shaw et al., "Self-Attention with Relative Position Representations," 2018 Conference of the North American Chapter of the Association for the Computation Linguistics: Human Language Technologies, vol. 2 (Short Papers), pp. 1-5, (2018).
Dosovitskiy et al., "An Image is Worth 16x16 Words: Transformers for Image Recognition at Scale," arXiv preprint arXiv:2010.11929, pp. 1-22. (2020).
Rumelhart et al., "Learning Representations By Back-Propagating Errors," Nature 323, 533-536 (1986).
Hochreiter et al., "Long Short-Term Memory," Neural Computation, vol. 9, No. 8, pp. 1735-178 (Nov. 15, 1997).
Lecun et al., "Backpropagatin Applied to Handwritten Zip Code Recognition," Neural Computation, vol. 1, No. 4, pp. 541-551 (Dec. 1989).
Zhang et al., "Parallel Distribution Processing Model With Local Space-Invariant Interconnections and its Optical Architecture," Appl. Opt. vol. 29, No. 32, pp. 4790-4797 (Nov. 29, 199).
Krizhevsky et al., "Image Classification with Deep Convolutional Neural Networks," Advances in Neural Information Processing Systems 25, Nueral Information Processing Systems Conference (2012).
Parikh et al. "A Decomposable Attention Model For Natural Language Interence," 2016 Conference On Empirical Methods In Natural Language Processing, pp. 2249-2255 (Nov. 2016).

* cited by examiner

1000

1010

Maximize Foodie Score, User utility, Nutrition Content, flavoring, ethnicity, variety, style, preference, health, delivery Subject to the following possible constraints

| | | |
|---|---|---|
| Blood Type | Phosphorus | Platelets |
| HDL Cholesterol | Thyroid | Hemoglobin |
| Iron | Vitamin B12 | Hematocrit |
| Ketones | Amylase | Mean Corpuscular Volume |
| LDL Cholesterol | Serum Protein | Blood Glucose |
| Magnesium | Complete Blood Count (CBC) | |
| Potassium | Red Blood Cells | Calcium |
| Progesterone | White Blood Cells | Electrolytes |
| Creatine Kinase | Triglycerides | Allergen Profile |
| Troponin | Coagulation Panel | Celiac, budget |
| HLA-DQ8 gene | HLA-DQ2 gene | Sum of Ingredient |
| Allergies | other | weights = 1 |
| Beta Amyloid | Serum docosahexaenoic acid | |
| tau phosphorylation | serum low-density lipoprotein (LDL) | |

1020

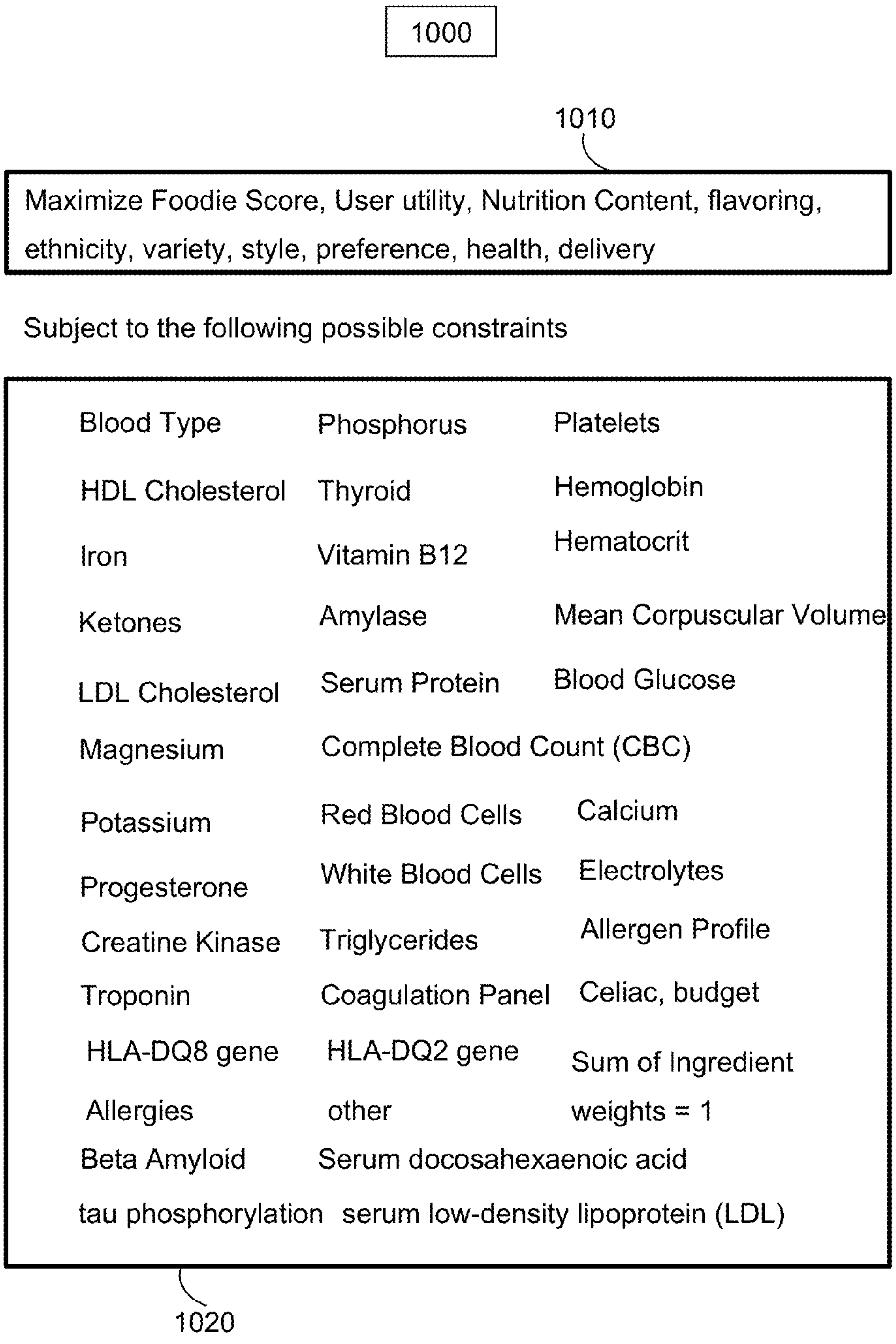

$$F_{\text{foodie score}} = E(B_{\text{Blood Chemistry}}) - 0.005A\,\sigma^2_{\text{Blood chemistry}}$$

Take an initial Blood Chemistry with a vector of attributes and assume two possible results after eating meal that is a meal with a vector of blood chemistry attributes.

With a probability p

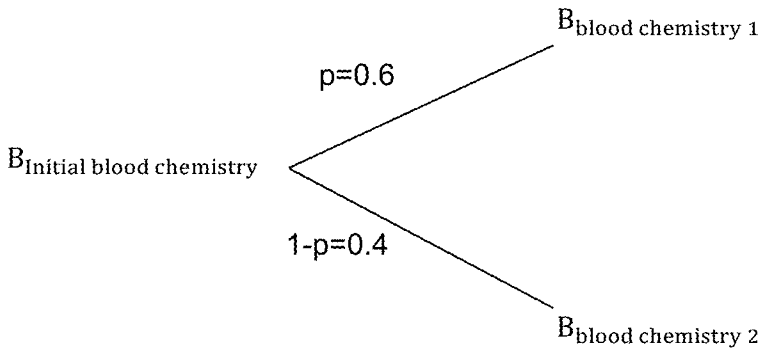

1430

So the expected value of Blood Chemistry is:

$$E(B_{\text{Blood Chemistry}}) = p(B_{\text{blood chemistry 1}}) + (1-p)(B_{\text{blood chemistry2}})$$

1440

The variance $\sigma^2$ of the blood chemistry is $$\sigma^2 = p[B_{\text{blood chemistry1}} - E(B_{\text{blood chemistry}})]^2 + (1-p)[B_{\text{blood chemistry2}} - E(B_{\text{blood chemistry}})]^2$$

The standard deviation of blood chemistry is $\sigma = \sqrt{\sigma^2}$

Accordingly, if $E_{\text{blood chemistry meal 1}} \geq E_{\text{blood chemistry meal 2}}$ and $\sigma_{\text{blood chemistry meal 1}} \leq \sigma_{\text{blood chemistry meal 2}}$ and at least one inequality is strict, inequality has been ruled out

1600

1610

1620

| E blood chemistry meal | σ blood chemistry meal | $F_{foodie\ score} = E(B_{Blood\ Chemistry}) - 0.005A\ \sigma^2_{Blood\ chemistry}$ |
|---|---|---|
| 10 | 20.0% | 10 – 0.005 x 4 x 400 = 2 |
| 15 | 25.5% | 15 – 0.005 x 4 x 650 = 2 |
| 20 | 30.0% | 20 – 0.005 x 4 x 900 = 2 |
| 25 | 33.9% | 25 – 0.005 x 4 x 1,150 = 2 |

1700

1710

| | State 1 | State 2 | State 3 |
|---|---|---|---|
| Rapini Probability | 0.5 | 0.3 | 0.2 |
| Rapini Blood Chemistry Toward target | 25% Increase to target | 10% Increase to target | -25% decrease to target |
| | | | |

The mean or expected return of an ingredient is a probability weighted return

In all scenarios:

$$E(r) = \sum_{s} Pr(s)\, r(s)$$

Applying the aformentioned formula to 1710 above we have $$E(r_{ingredient}) = 0.5x25 + 0.3x10 + 0.2x(-25)$$

The variance of Rapini on blood chemistry is $$\sigma^2 = \sum_{s} Pr(s)\,[r(s) - E(r)]^2$$

Applying the aformentioned formula to 1710 above we have $$\sigma^2_{rapini} = (0.5(25 - 10.5)^2 + 0.3(10 - 10.5)^2 + 0.2(-25 - 10.5)^2 = 357.25$$

Or $\sigma_{rapini} = \sqrt{357.25} = 18.99\%$

$$E(r_{meal}) = 0.5(E(r_{rapini})) + 0.5(E(r_{chocolate}))$$

= 0.5x10.5 +0.5x5 = 7.75%, when Rapini is combined with chocolate

$$\sigma_{Foodie} = 0.5(\sigma_{rapini}) + 0.5(\sigma_{chocolate})$$

The standard deviation of the combination of ingredients

$$[r_{rapini} - E(r_{rapini})][r_{chocolate} - E(r_{chocolate})]$$

$$Cov(r_{rapini,} r_{chocolate}) = \sum_{s} Pr(s)\,[r_{rapini}(S) - E(r_{rapini})][r_{chocolate}(s) - E(r_{chocolate})]$$

$$\rho(\text{rapini, chocolate}) = \frac{\text{Cov}[r_{\text{rapini}}, r_{\text{chocolate}}]}{\sigma_{\text{rapini}}\sigma_{\text{chocolate}}}$$

1910

FIG. 19A $$\sigma^2_{\text{blood chemistry}} = w_1^2\sigma^2 + w_2^2\sigma_2^2 + 2w_1w_2\text{Cov}(r_1 r_2)$$

Where subscript 1 is rapini or another ingredient and

Subscript 2 is chocolate or another ingredient

1920

FIG. 19B $$\max_{\text{vector of ingredients}}[F_{\text{foodie Score}}] = E\left(r_{\substack{\text{Blood}\\\text{chem}\\\text{meal}}}\right) - 0.005A\sigma^2_{\substack{\text{blood}\\\text{chem}\\\text{meal}}}$$

Where term A is the Foodie's user preference index

| | $meal_1$ or $ing_1$ | $meal_2$ or $ing_2$ |
|---|---|---|
| Meal or ingredient weights | $w_{ing\ 1}$ | $w_{ing2}$ |
| $w_{ing\ 1}$ | $\sigma^2_{ing\ 1}$ | $Cov(r_{ing1}, r_{ing2})$ |
| $w_{ing\ 2}$ | $Cov(r_{ing\ 1}, r_{ing\ 2})$ | $\sigma^2_{ing\ 2}$ |

| | Ingredient 1 | Ingredient 2 |
|---|---|---|
| Expected blood chemistry; E(r) | 8% | 13% |
| Standard deviation ; $\sigma$ | 12% | 20% |
| Covariance; $Cov(r_{ing1}, r_{ing2})$ | 72 | |
| Correlation Coefficient ; $\rho_{ing1,ing2}$ | 0.30 | |

| $w_{rapini}$ | $w_{chocolate}$ | $\rho = -1$ | $\rho = 0$ | $\rho = 0.3$ | $\rho = 1$ |
|---|---|---|---|---|---|
| 0.0 | 1.00 | 20.00% | 20.00% | 20.00% | 20.00% |
| 0.25 | 0.75 | 12.00 | 15.3 | 16.16 | 18.00 |
| 0.50 | 0.50 | 4 | 11.66 | 13.11 | 16.00 |
| 0.75 | 0.25 | 4.00 | 10.30 | 11.53 | 14.00 |
| 1.00 | 0.0 | 12.00 | 12.00 | 12.00 | 12.00 |
| Minimum $\sigma_m$ | | 0.00 | 10.29 | 11.45 | - |
| $w_{rapini}$@min$\sigma_m$ | | 0.63 | 0.74 | 0.82 | - |

2200

2210

2220

2300

2310

$$Slope_{Foodie\ Allocation\ Line\ (A)} = \frac{E(blood\ chemistry)_{Rapini,chocolate} - Ingredient_{no\ \sigma}}{\sigma_{rapini,chocolate}}$$

$$= \frac{8.9-5}{11.45} = 0.34$$

2320

2400

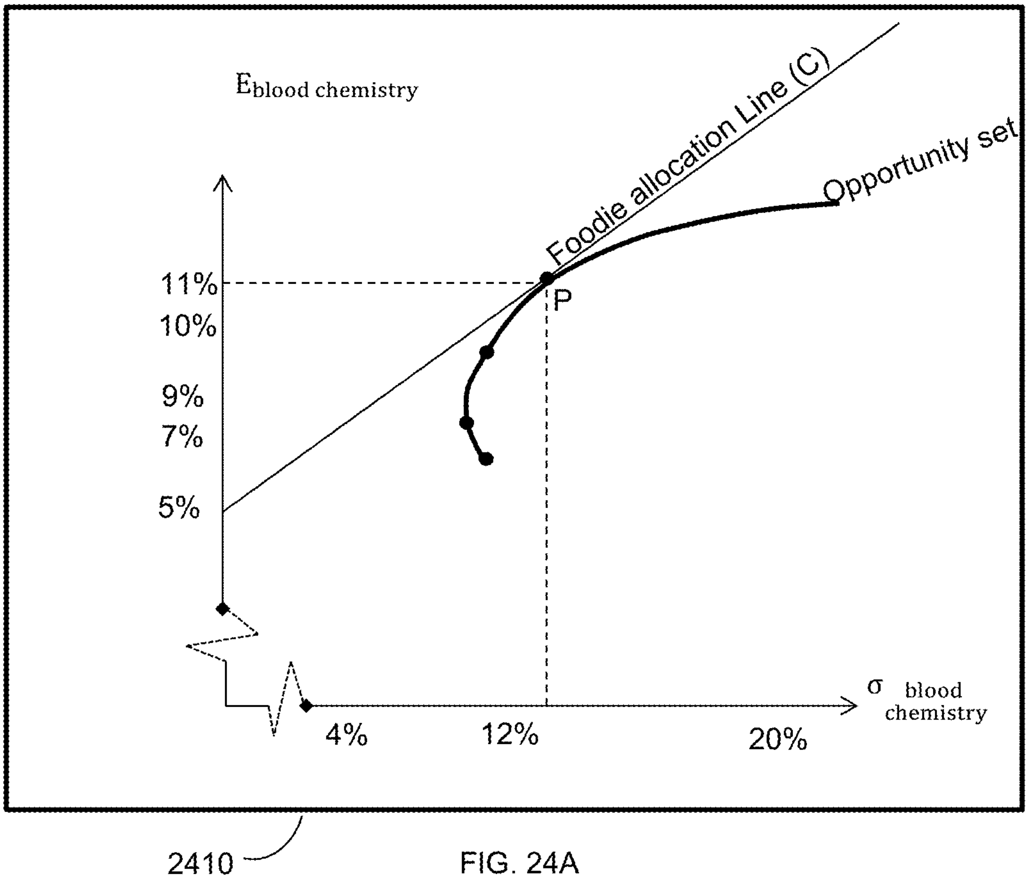

2410

FIG. 24A $$\text{Slope}_{\text{Foodie allocation line}} = \frac{E_{\text{blood chemistry}} - \text{Water}_{\text{blood chemistry}}}{\sigma_{\text{blood chemistry}}}$$

$$E_{\text{blood chemistry(BC) of combination}} = w_{\text{rapini}} E_{\text{rapini(BC)}} + w_{\text{chocolate}} E_{\text{chocolate(BC)}}$$

$$= 8w_{\text{rapini}} + 13w_{\text{chocolate}}$$

$$\sigma_{\text{blood chemistry combination}} = [w_{\text{rap}}^2 \sigma_{\text{rap}}^2 + w_{\text{choc}}^2 \sigma_{\text{choc}}^2 + 2w_{\text{rap}} w_{\text{choc}} \text{Cov}(r_{\text{rap}} r_{\text{choc}})]^{\frac{1}{2}}$$

$$= [144w_{\text{rap}}^2 + 400w_{\text{choc}}^2 + 2\text{x}72 w_{\text{rap}} w_{\text{choc}}]^{\frac{1}{2}}$$

$$\max_{w_i} \text{Slope}_{\text{Foodie allocation line}} = \frac{E_{\text{blood chemistry}} - \text{Water}_{\text{blood chemistry}}}{\sigma_{\text{blood chemistry}}}$$

Subject to $\sum w_i = 1$, which is the standard problem in calculus.

2510

FIG. 25A $$w_{rapini} = \frac{[E(r_{rapBC}) - \text{Water}_{BC}]\sigma^2_{chocBC} - [E(r_{chocBC}) - \text{Water}_{BC}]Cov(r_{rapBC}, r_{chocBC})}{[E(r_{rapBC}) - \text{Water}_{BC}]\sigma^2_{chocBC} + [E(r_{chocBC}) - \text{Water}_{BC}]\sigma^2_{rapBC} - [E(r_{rapBC}) - \text{Water}_{BC} + E(r_{chocBC}) - \text{Water}_{BC}]Cov(r_{rapBC,chocBC})}$$

$$w_{chocolate} = 1 - w_{rapini}$$

$$w_{rapini} = \frac{(8-5)400-(13-5)72}{(8-5)400+(13-5)144-(8-5+13-5)72} = 0.40$$

$$w_{chocolate} = 1 - 0.40 = 0.6$$

2520

FIG. 25B $$y = \frac{E(r_{\text{combination meal}}) - \text{Water}_{BC}}{0.01 \text{ x } A\sigma^2_{\text{combination meal}}}$$

$$= \frac{11-5}{0.01\text{x}4\text{x}14.2^2} = 0.7439$$

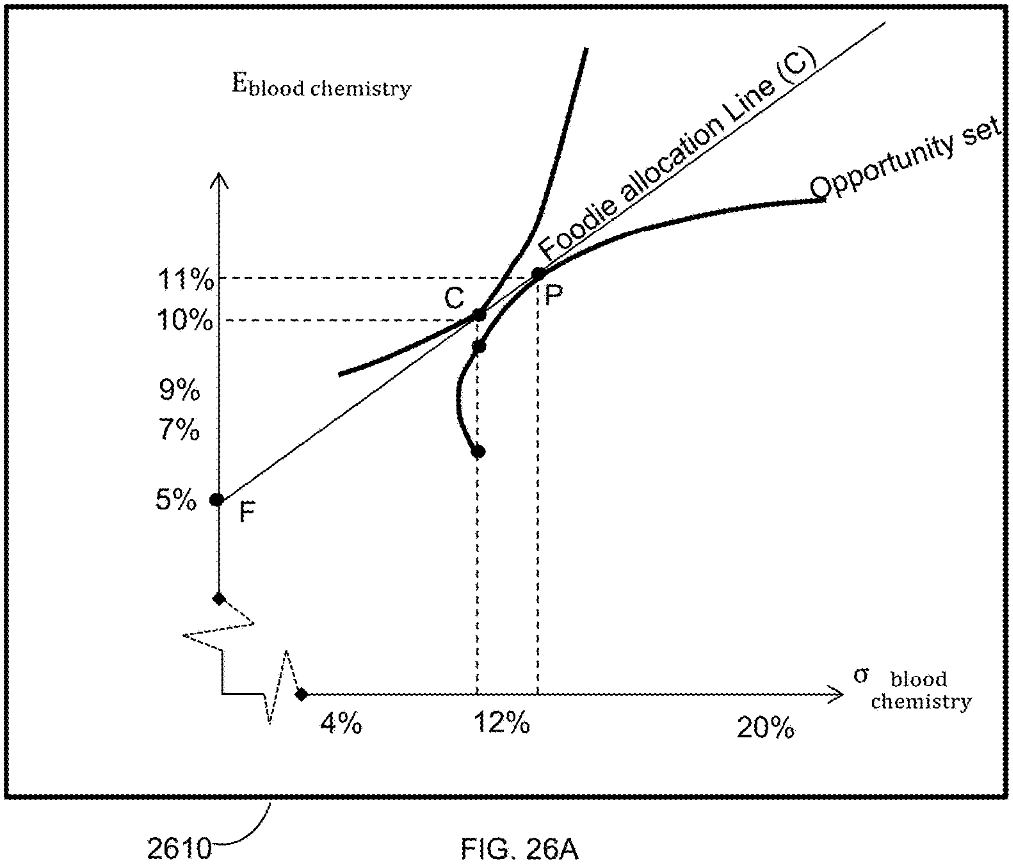

Specify the blood chemistry of all ingredients (expected blood chemistry, variances and covariances)

Establish the combination of ingredients

Calculate the optimal ingredient combination

Calculate the properties of the ingredient combination using weights determined by optimization.

Allocate calories between ingredient combo and water.

Calculate the fraction of the complete meal towards the ingredients and water

Calculate the share of calories in each ingredient and water

$$E(r_p) = \sum_{i=1}^{n} w_i E(r_i)$$

$$\sigma_p^2 = \sum_{i=1}^{n} w_i^2 \sigma_i^2 + \sum_{\substack{i=1 \\ i \neq j}}^{n} \sum_{j=1}^{n} w_i w_j Cov(r_i, r_j)$$

2810

2820

2900

$$w \in R^d$$

Vector w is a set of ingredient weights $w = \begin{bmatrix} w_1 \\ w_2 \\ \vdots \\ w_d \end{bmatrix}$ where $w_1 + w_2 + \cdots + w_d = 1$ Let the expected meal ingredient blood and saliva chemistry vector be $$r = \begin{bmatrix} r_1 \\ r_1 \\ \cdot \\ \cdot \\ r_d \end{bmatrix}, E(r) = \begin{bmatrix} E(r_1) \\ E(r_2) \\ \cdot \\ \cdot \\ E(r_d) \end{bmatrix}$$

Variance – covariance Matrix of ingredients in the meal ingredient combination $$\sum = \begin{bmatrix} \sigma_1^2 & \cdots & \sigma_{1d} \\ \vdots & \ddots & \vdots \\ \sigma_{1d} & \cdots & \sigma_d^2 \end{bmatrix}$$

$$r_p = w' x\, r = [w_1 \quad \cdots \quad w_d] x \begin{bmatrix} r_1 \\ \vdots \\ r_d \end{bmatrix}$$

$$E(r_p) = w' x\, E(r)$$

$$\sigma_p^2 = w' x \sum x\, w = [w_1 \ldots w_d] \begin{bmatrix} \sigma_1^2 & \cdots & \sigma_{1d} \\ \vdots & \ddots & \vdots \\ \sigma_{1d} & \cdots & \sigma_d^2 \end{bmatrix} \begin{bmatrix} w_1 \\ \vdots \\ w_d \end{bmatrix}$$

Egg, yolk, raw, frozen, pasteurized

| Nutrients and Units | Amount in 100 grams of edible portion | | | | | | Amount in edible portion of common measures of food | | |
|---|---|---|---|---|---|---|---|---|---|
| | Mean | Std. Error | Number of Data Points | Deriv Code | Source Code | Confidence Code | Measure 1 | Measure 2 | Measure 3 |
| Tocotrienol, delta ... μg | | | | | | | | | |
| Vitamin D (D2 + D3) ... μg | 5.0 | | 20 | AS | 1 | | 2.7 | 13.5 | |
| Vitamin D ... IU | 230 | | 0 | AS | 4 | | 60 | 541 | |
| Vitamin K (phylloquinone) ... μg | 0.7 | | 0 | NPN | 4 | | 0.3 | 1.5 | |
| Dihydrophylloquinone ... μg | | | | | | | | | |
| Menaquinone-4 ... μg | | | | | | | | | |
| **Lipids:** | | | | | | | | | |
| Fatty acids, total saturated ... g | 9.618 | | 0 | NC | 4 | | 2.443 | 13.566 | |
| 4:0 ... g | 0.000 | 0.000 | 15 | A | 1 | | 0.000 | 0.000 | |
| 6:0 ... g | 0.000 | 0.000 | 15 | A | 1 | | 0.000 | 0.000 | |
| 8:0 ... g | 0.000 | 0.000 | 15 | A | 1 | | 0.000 | 0.000 | |
| 10:0 ... g | 0.000 | 0.000 | 15 | A | 1 | | 0.000 | 0.000 | |
| 12:0 ... g | 0.000 | 0.000 | 15 | A | 1 | | 0.000 | 0.000 | |
| 13:0 ... g | | | | | | | | | |
| 14:0 ... g | 0.093 | 0.001 | 15 | A | 1 | | 0.024 | 0.133 | |
| 15:0 ... g | 0.022 | 0.000 | 15 | A | 1 | | 0.006 | 0.055 | |
| 16:0 ... g | 6.211 | 0.020 | 15 | A | 1 | | 1.761 | 14.000 | |
| 17:0 ... g | 0.093 | 0.001 | 15 | A | 1 | | 0.014 | 0.116 | |
| 18:0 ... g | 3.249 | 0.011 | 15 | A | 1 | | 0.627 | 5.104 | |
| 20:0 ... g | 0.000 | 0.000 | 15 | A | 1 | | 0.000 | 0.000 | |
| 22:0 ... g | 0.000 | 0.000 | 15 | A | 1 | | 0.000 | 0.000 | |
| 24:0 ... g | 0.000 | 0.000 | 15 | A | 1 | | 0.000 | 0.000 | |
| Fatty acids, total monounsaturated ... g | 9.556 | | 0 | NC | 4 | | 2.823 | 23.500 | |
| 15:1 ... g | 0.000 | 0.000 | 15 | A | 1 | | 0.000 | 0.000 | |
| 16:1 undifferentiated ... g | 0.548 | 0.013 | 15 | A | 1 | | 0.156 | 1.238 | |
| 17:1 ... g | 0.000 | 0.000 | 15 | A | 1 | | 0.000 | 0.000 | |
| 18:1 undifferentiated ... g | 9.331 | 0.144 | 15 | AS | 1 | | 2.645 | 21.581 | |
| 18:1 c ... g | 9.261 | 0.142 | 15 | A | 1 | | 2.608 | 21.923 | |
| 18:1 t ... g | 0.069 | 0.006 | 15 | A | 1 | | 0.020 | 0.158 | |
| 18:1-11 t (18:1n-7) ... g | | | | | | | | | |
| 20:1 ... g | 0.068 | 0.001 | 15 | A | 1 | | 0.038 | 0.153 | |
| 22:1 undifferentiated ... g | 0.000 | 0.000 | 15 | A | 1 | | 0.000 | 0.000 | |
| 24:1 c ... g | | | | | | | | | |
| Fatty acids, total polyunsaturated ... g | 4.927 | | 0 | NC | 4 | | 1.588 | 50.997 | |
| 18:2 undifferentiated ... g | 4.005 | 0.175 | 15 | AS | 1 | | 1.127 | 9.100 | |
| 18:2 n-6 c,c ... g | 3.980 | 0.174 | 15 | A | 1 | | 1.130 | 9.638 | |
| 18:2 CLAs ... g | | | | | | | | | |
| 18:2 t,t ... g | 0.039 | 0.003 | 15 | A | 1 | | 0.008 | 0.066 | |
| 18:2 i ... g | | | | | | | | | |
| 18:2 not further defined ... g | | | | | | | | | |
| 18:3 undifferentiated ... g | 0.126 | 0.016 | 15 | AS | 1 | | 0.035 | 0.281 | |
| 18:3 n-3 c,c,c (ALA) ... g | 0.093 | 0.013 | 15 | A | 1 | | 0.026 | 0.216 | |
| 18:3 n-6 c,c,c ... g | 0.031 | 0.003 | 15 | A | 1 | | 0.009 | 0.071 | |
| 18:3i ... g | 0.000 | 0.000 | 15 | A | 1 | | 0.000 | 0.000 | |
| 18:4 ... g | 0.000 | 0.000 | 15 | A | 1 | | 0.000 | 0.000 | |
| 20:2 n-6 c,c ... g | 0.047 | 0.002 | 15 | A | 1 | | 0.013 | 0.197 | |
| 20:3 undifferentiated ... g | 0.000 | 0.000 | 15 | A | 1 | | 0.000 | 0.000 | |
| 20:3 n-3 ... g | | | | | | | | | |
| 20:3 n-6 ... g | | | | | | | | | |
| 20:4 undifferentiated ... g | 0.400 | 0.012 | 15 | A | 1 | | 0.139 | 1.113 | |
| 20:4 n-6 ... g | | | | | | | | | |
| 20:5 n-3 (EPA) ... g | 0.000 | 0.000 | 15 | A | 1 | | 0.000 | 0.000 | |
| 21:5 ... g | | | | | | | | | |
| 22:4 ... g | | | | | | | | | |
| 22:5 n-3 (DPA) ... g | 0.002 | 0.000 | 15 | A | 1 | | 0.004 | 0.058 | |
| 22:6 n-3 (DHA) ... g | 0.138 | 0.005 | 15 | A | 1 | | 0.036 | 0.307 | |
| Fatty acids, total trans ... g | 0.068 | | 0 | NC | 4 | | 0.038 | 0.234 | |
| Fatty acids, total trans-monoenoic ... g | 0.069 | | 0 | NC | 4 | | 0.020 | 0.158 | |
| Fatty acids, total trans-polyenoic ... g | 0.038 | | 0 | NC | 4 | | 0.008 | 0.066 | |
| Cholesterol ... mg | 995 | | 3 | A | 1 | | 265 | 2350 | |
| Phytosterols ... mg | | | | | | | | | |
| **Amino Acids:** | | | | | | | | | |

Figure 32:
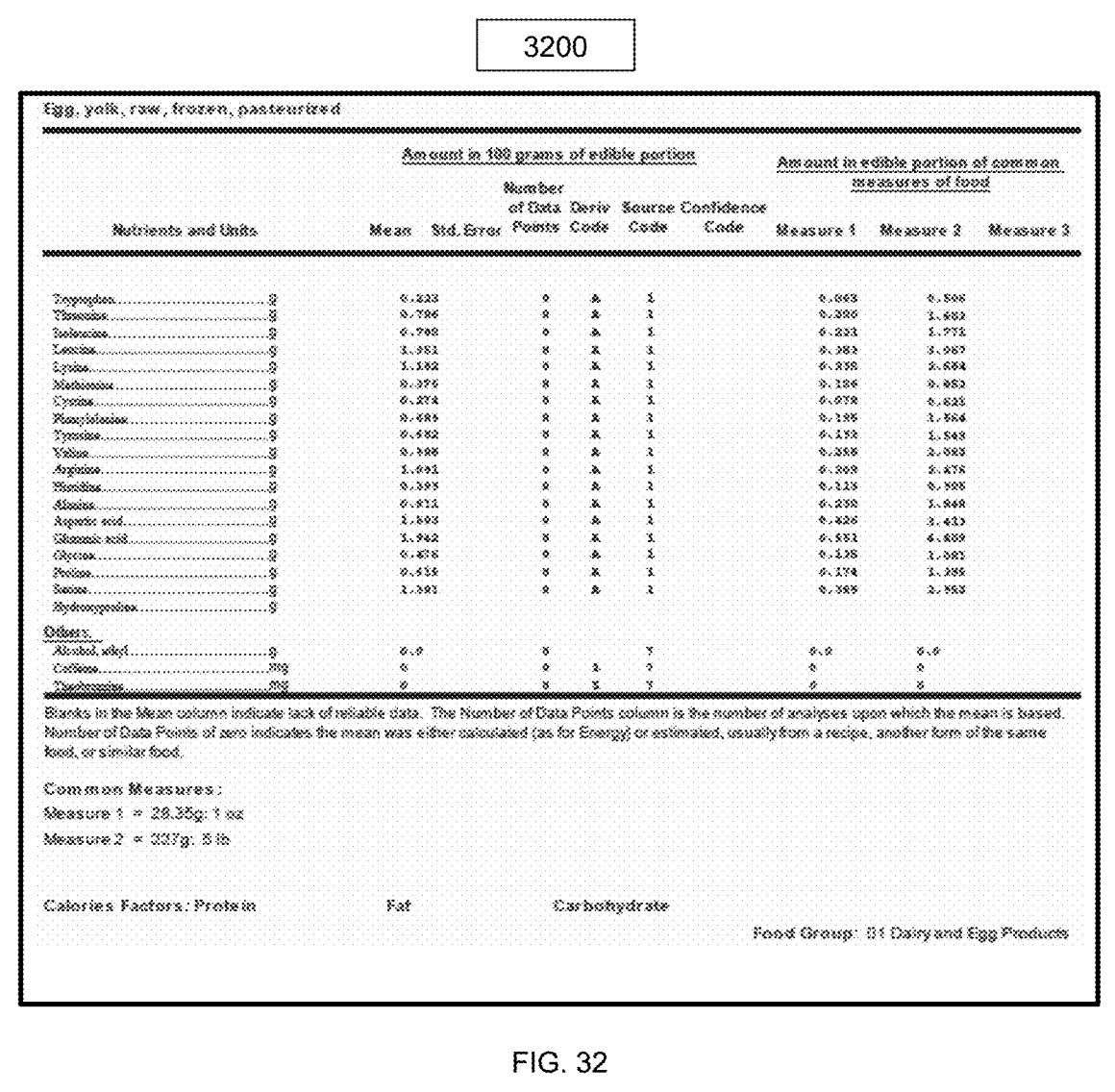

Egg, yolk, raw, frozen, pasteurized

| Nutrients and Units | Mean | Std. Error | Number of Data Points | Deriv Code | Source Code | Confidence Code | Measure 1 | Measure 2 | Measure 3 |
|---|---|---|---|---|---|---|---|---|---|
| | Amount in 100 grams of edible portion | | | | | | Amount in edible portion of common measures of food | | |
| Tryptophan.....g | 0.223 | | 0 | A | 1 | | 0.063 | 0.506 | |
| Threonine.....g | 0.796 | | 0 | A | 1 | | 0.226 | 1.807 | |
| Isoleucine.....g | 0.780 | | 0 | A | 1 | | 0.221 | 1.771 | |
| Leucine.....g | 1.361 | | 0 | A | 1 | | 0.386 | 3.089 | |
| Lysine.....g | 1.182 | | 0 | A | 1 | | 0.335 | 2.683 | |
| Methionine.....g | 0.376 | | 0 | A | 1 | | 0.106 | 0.852 | |
| Cystine.....g | 0.274 | | 0 | A | 1 | | 0.078 | 0.622 | |
| Phenylalanine.....g | 0.689 | | 0 | A | 1 | | 0.195 | 1.564 | |
| Tyrosine.....g | 0.682 | | 0 | A | 1 | | 0.193 | 1.548 | |
| Valine.....g | 0.898 | | 0 | A | 1 | | 0.255 | 2.038 | |
| Arginine.....g | 1.091 | | 0 | A | 1 | | 0.309 | 2.476 | |
| Histidine.....g | 0.395 | | 0 | A | 1 | | 0.112 | 0.896 | |
| Alanine.....g | 0.811 | | 0 | A | 1 | | 0.230 | 1.840 | |
| Aspartic acid.....g | 1.503 | | 0 | A | 1 | | 0.426 | 3.411 | |
| Glutamic acid.....g | 1.942 | | 0 | A | 1 | | 0.551 | 4.408 | |
| Glycine.....g | 0.476 | | 0 | A | 1 | | 0.135 | 1.081 | |
| Proline.....g | 0.615 | | 0 | A | 1 | | 0.174 | 1.396 | |
| Serine.....g | 1.301 | | 0 | A | 1 | | 0.369 | 2.953 | |
| Hydroxyproline.....g | | | | | | | | | |
| **Others:** | | | | | | | | | |
| Alcohol, ethyl.....g | 0.0 | | 0 | | 7 | | 0.0 | 0.0 | |
| Caffeine.....mg | 0 | | 0 | 1 | 7 | | 0 | 0 | |
| Theobromine.....mg | 0 | | 0 | 1 | 7 | | 0 | 0 | |

Blanks in the Mean column indicate lack of reliable data. The Number of Data Points column is the number of analyses upon which the mean is based. Number of Data Points of zero indicates the mean was either calculated (as for Energy) or estimated, usually from a recipe, another form of the same food, or similar food.

Common Measures:

Measure 1 = 28.35g: 1 oz

Measure 2 = 227g: .5 lb

Calories Factors: Protein Fat Carbohydrate

Food Group: 01 Dairy and Egg Products

SEARCH

3640

3670

Mushroom Lasagne 3680

Tomatoes, Mushrooms, tomato paste, thyme, red pepper,
Brown Rice Pasta, onions, olive oil, water, garlic, carrot INGREDIENTS
*Sauce* 3691

1 1/2 pound crimini mushrooms, roughly chopped
1/2 pound shitake mushrooms, roughly chopped
1 cup chopped onions
4 garlic cloves, chopped
1 - 6 oz can tomato paste
2 cups tomato sauce
1 - 28 oz can crushed tomatoes
1 cup distilled water
1/2 teaspoon red pepper flakes
*Lasagna*

3690

3650 ad Whole Foods Markets
*FB Score 4.2        cost: $17.49*
ad Walmart
*FB Score: 4        cost: $15.16*
ad Kroger
*FB Score 3.9        cost: $14.11*
Safeway
*FB Score 3.8        cost: $14.01*

3660 ad Olive Garden
*FB Score 3.8        cost: $28.01*
Little Joes
*FB Score 4.5        cost: $29.90*

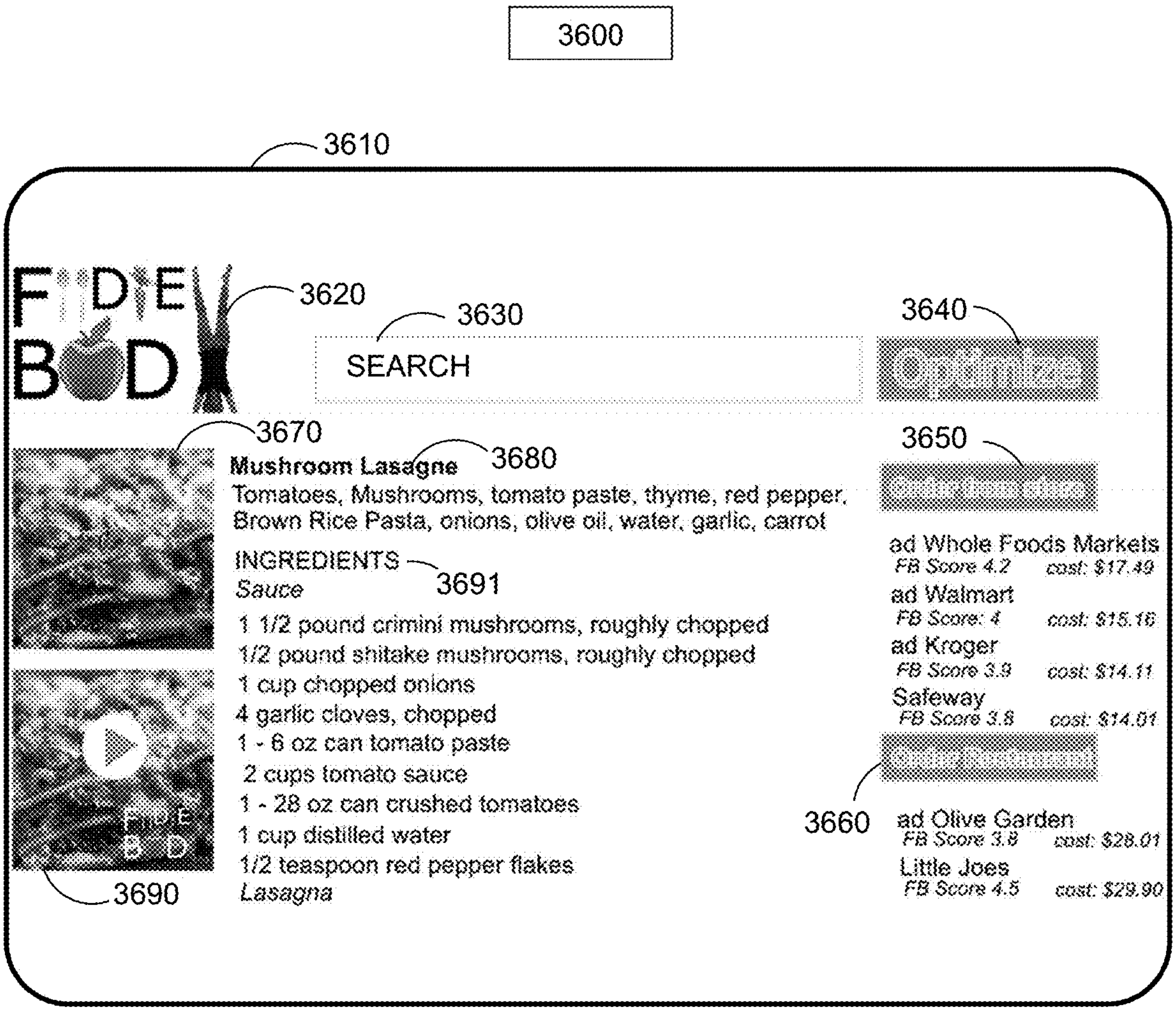

SEARCH

3740

3770

Check out now or Add to Cart to keep shopping                Quantity                3750

| | | |
|---|---|---|
| 2 pounds crimini mushrooms, roughly chopped | $3.99 | 1 |
| 1/2 pound shitake mushrooms, roughly chopped | $2.79 | 1 |
| 1 yellow organic onion | $0.89 | 1 |
| 1 Organic Garlic | $0.79 | 1 |
| 1 - 6 oz can tomato paste - Muir | $1.29 | 1 |
| 32 oz tomato sauce -Muir | $2.89 | 1 |
| 1 - 28 oz can crushed tomatoes - Muir | $2.49 | 1 |
| 1 gallon distilled water | $0.69 | 1 |
| Red Pepper Flakes 8 oz | $1.59 | 1 |
| Total | $17.41 | |

3760

3780

3790

3791

4300

4350

$$Biomarker = Beta\ Amyloid\ Plaques_i = 141.76 + 63.46X_i - 12.96X_i^2 + 0.93X_i^3$$

4360

$$Biomarker = hyperphosphoylated\ protein\ Tau_i = 11.76 + 66.6X_i - 1.21X_i^2 + 0.32X_i^3$$

4370

$$Biomarker = Neurofibrillary\ Tangles_i = 8.88 + 15.47X_i - 2.06X_i^2 + 0.10X_i^3$$

4380

$$Biomarker = ApoE3\ Beta\ Amyloid\ Plaques_i = 1.2 + \delta_0 + 63.46X_i - 12.96X_i^2 + 0.93X_i^3$$

4400
4410
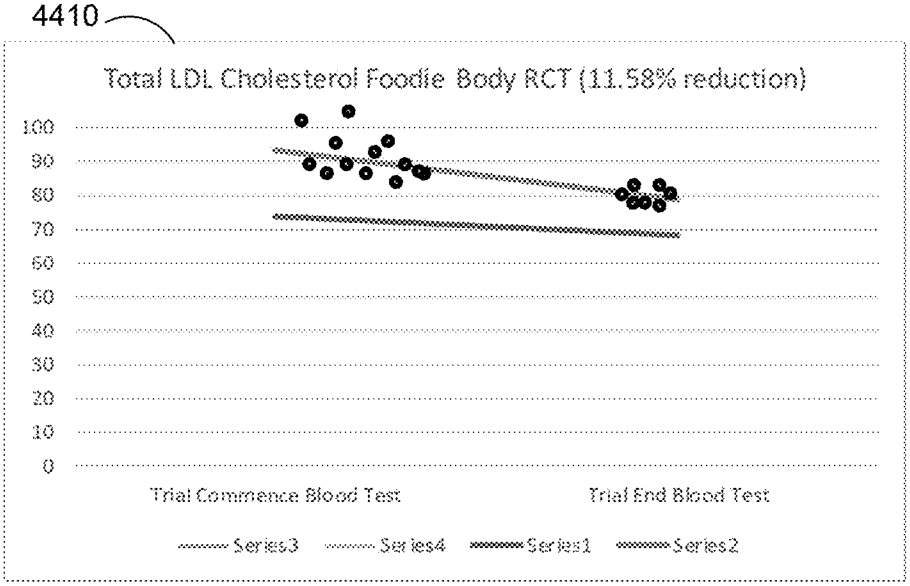
4411
$$Biomarker = Low\ Density\ Lipoprotein\ (LDL)_i = -1.2 lnX_i + 140 + \delta_0$$
4420
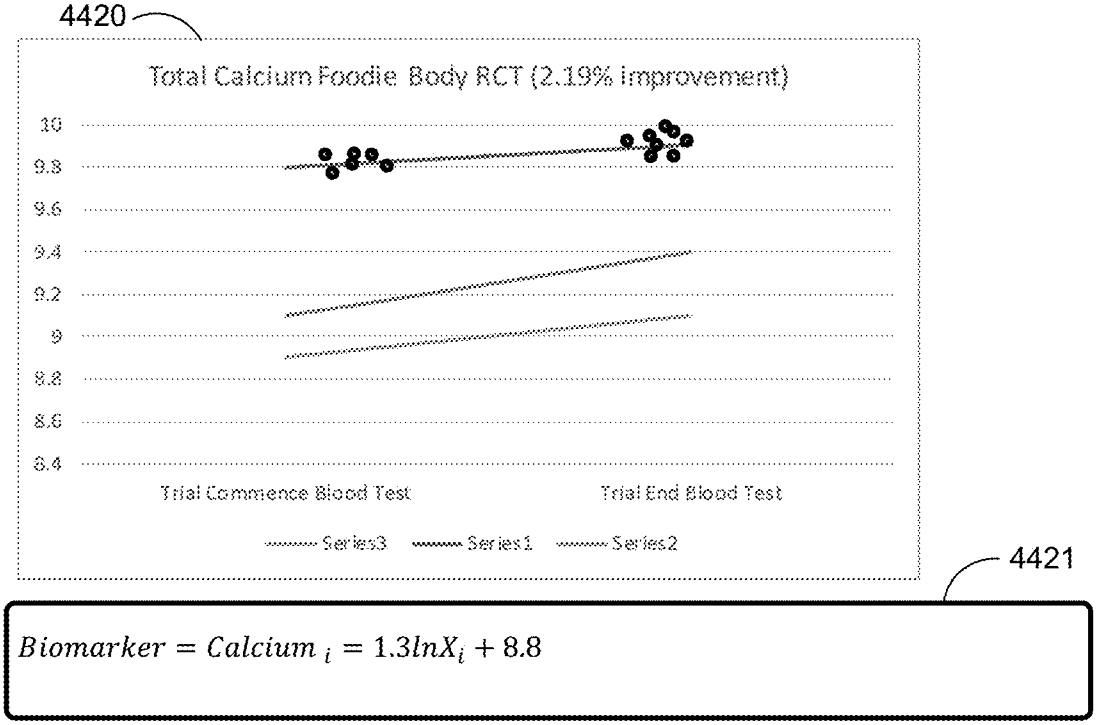
4421
$$Biomarker = Calcium_{\ i} = 1.3 lnX_i + 8.8$$
FIG. 44

4500

4510

4520

SYSTEM AND METHOD FOR DETERMINING OPTIMIZED FOOD COMBINATIONS

RELATED U.S. APPLICATION DATA

Continuation of U.S. patent application Ser. No. 15/484,059, "BLOOD AND SALIVA BIOMARKER OPTIMIZED FOOD CONSUMPTION AND DELIVERY WITH ARTIFICIAL INTELLIGENCE," filed Apr. 10, 2017.

BACKGROUND OF THE INVENTION

Field of the Invention

Implementations of a method and system to search online for food and beverage utilizing blood, saliva, hair, urine, stool, fingernail, height, weight and skin sampling analysis to optimize personal food nutrition, health, variety, ethnicity, flavors, ratings and delivery using iterative machine learning models (linear and non-linear optimization in neural networks) and data mining in the context of assigning individual food, recipes and food combination (including beverages) scores to nodes in a linked database containing nutrition data, food and beverage combination nutrition data, the world wide web or any other hypermedia database. The score assigned to a food or food combination not only considers the absolute nutrition value of the food or food combination (including beverages) and food combination ratings, but also the biomarker chemistry of the user, water usage and carbon footprint data in context of an optimization equation. Therefore, the score and search method is personalized for each user's biomarker fingerprint. The user may turn on or off various constraints in the optimization equation associated with their profile. As we write this method and system, it is well known to someone skilled in the art that if a person utilizes a search engine for food or beverages, the results that come back are imprecise with great amounts of conflicting information. A typical search for "Italian Food" lists Italian restaurants near an users area that are influenced by advertising dollars and mention nothing of health or the efficiency of the food which is produced. Searches often consider the users location proximity to a food and beverage establishment or previously favored search data from the user, but the search data certainly is not scored for quantified health effect or how the food or beverage is suited to a user's biomarker fingerprint. The effect of food and beverages on the body however are precise and very measurable. Further compounding the problem is that each person is unique and the search engines have no current method of understanding the biomarker fingerprints of users when completing a search request. Search engine precision and information retrieval systems are traditionally judged by their precision and recall, but anyone skilled in the art would know all current search engines are incapable of addressing the aforementioned problem. Further it may be argued that current search engines are pointing people to sub-optimal healthy food and beverage choices based on advertising promotional dollars which contribute towards chronic disease such as diabetes, cancer, arthritis, heart disease, obesity, attention deficit disorders, cognitive impairment and many other diseases which are caused primarily by diet. Search for food and beverage also is heavily influenced by popularity rankings or back-linked references which have little or nothing to do with health or nutrition for a specified user. Users of search for diets are often frustrated because most diet plans are stated as "one size fits all plans" where a person's specific blood, saliva, hair, urine, stool, fingernail, height, weight and skin is not considered in the formation of the diet unless one were to spend an uneconomic amount of money to go to a personalized nutritionist which would not have such systems as are documented in the novel invention. Persons skilled in the art also know that large databases such as the world wide web also have many low quality documents, recipes and food combinations which do not consider the health, preferences or biomarker fingerprint of the user. Simply stated, food recipe chemistry has not been mathematically linked to blood, saliva, hair, urine, stool, fingernail, height, weight and skin sampling analysis to optimize personal food nutrition in any searchable food or beverage database. As a result, searches typically return thousands of irrelevant or even blatantly inaccurate data on food and beverage nutrition and food combinations with respect to a user's plurality of biomarkers. In addition to the aforementioned problems there is a tremendous amount of food waste because people do not have easy access to a method or system to analyze for them what their body actually needs. Western Civilization wastes nearly 40% of produced and harvested food. The Center for Disease Control and Prevention sites 36.5% of adults in the West suffer from obesity. The estimated annual medical cost of obesity in the U.S. was $147 Billion in 2008 U.S. dollars. The medical costs of the aforementioned obese individuals is $1,429 higher than for those of normal weight. In March 2019, Amazon, Berkshire Hathaway and JP Morgan formed a joint venture named Haven to take exploding health care costs. Warren Buffet calls exorbitant health care costs the tapeworm of the economy. Rising health care costs may represent as much as 18% of GDP which reduces corporate profits and if left unchecked, the failure of addressing root causes of health will cause most companies to go bankrupt and this will cause enormous job loss. Unchecked health care costs and inefficiencies also place the economy at a tremendous disadvantage in terms of outright costs and lost productivity. While western developed markets show quantitative data that points to excess food and obesity, developing nations still suffer from stunted growth, lack of nutrition, agricultural shortfalls and lack of stability in food supply. Further, the introduction of Western diets to developing countries has led to rapid increases in obesity rates among developing world population countries. There are tremendous opportunities to re-allocate nutrition using math, science and technology to meet the world's needs without necessarily producing more, but rather improving efficiency and utilization rates. The implementation of the method allows for unbiased measure of nutrition and body chemistry through blood, saliva, hair, urine, stool, fingernail, height, weight and skin sampling analysis and computerized systems where machine learning based optimization techniques for improvement of human condition and health are utilized. No two people are alike in our unique body chemistry and yet we ingest food to serve our unique chemistries without unbiased analysis that is at our fingertips with the proposed method and system. The implementation of the method uses biomarkers and chemistry in blood, saliva, hair, urine, stool, fingernail, height, weight and skin sampling analysis to determine optimal personal food consumption, ingredient weighting, health, variety, flavoring, style, ethnicity, ratings, nutrition, water use and carbon footprint and delivery which does not rely on self-reporting problems of inaccurate recall or reluctance to give a candid report. The biomarker analysis provides for an unbiased yet statistically accurate history which is stable and more reliable than self-reporting. Implementations of the various methods to create optimal food nutrition, health, ingredient weighting, variety, ethnicity, ratings, flavor and delivery also may reduce food consumption by 5% to 70% depending on the variables and the individual user. The method may also provide unbiased ordering and search information that is based on math and science from the user to reduce food waste in grocery stores by as much as 5% to 40% but not limited to those levels of reduction. Reduced food waste lowers food cost globally, reduces fossil fuel consumption and provides more resources for those who have very little resources or not enough resources. The linear and non-linear optimization equations allow for much more useful and efficient food and beverage search. Implementation of various methods of optimizing personal food and beverage search for blood, saliva, hair, urine, stool, fingernail, height, weight and skin sampling analysis also provides optimal healthy food intake which improves the overall quality of a society. Implementations of methods to optimize food intake for blood, saliva, hair, urine, stool, fingernail, height, weight and skin sampling analysis also reduces mood swings and productivity losses caused by excessive variation in blood chemistry. Lower amounts of mood swings due to lower variation in biomarker chemistry contributes positively to higher human productivity and lower amounts of societal stress. Athletic, scholastic, work, performing art or human endeavor performance can also vary by 10% to 50% depending on various biomarker swings due to inadequate nutrition. Improving search for food and beverage may dramatically improve athletic, scholastic, work, performing art or human endeavor performance by helping users find the foods and beverage their body needs in a robust, scalable, mathematic and scientific manner. For the purpose of efficiency in this document we will interchangeably use the term “User” and “Foodie”.

Description of the Related Art

The following descriptions and examples are not admitted to be prior art by virtue of their inclusion within this section.

The current implementations of methods to use biomarkers, blood, saliva, hair, urine, stool, fingernail, height, weight and skin testing focus on treating specific conditions and diagnosing predispositions but they are not used to optimize human health or search using algorithms (systems of linear and non-linear optimization equations) and artificial intelligence neural networks to provide iterative system feedback from a user to then compare utility maximization equation systems over blood, saliva, hair, urine, stool, fingernail, height, weight and skin sampling analysis variables subject to a plurality of constraints such as budget, flavor preferences, ethnic preferences, ratings, water use, carbon footprint and nutrient matching to biomarker chemistry over a computer system where users may have a simple and elegant method to search, order raw or cooked food and beverage over the application and arrange for delivery or pickup, yet harness the power of machine learning techniques and non-linear calculus maximization equations and neural networks to optimize their biomarker chemistry and health in the background. Further, the system recommends and ranks various food options based on non-linear systems of vectors, neural networks and optimization formulas to optimize on all of user’s blood, saliva, hair, urine, stool, fingernail, height, weight, skin, preference, ratings, health, ingredient weights, variety, flavoring, style, ethnicity, nutrition, water use, carbon footprint and delivery.

Implementations of methods have been made in systems that provide the identification of a biomarker for the analysis of certain conditions, but the implementations do not provide a solution for the user to have an integrated search approach to their overall health and diet with feedback from a plurality of machine learning models with neural network algorithms or non-linear calculus maximization equations designed to optimize food and beverage intake based on analysis of the user’s blood, saliva, hair, urine, stool, fingernail, height, weight and skin:

1) U.S. Pat. No. 6,285,999 issued Sep. 4, 2001 to Lawrence Page covers a methodology for node ranking in a linked database. Very clearly the implementation, method and system node rank very large databases using a computer implemented scoring method for linked documents and documents. The scoring method considers backlinks scoring of backlinks to rate the relevance of documents to a given user’s search term. First, the scoring system may be manipulated because user’s may create backlinks for their own pages or document files which artificially increases their score or rank. Second the method does not consider the possibility of an objective unbiased measurement method considering blood, saliva, hair, urine, stool, fingernail, height, weight and skin, preference, ratings, health, ingredient weights, variety, flavoring, style, ethnicity, water use, carbon footprint, nutrition and delivery in the optimization ranking algorithm. Accordingly, a diabetic user would potentially be given the same search request result if searching for “Italian Food” as a non-diabetic. Similarly, the search may also provide a similar search result for “Italian Food” as someone with LDL Cholesterol of 120 as someone with LDL Cholesterol of 60. Therefore, the search algorithm method contributed by Page may result in arguably contributing further to diabetic or heart disease in society and leading to higher levels of disease and therefore cost to society. Backlink scoring algorithms have no understanding of a person’s nutrition, water use, carbon footprint or health level. The system and method proposed by Page would be incapable of ranking a recipe, web page, food combination or any ingestible food or beverage considering biometric attributes of a user. The system and method may be capable of finding search results of “Italian food for diabetics”, but once again, there is such a range of levels of diabetic disease, that the results are largely unusable and unhelpful. The results of the search are not personalized to a user’s blood, saliva, hair, urine, stool, fingernail, height, weight and skin, preference, ratings, health, ingredient weights, variety, flavoring, style, ethnicity, water use, carbon footprint or nutrition chemistry and do not consider health or more specifically user health. Lastly a more complete discussion of the economics of food also must consider the resources used to produce the food. The proposed system and method may consider not only water usage to obtain nutrients but also the carbon footprint in the equation constraints. Because this information has traditionally been obscure or hard to come by, typical user’s do not consider the information in current search results on traditional search engines for large databases. The proposed invention solves the aforementioned dilemmas.

2) U.S. Pat. No. 7,680,690 issued Mar. 16, 2010 to Anthony B. Catalano covers a methodology for customers seeking to purchase a meal from a food service vendor such as a restaurant, a cafeteria, or a vending machine, by ordering a food preparation based upon menu-selection. In addition to receiving ordered food, customers receive suggestions for optionally modifying their food orders based upon nutritional benefits and other criteria. Either during real-time customer-ordering or during post-ordering, a food-service vendor presents a customer suggestions specific to a pending tentative or completed order, wherein the customer may enjoy purported nutritional benefits by electing to follow these suggestions and thereby modify the tentative order into a corresponding completed order. The preferred embodiment contemplates a restaurant environment in which customers typically approach a food-ordering counter and interface with both a menu display and with order-taking personnel. Other embodiments implicate kiosks, vending machines, remote access devices, and locally and remotely-accessed networked computers, wherein customers interact with automated computer-driven devices instead of or in addition to wait-staff or other food service personnel. The limitation and disadvantages of the prior art which seeks to have the user continually modify food choices is that the solution has no direct tie to the user's personal blood, saliva, hair, urine, stool, fingernail, height, weight and skin, preference, ratings, health, ingredient weights, variety, flavoring, style, ethnicity, nutrition chemistry in the calculation, the prior art does not address a full composite of food attributes, the prior art system and method does not consider that individual blood, saliva, hair, urine, stool, fingernail, height, weight and skin, preference, ratings, health, ingredient weights, variety, flavoring, style, ethnicity, water use, carbon footprint and nutrition chemistry reacts differently to the plurality of menu ingredients which renders the solution very limited in scope and use. Further, self reporting problems are magnified by systems and methods which do not calibrate from independent test lab results. By contrast, the prior art method of a computerized database of anonymous customer preference information is fundamentally different from the proposed method of a custom blood, saliva, hair, urine, stool, fingernail, height, weight and skin, preference, ratings, health, ingredient weights, variety, flavoring, style, ethnicity, nutrition water use and carbon footprint database that may provide specific calculations for each user. Also by contrast, the proposed method considers each food selection considering a specific mathematic optimization equation of the relationship to blood, saliva, hair, urine, stool, fingernail, height, weight and skin, preference, ratings, health, ingredient weights, variety, flavoring, style, ethnicity, water use, carbon footprint and nutrition chemistry of the specific user. Also by contrast, the proposed method has optimized the selection alternatives in advance of the order specifically for blood, saliva, hair, urine, stool, fingernail, height, weight and skin, preference, ratings, health, ingredient weights, variety, flavoring, style, ethnicity, water use, carbon footprint and nutrition chemistry whereas the aforementioned prior art method modifies a user's selection to pick healthier ingredients but does not consider that each user has fundamentally different blood, saliva, hair, urine, stool, fingernail, height, weight and skin, preference, ratings, health, ingredient weights, variety, flavoring, style, ethnicity, nutrition chemistry, the process is fundamentally different. Additionally by contrast, the proposed method does not substitute food ordering based on healthier ingredients like the prior art, but recommends foods based on their specific relationship to the user's blood, saliva, hair, urine, stool, fingernail, height, weight and skin, preference, ratings, health, ingredient weights, variety, flavoring, style, ethnicity, water usage, carbon footprint and nutrition chemistry. The prior art quantifies nutrition in a linear point system which is inadequate to describe the non-linear relationship between food and beverage nutrition and blood, saliva, hair, urine, stool, fingernail, height, weight and skin, preference, ratings, health, ingredient weights, variety, flavoring, style, ethnicity, water usage, carbon footprint and nutrition chemistry. The prior art does not consider the non-linear nature of the nutrition to health equation and therefore also leads to a mathematically inferior result. Proof of linear equations yielding inferior solutions to non-linear equations in describing a dynamic problem such as nutrition and health is standard knowledge to anyone skilled in the art of dynamic equation modeling and non-linear equation modeling. To anyone skilled in the art of applied econometrics we cite the Journal of Applied Econometrics (J. Appl. Econ. 20; 891-910 (2005)), Fernandez-Villaverde and Rubio-Ramirez who provide proof by counterexample that even in a linear case, non-linear monte carlo simulation yields superior weightings and results. Accordingly the premise and method of the prior art are completely unique and fundamentally different from the proposed method and system.

3) U.S. Pat. Nos. 6,618,062 and 6,646,659 issued Sep. 9, 2003 to Brown, et al. discloses a method, system and program for specifying an electronic food menu with food preferences from a universally accessible database. The prior art relates to a method, system and program for specifying an electronic menu for a particular customer from food preferences received via a person integrated circuit. The technology taught in Brown covers a method, system and program retrieves unique customer preferences based upon a unique customer key which then improves the efficiency of special requests on a menu in the food industry. By contrast, the proposed method and system is solely based on preferences which are input by the user and these preferences may or may not relate to blood, saliva, hair, urine, stool, fingernail, height, weight and skin, preference, ratings, health, ingredient weights, variety, flavoring, style, ethnicity, nutrition chemistry. By contrast, the proposed novel method and system uses an objective measurement of data from a sample of blood, saliva, hair, urine, stool, fingernail, height, weight and skin, preference, ratings, health, ingredient weights, variety, flavoring, style, ethnicity, nutrition chemistry which is then utilized in a no-linear mathematic optimization equation to move the user's biomarker chemistry from its current state to a desired target range. Accordingly the premise and method of the prior art are completely unique and fundamentally different from the proposed method and system.

4) U.S. Pat. No. 6,434,530 issued Aug. 13, 2002 to Sloane et al. discloses an interactive system adapted for use in a shopping venue to provide supplemental information related to an article available for selection by shoppers in a shopping venue. The prior art provides a method and system of retrieving helpful data for a consumer to guide their decision process. The prior art describes a method that shows a user that a can of tomato sauce is on sale, then it helps to determine a sort for the best price, lower amount of salt, a name brand, a store brand while referencing the users prior preferences from a database. While the system is interactive and intelligent, the underlying algorithms, purpose and content are different from the proposed method. By contrast, the proposed method and system directly utilizes a blood, saliva, hair, urine, stool, fingernail, height, weight and skin, preference, ratings, health, ingredient weights, variety, flavoring, style, ethnicity, nutrition chemistry sample from the user to then optimize hundreds of combinations and permutations of groupings of ingredients and recipes a user may enjoy that are selected upon reference for the users consumption, health, variety, flavoring, style, nutrition and delivery which does not rely on a single diagnostic test or self-reporting problems because of independent blood and saliva tests subject to the constraints of income, price, and location.

5) U.S. Pat. No. 7,090,638 issued Aug. 15, 2006 to Edward Vidgen covers a dietary planning system that receives the personal characteristics and food preferences for a user. The prior art reviews personal characteristics such as a desired physiological rate of change for the individual and develops optimal dietary menus that maximize the palatability of the menu while satisfying dietary constraints that may relate to a user's preferences. The prior art personal information database includes an individuals sex, age, weight and exercise level. The prior art requests the user to input a desired physiological rate of change such as one pound per week and the user also inputs his or her energy expenditure by answering questions about the users activity levels. The equation of the prior art uses a simple formula to target as an example one pound of weight loss per week as a requirement to produce a diet that reduces kilocalories by 500 units a day. The prior art personal information database does not include biomarker data such as the chemistry of blood, urine, saliva, stool, fingernails, hair or other biological samples. The prior art equations and methods have no consideration of correlation of either the dependent or independent variables rendering the equations as unusable due to the fact that the parameters of physiology and dietary inputs all have relative degrees of correlation amongst themselves, yet the formulas do not attempt to process these factors. The prior art also does not recursively or through regression determine food weights based on multiperiod biometric samples which calibrate weights based on biometric relationships and correlations. The prior art labels equations that weight various ingredients that are subject to a kilocalorie inequality or a protein weight inequality however the teaching does not make clear any actual optimization equation that is valid so it is unclear that the system is optimizing anything other than giving weights that fall under a constraint which does not qualify as optimization and it does not handle potential non-linear relationships of food chemistry and blood chemistry or the chemistry of saliva, hair, urine, stool, fingernail, height, weight and skin. To anyone with basic skill in the art, there would be basic mathematic principles that are being violated as sensitivity analysis of linear programming has been widely studied. In the presence of correlation, which is obvious in the parameter selection for both independent and dependent variables, it may be proven false by single empirical counter-example the method of linear programming in the prior art yielding results that are mathematically incorrect or inferior and therefore not optimal. The prior art utility function is specifically the weight of a given food multiplied by a palatability ranking which yields a total palatability of a combination of foods without any regard for how the food effects the chemistry of the users body and is therefore a completely disparate art from the novel invention. The prior art constraint functions place constraints on such items as dietary fiber whereas the novel art is optimizing around biomarkers which again are completely disparate art methods and underlying functions. The prior art uses no form of linear or non-linear regression to determine expected value rankings of food or beverage on a user's blood, saliva, hair urine, stool, fingernail, height, weight or skin prior to optimizing weights. The prior art uses no multiperiod (time series) biomarker sampling dependent method and food logging system to determine the biomarker sensitivities to various foods and beverages over a plurality of time metrics. The prior art system does not discuss or handle any relationship of the user's blood or saliva chemistry or the chemistry of saliva, hair, urine, stool, fingernail, height, weight and skin with respect to various food ingredients which make the prior art a closed system without dynamic updates from biomarkers unlike the novel art.

6) U.S. Pat. No. 9,410,963 issued Aug. 9, 2016 to Nestec S. A. covers the use of a biomarker to diagnose the likelihood to resist diet induced weight gain and the susceptibility of diet induced weight gain. The method is to determine the level of hexanoylglycine relative to a predetermined reference to determine the likelihood of resisting high fat diet induced weight gain. The proposed method is diagnostic, not prescriptive. The method attempts to diagnose predisposition of likelihood to reduce diet induced weight gain and likelihood to resist high fat diet induced weight gain. By contrast the proposed independent methods and systems form optimization algorithms (which are linear and non-linear systems of vectors) on individual food ingredients and the combinations thereof to maximize nutrition of a user's consumption, health, variety, flavoring, style, nutrition and delivery which does not rely on a single diagnostic test or self-reporting problems because of independent blood, saliva, urine, stool, fingernail, hair or other biomarker tests subject to the constraints of income, price, and location. Further the proposed method and system is fully integrated to allow a user to have their meal selection with as few as three clicks on a graphical user interface while the computer based optimization calculations of linear and non-linear vectors alongside optimization maximization equations have solved for optimal healthy choices.

7) U.S. Pat. No. 6,663,564 issued Dec. 16, 2003 to Weight Watchers Limited covers a process for controlling body weight in which a selection of food servings is based on a calculated point value and a range of allotted daily points which is adjusted for weight change. The calculated point value is a function of measured calories, total fat and dietary fiber. A range of points allotted per day may be calculated based on current body weight, caloric reduction to be achieved, physical activity level and physical activity duration. While the process and method uses a math formula to count kilocalories, fiber, and fat, the equation is linear and therefore does not maximize for overall nutrition considering a more realistic but larger set of variables and the non-linear nature of the real life nutrition equation and associated correlations. Further the method is not customized by blood, saliva, urine, stool, fingernail and hair chemistry per each user. By contrast the proposed independent methods and systems form optimization algorithms (which are linear and non-linear systems of vectors) on individual food ingredients and the combinations thereof to maximize nutrition of a user's consumption, health, variety, flavoring, style, nutrition and delivery which does not rely on a single diagnostic test or self-reporting problems because of independent blood, saliva, stool, urine, hair, fingernail chemistry tests subject to the constraints of income, price, and location. Further the proposed method and system is fully integrated to allow a user to have their meal selection with as few as three clicks on a graphical user interface while the computer based optimization calculations of linear and non-linear vectors alongside optimization maximization equations have solved for optimal healthy choices in the background of the simple graphical user interface.

8) U.S. Pat. No. 5,412,560 issued May 2, 1995 to Dine Systems, Inc. covers a process for evaluating an individual's food choices based upon selected factors and dietary guidelines. The invention analyzes the food an individual eats and determines certain predictor and follower nutrients that will give rise to an assessment of how a person's diet matches with various dietary guidelines established by governmental and/or other entities. The invention provides the results of the analysis to the individual complete with messages regarding over or under consumption of key nutrients so that the individual can correct the diet thereby resulting in better eating habits. The invention also gives the individual a "score" by which the person can immediately assess how well he or she is doing with respect to the various guidelines. The higher the number the better the diet. Further the method is not customized by blood, saliva, urine, stool, hair, or fingernail or other biomarker chemistry per each user. By contrast the proposed independent methods and systems form optimization algorithms (which are linear and non-linear systems of vectors) on individual food ingredients and the combinations thereof to maximize nutrition of a user's consumption, health, variety, flavoring, style, nutrition and delivery which does not rely on a single diagnostic test or self-reporting problems because of independent blood, saliva, urine, stool, hair or fingernail chemistry tests subject to the constraints of income, price, and location. Further, the proposed system and method is able to log each meal ingredient because the system has the ability to order the food raw or prepared and deliver the food to the user. The proposed system provides an integrated approach to holistic nutrition and also provides food item intelligence to take a picture of a meal and then log into the database food that was not ordered or designed on the system. Further the proposed method and system is fully integrated to allow a user to have their meal selection with as few as three clicks on a graphical user interface while the computer based optimization calculations of linear and non-linear vectors alongside optimization maximization equations have solved for optimal healthy choices in the background of the simple graphical user interface.

9) U.S. Pat. No. 9,528,972 issued Dec. 27, 2016 to Eugenio Minvielle covers nutritional substance systems and methods are disclosed enabling the tracking and communication of changes in nutritional, organoleptic, and aesthetic values of nutritional substances, and further enabling the adaptive storage and adaptive conditioning of nutritional substances. The system logs changes in nutrition as heat and cooling changes the nutritional values. Further the method is not customized by blood, saliva, urine, stool, fingernail, hair or other biomarker chemistry per each user. By contrast the proposed independent methods and systems form optimization algorithms (which are linear and non-linear systems of vectors) on individual food ingredients and the combinations thereof to maximize nutrition of a user's consumption, health, variety, flavoring, style, nutrition and delivery which does not rely on a single diagnostic test or self-reporting problems because of independent blood and saliva tests subject to the constraints of income, price, and location. Further, the proposed system and method is able to log each meal ingredient because the system has the ability to order the food raw or prepared and deliver the food to the user. The proposed system provides an integrated approach to holistic nutrition and also provides food item intelligence to take a picture of a meal and then log into the database food that was not ordered or designed on the system. Further, the system recommends various food options based on linear and non-linear systems of vectors and optimization formulas to optimize on all of user preference, health, variety, flavoring, style, ethnicity, nutrition and delivery. Further the proposed method and system is fully integrated to allow a user to have their meal selection with as few as three clicks on a graphical user interface while the computer based optimization calculations of non-linear vectors alongside optimization maximization equations have solved for optimal healthy choices in the background of the simple graphical user interface.

10) U.S. Pat. No. 8,249,946 issued Aug. 21, 2012 to General Mills, Inc. covers a system and method for selecting, ordering and distributing customized food products is disclosed. In one embodiment, the method is a computer-implemented method comprising viewing a list of additives for creating a customized food product, selecting one or more additives from the list of additives to create the customized food product, and transmitting a request to purchase the customized food product, which is then distributed to the consumer. By communicating with the manufacturer as to personal needs and desires pertaining to health, activity level, organoleptic preferences and so forth, the consumer can now develop and order a customized food product to suit his or her particular tastes, using a real-time interactive communication link. Further the method is not customized by blood, saliva, urine, stool, hair, fingernail or other biomarker chemistry per each user. By contrast the proposed independent methods and systems form optimization algorithms (which are linear and non-linear systems of vectors) on individual food ingredients and the combinations thereof to maximize nutrition of a user's consumption, health, variety, flavoring, style, nutrition and delivery which does not rely on a single diagnostic test or self-reporting problems because of independent blood and saliva tests subject to the constraints of income, price, and location. Further, the proposed system and method is able to log each meal ingredient because the system has the ability to order the food raw or prepared and deliver the food to the user. The proposed system provides an integrated approach to holistic nutrition and also provides food item intelligence to take a picture of a meal and then log into the database food that was not ordered or designed on the system. Further, the system recommends various food options based on linear and non-linear systems of vectors and optimization formulas to optimize on all of user preference, health, variety, flavoring, style, ethnicity, nutrition and delivery. Further the proposed method and system is fully integrated to allow a user to have their meal selection with as few as three clicks on a graphical user interface while the computer based optimization calculations of non-linear vectors alongside optimization maximization equations have solved for optimal healthy choices in the background of the simple graphical user interface.

11) U.S. Pat. No. 8,920,175 issued Dec. 30, 2014 to Thrive 365 International, Inc. covers a method is provided for assigning a relative score number to foods. Assignment of a relative score number to foods allows consumers to select foods that will provide a desirable diet. Equations are provided which are effective to yield a predicted raw score based on measured characteristics. The predicted raw score statistically correlates to a raw score that would be determined by an actual panel. The predicted raw scores are further processed to provide a relative score number that can be easily tracked by a consumer. Further the method is not customized by blood, saliva, urine, stool, hair, fingernail or other biomarker chemistry per each user. By contrast the proposed independent methods and systems form optimization algorithms (which are linear and non-linear systems of vectors) on individual food ingredients and the combinations thereof to maximize nutrition of a user's consumption, health, variety, flavoring, style, nutrition and delivery which does not rely on a single diagnostic test or self-reporting problems because of independent blood, saliva, fingernail, hair, stool, urine or other biomarker tests subject to the constraints of income, price, and location. Further, the proposed system and method is able to log each meal ingredient because the system has the ability to order the food raw or prepared and deliver the food to the user. The proposed system provides an integrated approach to holistic nutrition and also provides food item intelligence to take a picture of a meal and then log into the database food that was not ordered or designed on the system. Further, the system recommends various food options based on linear and non-linear systems of vectors and optimization formulas to optimize on all of user preference, health, variety, flavoring, style, ethnicity, nutrition and delivery. Further the proposed method and system is fully integrated to allow a user to have their meal selection with as few as three clicks on a graphical user interface while the computer based optimization calculations of non-linear vectors alongside optimization maximization equations have solved for optimal healthy choices in the background of the simple graphical user interface.

12) U.S. Patent Application No. 2014/0220516 published Aug. 7, 2014 by Marshall et al. discloses a system and method for food items with nutritional insight analysis using big data. Specifically the claims outline a user profile which is based on name, age, gender, height, weight, activity level and at least one health condition then comparing recipes in an iterative process. The dependent claim 5 then connects a user to a registered dietitian which evaluates health guidelines and customization. The overall method and system of the prior art is completely disparate from the novel invention as the method and software perform no analysis on a users blood, saliva, fingernail, hair, urine, stool or other biomarker characteristics and chemistry to quantify a change in the user or optimize any diet based on method calculations. Further, any analysis of a users health condition is completed outside of the scope of the prior method art. Accordingly, the method claims are not comparable.

13) U.S. Pat. No. 9,558,515 issued Jan. 31, 2017 to Babu et al. discloses a method for recommending a food item to a registered customer comprising a group of one or more members accessing a shopping cart for a registered user; accessing a nutritional profile for the registered customer and making a determination if the nutritional content of the items in the shopping cart meet the nutritional profile of the user and if not, identifying an additional food item that satisfies at least in part on the customer nutritional profile. The method claim states the method calculates a cumulative nutritional content to determine if the nutritional content of two or more food items fails to satisfy at least one nutritional requirement of the registered customer, then identifying another item satisfies at least one nutritional requirement of the registered user and recommending the additional item to the user. Anyone skilled in the art of optimization would know that the claimed method yields answers which are not optimal and therefore inferior and useless for comprehensive health. Additionally, the method and patent claims no formula which questions even if a patent should have been issued for the subject matter claiming calculations. No ranking mechanisms are mentioned or named which proves to anyone skilled in the art that the answers such a system would yield are not complete, useful or efficient. If one were to conclude the aforementioned method term of cumulative nutrition were to imply the calculation of addition, the effect of food on health is not linear and uncorrelated and therefore addition yields inferior or useless calculations. To prove a method useless or inferior, one must provide a counterexample. To anyone skilled in the art of applied econometrics we cite the Journal of Applied Econometrics (J. Appl. Econ. 20; 891-910 (2005)), Fernandez-Villaverde and Rubio-Ramirez who provide proof by counterexample that even in a linear case, non-linear monte carlo simulation yields superior weightings and results. First, both for simulated and for real data, the sequential Monte Carlo filter delivers a substantially better fit of the model to the data as measured by the marginal likelihood. This is true even for a nearly linear case. Second, the differences in terms of point estimates, although relatively small in absolute values, have important effects on the moments of the model. We conclude through mathematical proof that the non-linear filter is a superior procedure for taking models to the data. Further anyone skilled in the art of health would know a cumulative nutrition calculation is not capable of providing the shortest route or most efficient mapping (in other words, health is not a linear problem, but rather non-linear and correlated). The method may claim a route of eating and food selection, but the method is not optimal, rigorous or most efficient. Accordingly, due to the nature of the problem of mapping food nutrition to human health profiles, the former method is clearly inferior and distinct to the proposed method which considers first multi dimensions (more than one nutrition constraint) rather than a single dimension (cumulative nutrition constraint) and the non-linear optimization nature of the problem at hand. A system or method included in the prior art would lead a user to inferior results. Also of note, the prior art performs no time series analysis of the rate of change of a particular user or user group relative to their blood, saliva, urine, hair, stool or fingernail response to a change in diet. Without time series analysis of biomarker chemistry changes to food changes any ranking or ordering system would be producing results which would be spurious and not accurate.

SUMMARY

The claimed subject matter is not limited to implementations that solve any or all of the noted disadvantages. Further, the summary section is provided to introduce a selection of concepts in a simplified form that are further described below in the detailed description section. The summary section is not intended to identify key features or essential features of the claimed subject matter, nor is it intended to be used to limit the scope of the claimed subject matter.

An independent method and system to node rank recipe, food, prepared foods based on optimization algorithms (which are linear and non-linear systems of vectors) on individual food ingredients and the combinations thereof in recipe format for an order of food from a raw food distribution point or a prepared food distribution point to maximize nutrition of a user's consumption, health, variety, flavoring, style, ethnicity, nutrition and delivery which does not rely on a single diagnostic test or self-reporting problems because of independent blood, saliva, hair, urine, stool, fingernail, height, weight and skin sampling analysis subject to further constraints of income, price, and location. Further, the proposed system and method is able to log each meal ingredient because the system has the ability to order the food raw or prepared and deliver the food to the user or allow the user to pick up the food at a food distribution point. The proposed system provides an integrated approach to holistic nutrition and also provides food item intelligence to take a picture of a meal and then log into the database food that was not ordered or designed on the system. Further, the system recommends various food options based on linear and non-linear systems of vectors and optimization formulas to optimize on all of user preference, blood, saliva, hair, urine, stool, fingernail, height, weight and skin sampling analysis chemistry, health, variety, flavoring, style, ethnicity, nutrition and delivery among other variables but not limited to the aforementioned variables. Further the proposed method and system is fully integrated to allow a user to have their meal selection on a graphical user interface while the computer based optimization calculations of linear and non-linear vectors alongside optimization maximization equations have solved for optimal healthy choices for the user. For the purpose of efficiency in this document we will interchangeably use the term "User" and "Foodie".

In one implementation, the method and system for determining the optimal nutrition food intake solution may include receiving one or more parameters that describe the user's blood, saliva, hair, urine, stool, fingernail, height, weight and skin sampling analysis chemistry. The blood, saliva, hair, urine, stool, fingernail, height, weight and skin sampling analysis chemistry test data may then be submitted into a database that may be utilized to run a system of linear and non-linear systems of vectors alongside a system of vectors that considers food ingredients, flavor, ethnicity and style preferences in the context of a recipe that optimizes nutrition for a user's blood, saliva, hair, urine, stool, fingernail, height, weight and skin sampling analysis chemistry. The output of the applied math equation is a portfolio of blood, saliva, hair, urine, stool, fingernail, height, weight and skin sampling analysis optimized recipes or prepared dishes that are either raw or prepared which can then be delivered or picked up at the user's home, a raw food distribution point such as a grocery store or market, or a prepared food establishment such as a restaurant or prepared food kitchen distribution point. The search engine interface based on the optimized node rankings may be queried and rendered from the users location, search inputs, photo inputs, audio inputs, visual inputs, or recommended inputs. The user's budget may be a constrained part of the optimization equation so that the food choices are optimized over a given budget or level of service.

BRIEF DESCRIPTION OF THE DRAWINGS

Implementations of various technologies will hereafter be described with reference to the accompanying drawings. It should be understood, however, that the accompanying drawings illustrate only the various implementations described herein and are not meant to limit the scope of various technologies described herein. For the purpose of efficiency in this document we will interchangeably use the term "User" and "Foodie".

FIG. 10 illustrates the implementation of methods which may include a plurality of variables and constraint variables in the determining the optimal ingredients to improve the blood, saliva, hair, urine, stool, fingernail, height, weight and skin sampling analysis chemistry of a user through linear and non-linear vector maximization and minimization equations in accordance with some embodiments.

FIGS. 14A and 14B illustrate an exemplary implementation of methods utilizing a plurality of linear and non-linear equations to maximize nutrition of a user's consumption, health, variety, flavoring, style, ethnicity, nutrition and delivery of prepared and raw food which does not rely on a single diagnostic test or self-reporting problems because of independent blood, saliva, hair, urine, stool, fingernail, height, weight and skin sampling analysis tests subject to the constraints of income, price, and location in accordance with some embodiments.

FIGS. 17A and 17B and 17C illustrate one exemplary probability distribution of a particular ingredient affecting the blood, saliva, hair, urine, stool, fingernail, height, weight and skin sampling analysis chemistry of a Foodie or user as well as the mean of the expected return of ingredients to blood chemistry and the variance of an ingredient to the blood, saliva, hair, urine, stool, fingernail, height, weight and skin sampling analysis chemistry.

FIGS. 18A and 18B and 18C and 18D illustrate the blood, saliva, hair, urine, stool, fingernail, height, weight and skin sampling analysis chemistry of a vector of ingredients is the weighted average of the blood, saliva, hair, urine, stool, fingernail, height, weight and skin sampling analysis chemistry of each individual ingredient and the standard deviation as well as the covariance of ingredients on blood chemistry.

FIGS. 19A and 19B and 19C illustrate how the covariance and correlation equations of food ingredients affect the blood, saliva, hair, urine, stool, fingernail, height, weight and skin sampling analysis chemistry of the Foodie or user.

FIGS. 20A and 20B illustrate some descriptive biomarker blood, saliva, hair, urine, stool, fingernail, height, weight and skin sampling analysis statistics of a partial implementation of a simple two ingredient embodiment of the system and method.

FIG. 22B illustrates the ingredient combination opportunity set for various correlation factors.

FIGS. 24A and 24B illustrate the highest sloping Foodie allocation line (C) at point P intersecting with the opportunity set.

FIGS. 25A and 25B and 25C illustrate the framework to maximize the slope of the foodie allocation line subject to the condition that the sum of the weight of all the ingredients will sum to one which is a standard calculus problem.

FIGS. 26A and 26B illustrate the graphical solution of FIGS. 25A and 25B and 25C as well as the summarization of a two or more ingredient embodiment to a general embodiment.

FIG. 29 illustrates the expected general exemplary case of the method with vectors to illustrate any general combination of food chemistry components, ingredients and combinations and how they interact with any blood, saliva, hair, urine, stool, fingernail, height, weight and skin sampling analysis chemistry components or elements.

FIG. 31 illustrates additional data from the same specific embodiment shown in FIG. 30.

FIG. 32 illustrates additional data from the same specific embodiment shown in FIG. 30 and FIG. 31.

FIG. 36 illustrates an exemplary embodiment of a drill down selection of a certain selected element of the node ranked database of food and beverage which may have been optimized to consider blood, saliva, hair, urine, stool, fingernail, height, weight and skin sampling analysis based on machine learning algorithms.

FIG. 44 illustrates an exemplary embodiment of a biomarker low density lipoprotein and calcium attribute machine learning model equation sequence to node rank foods and beverages with specified optimization constraints and predictive sequences.

DETAILED DESCRIPTION

The discussion below is directed to certain specific implementations. It is to be understood that the discussion below is only for the purpose of enabling a person with ordinary skill in the art to make and use any subject matter defined now or later by the patent "claims" found in any issued patent herein.

Figure 1:
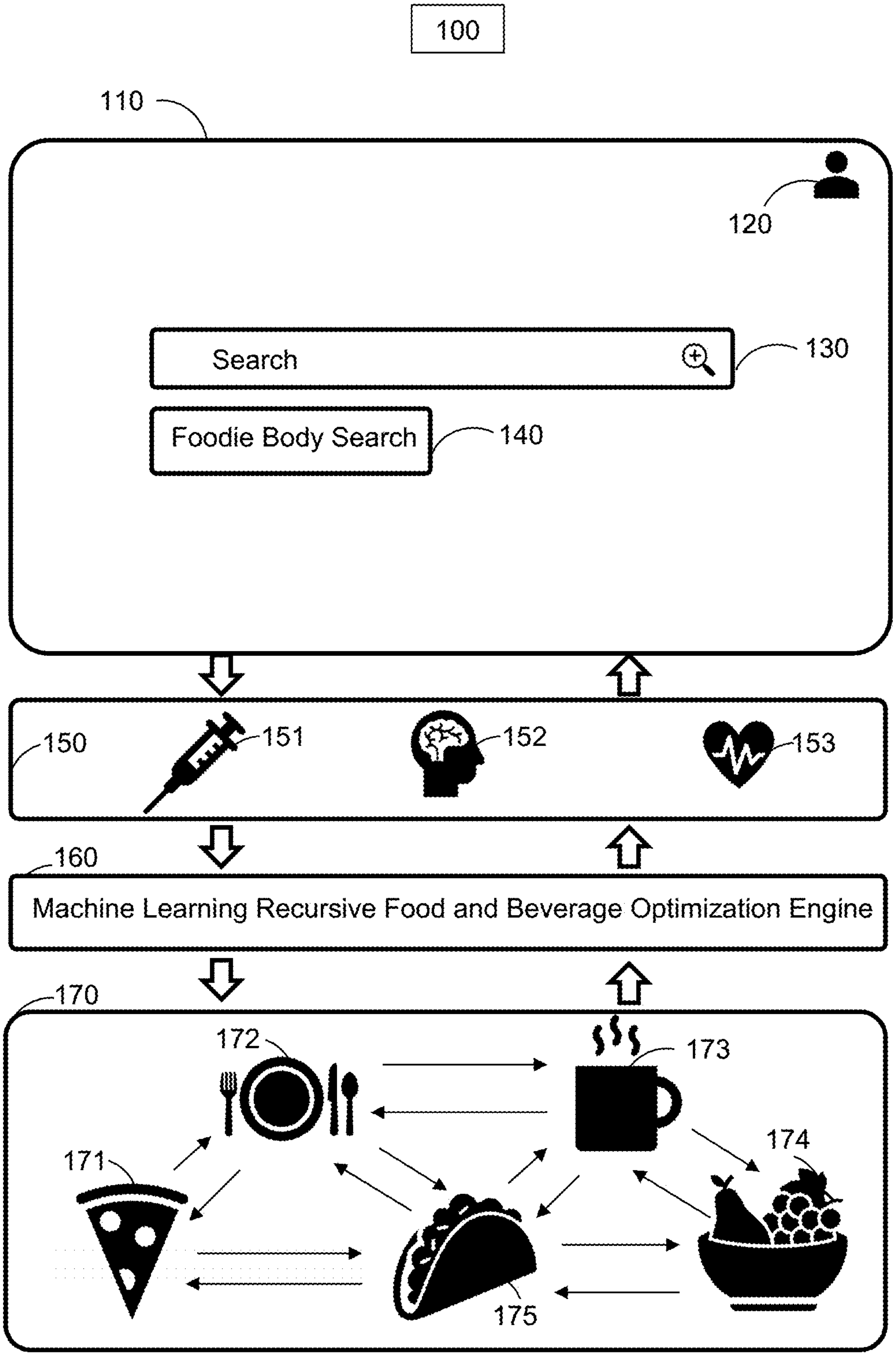
FIG. 1 illustrates a schematic diagram of the network configuration and implementations of methods which support the blood, saliva, hair, urine, stool, fingernail, height, weight and skin sampling analysis search interface node ranked optimized algorithms for food ordering and consumption in accordance with some embodiments.

The following paragraphs provide a brief summary of various techniques described herein such as illustrated as in FIG. 1. For the purpose of efficiency in this document we will interchangeably use the term "User" and "Foodie". Also for the purpose of efficiency, "blood chemistry" may be used as short form or interchangeably with any superset or subset of blood, saliva, hair, urine, stool, fingernail, height, weight and skin sampling analysis or other biomarkers such by example but not limiting by example echocardiogram, nuclear perfusion studies, magnetic resonance imaging, positron emission tomography with biomarker chemistry data. In one exemplary implementation as illustrated in FIG. 1, a searchable food and beverage ranked node database interface 110 may display a plurality of food and beverage selections 170 to a user 120. In one embodiment, a user 120 may provide a blood, saliva, hair, urine, stool, fingernail, height, weight and skin sampling analysis 150 to a certified biomarker laboratory 151 through a plurality of options. In one embodiment a user 120 may provide a positron emission tomography scan 152 to the database to allow the machine learning recursive food and beverage optimization and search engine 160 to display a plurality of ranked foods and beverages 170. In one embodiment a user 120 may provide an electrocardiogram, nuclear stress test, angiogram, computed tomography or magnetic resonance imaging data 153 to the database to allow the machine learning recursive food and beverage optimization and search engine 160 to display a plurality of ranked foods and beverages 170. In another embodiment a user 120 may provide a plurality of biometric samples 150 to the database to allow the machine learning recursive food and beverage optimization and search engine 160 to display a plurality of ranked foods and beverages 170. In some embodiments, the machine learning recursive food and beverage optimization engine node ranks a database 170 based on machine learning models 160 that estimate personalized food and beverage selections 170 based on predictive and historical samples of food and beverage compared to a plurality of biomarker test results from labs including but not limited to blood, saliva, hair, urine, stool, fingernail, height, weight and skin sampling analysis 150.

Figure 2:
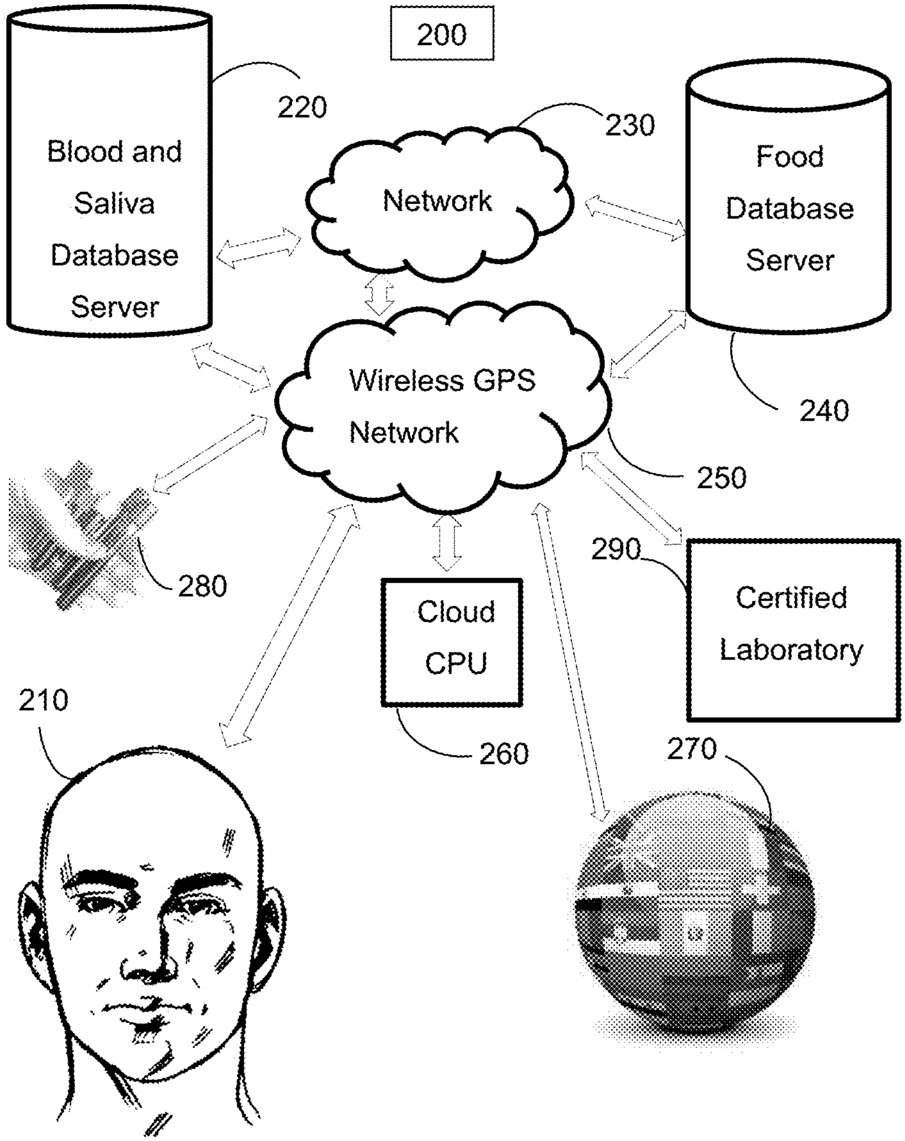
FIG. 2 illustrates a schematic diagram of the network configuration and implementations of methods which support the blood, saliva, hair, urine, stool, fingernail, height, weight and skin sampling analysis optimized algorithms for food ordering and consumption and the associated application graphical user interface designed for both 2d and 3d smart devices as well as augmented reality, audio interface and mixed reality interface configurations in accordance with some embodiments.

The embodiment illustrated in FIG. 2. Illustrates the certified laboratory 290 may then transmit the biometric test results from the blood, saliva, hair, urine, stool, fingernail, height, weight and skin sampling analysis 280 to a network 230 which then archives the data in a biomarker blood, saliva, hair, urine, stool, fingernail, height, weight and skin sampling analysis database server 220. The network 230 also interacts with the user 210 and a food database server 240 which has compiled a plurality of nutrition information on food ingredients from a plurality of global resources. Food providers of raw food ingredients or prepared dishes use the graphical user interface 270 of a CPU 270 to upload ingredient information 240 to the network 230 which then stores the nutrition information in the food database server 240. The user 210 interacts with the network 230 through the graphical user interface 270 by selecting a plurality of options regarding nutrition, health, variety, flavoring, style, ethnicity and delivery of prepared and raw ingredients. The cloud based CPU 260 contains algorithms and machine learning sequences of linear and non-linear equations which use a plurality of vectors to determine the optimal nutrition ingredients or prepared dishes which optimize blood, saliva, hair, urine, stool, fingernail, height, weight and skin sampling analysis of the user 210 by interaction with the network 230 and pulling data recursively from the blood, saliva, hair, urine, stool, fingernail, height, weight and skin sampling analysis database server 220 and food database server 240. In some embodiments, the food and beverage results may be node ranked in relation to moving the user 210 towards a biomarker target with the highest efficiency and lowest variance. The user 210 may submit blood, saliva, hair, urine, stool, fingernail, height, weight and skin sampling analysis 280 to the certified laboratory 270 through a plurality of methods to update the network 230 and blood, saliva, hair, urine, stool, fingernail, height, weight and skin sampling analysis database server 220 in a plurality of frequencies to improve the ability of the algorithms in the cloud CPU 260 to optimize ingredients and rank food and beverage selections from the food database server 240. The food database server 240 contains a schema for individual ingredients as well as combinations of ingredients from recipes which have been uploaded by a plurality of users 210 through the graphical user interface 270. The graphical user interface 270 may be obtained on a stationary CPU, mobile device, augmented reality device, mixed reality device, audio interface or any device capable of presenting a graphical user interface 270 or audio interface 270 to a user 210. The form of the graphical user interface may be a globe with flags of countries, a map with geographic location of countries, country listing, voice listing of countries or other representations of geographic and cultural areas 270 or a plurality of food and beverage selections from the food database server 240 over the network 230 and wireless GPS network 250. The user 210 and network 230 and graphical user interface 270 may interact with the wireless GPS location network 250 to obtain position of the user 210 relative to the user 210 to consider delivery mechanisms to the user and to constrain the optimization equations for cost of delivery or other location preferences. The embodiment illustrated in FIG. 2. illustrates further a user 210 interacting with a wireless network 250 and a network 230 that connects a blood, saliva, hair, urine, stool, fingernail, height, weight and skin sampling 280 analysis database server 220 based on blood, saliva, hair, urine, stool, fingernail, height, weight and skin sampling analysis and test results from a user 210 with a food database server 240 which contains nutrition data on raw ingredients and combinations of raw ingredients in the form of recipes and prepared food combinations of nutrition, health, variety, flavoring, style, ethnicity and delivery. The user 210 may access the wireless network 250, network 230, blood, saliva, hair, urine, stool, fingernail, height, weight and skin sampling analysis database server 220, food database server 240, cloud CPU 260 or other CPUs accessible through the network 230 through the graphical user interface 270. The user 210 continuously updates the blood, saliva, hair, urine, stool, fingernail, height, weight and skin sampling 280 analysis database server 220 by having a certified laboratory or certified home collection kit collect blood, saliva, hair, urine, stool, fingernail, height, weight and skin sampling analysis samples 280 on a plurality of intervals to optimize food selection from the food database server 240.

Figure 3A:
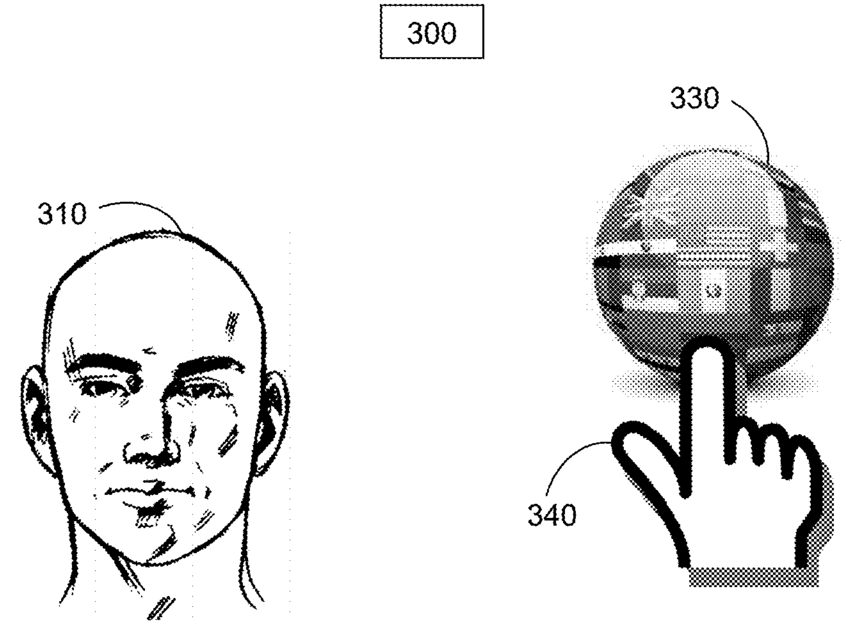
FIGS. 3A and 3B illustrate the implementation of methods of a typical user selecting the ethnicity or style of food prior to the algorithms optimization calculations considering the blood, saliva, hair, urine, stool, fingernail, height, weight and skin sampling analysis chemistry of the user amongst other variables in accordance with some embodiments.
Figure 3B:
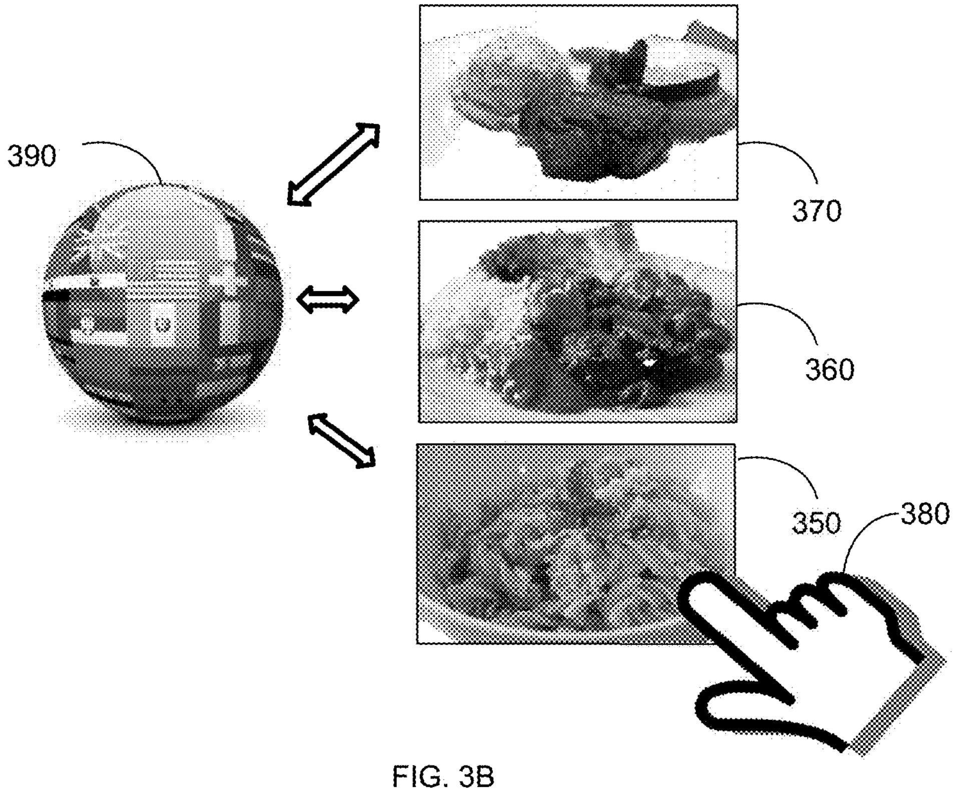

The embodiment illustrated in FIG. 3A. illustrates further a user 310 selecting a country of origin for food flavor, variety, style, ethnicity preference from the graphical user interface 330. The user 310 may select the flavor, variety, style, ethnicity preference 340 which then initiates a method of setting up a recursive process of performing optimization equations on linear and nonlinear algebra vectors of various food combinations that optimize the chemistry of blood, saliva, hair, urine, stool, fingernail, height, weight and skin sampling analysis. The embodiment illustrated in FIG. 3B. illustrates further a user 310 directs a tool 380 from the graphical user interface to select a plurality of prepared or raw food options such as a combination of meat, potatoes and other vegetables 370, rice, Indian sauces, and breads 360, seafood pasta 350. The user 310 may scroll the suggested options 370, 360, 350 by sliding, rolling, swiping or other intuitive movements to the graphical user interface 390 user controlled pointer 380.

Figure 4A:
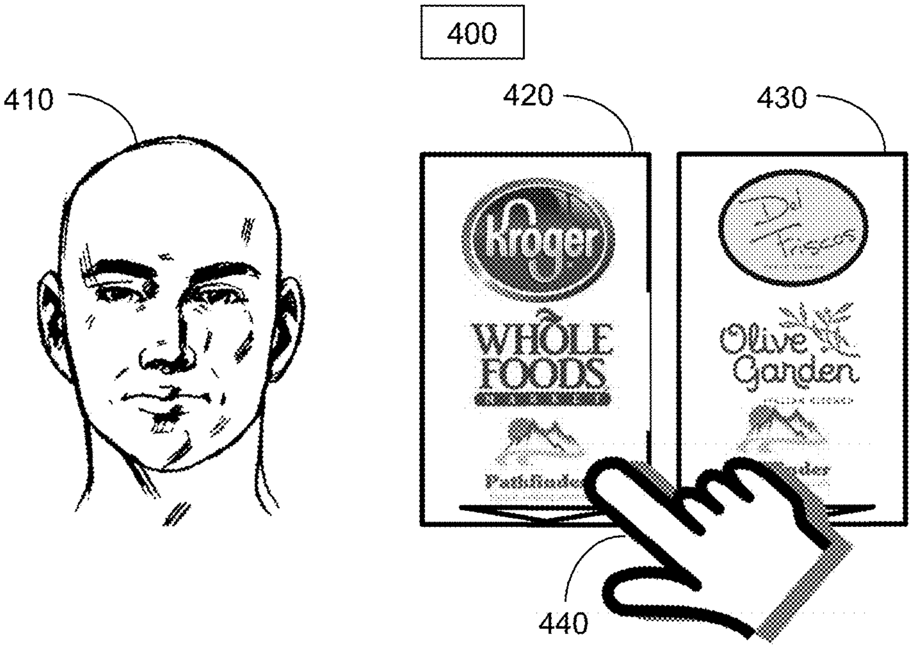
FIGS. 4A and 4B illustrate the implementation of methods of a typical user selecting a plurality of food distributors of prepared or raw food utilizing the graphical user interface of the blood, saliva, hair, urine, stool, fingernail, height, weight and skin sampling analysis nutrition optimized algorithms in accordance with some embodiments.
Figure 4B:
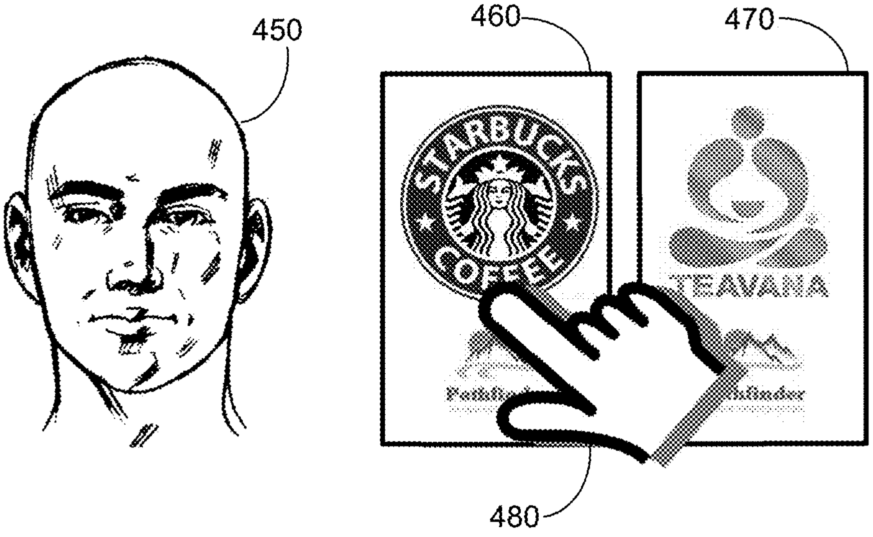

The embodiment illustrated in FIG. 4A. illustrates further a user 410 selecting with the graphical user interface pointer 440 a store or brand of food 420 which carries raw food or prepared foods that have been uploaded by the vendor 420 so that the blood, saliva, hair, urine, stool, fingernail, height, weight and skin sampling analysis optimization equations may select raw ingredients, combinations of raw ingredients and prepared foods which optimize the users 410 blood, saliva, hair, urine, stool, fingernail, height, weight and skin sampling analysis chemistry. The user 410 may also select restaurants 430 that have uploaded food menus or food choices that have been optimized for the users 410 blood, saliva, hair, urine, stool, fingernail, height, weight and skin sampling analysis chemistry. The embodiment illustrated in FIG. 4B. illustrates further a user 450 directing a graphical user interface pointer 480 in one configuration amongst many configurations where the user 450 may select a drink such as coffee, hot chocolate, tea, wine, milk, water, carbonated drink, juice, beer, cider, or spirit from a vendor 460, 470 who participates in the system.

Figure 5:
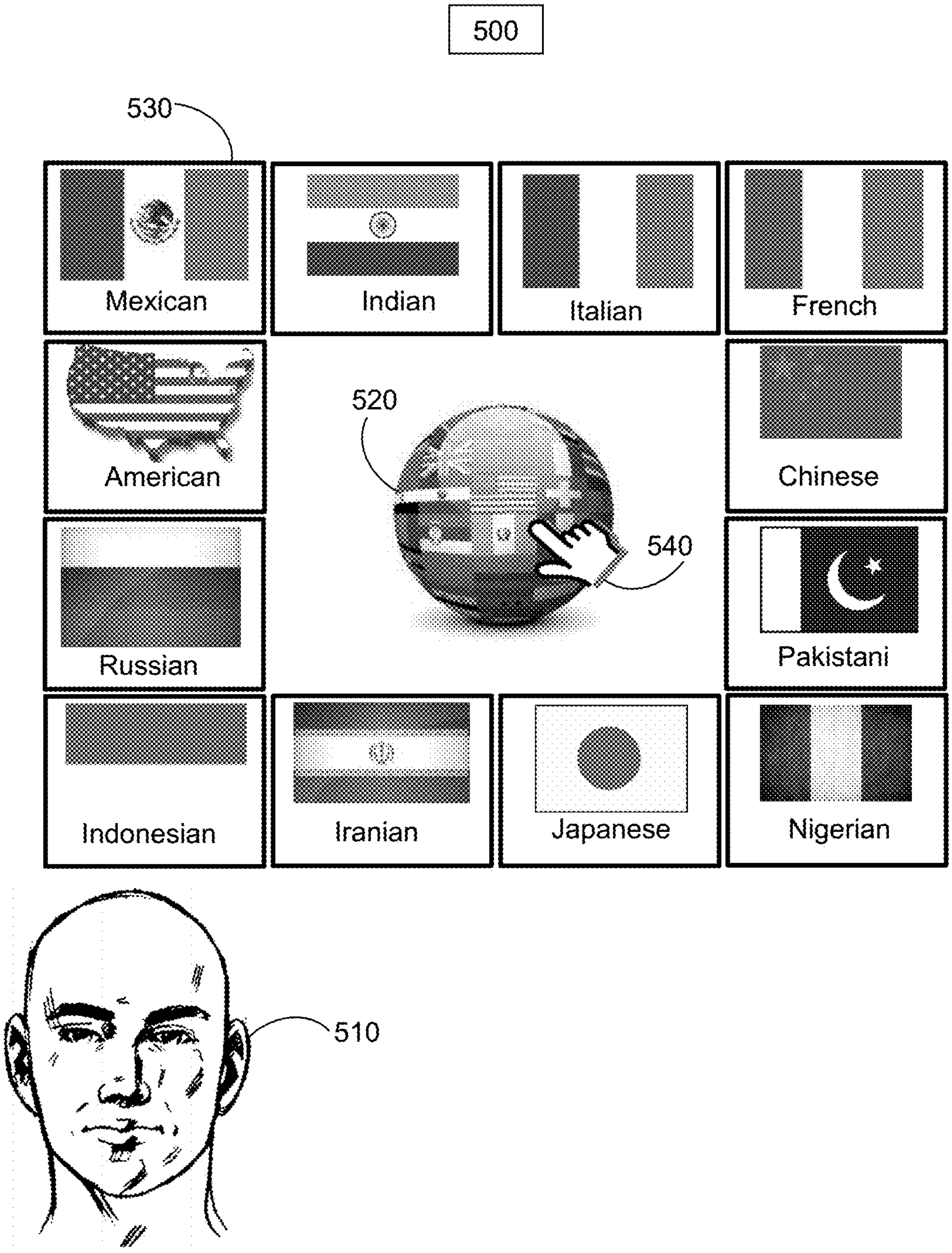
FIG. 5 illustrates the implementation of methods of a typical user selecting the style and ethnicity of the food choice prior to blood, saliva, hair, urine, stool, fingernail, height, weight and skin sampling analysis optimization of the nutrition content utilizing the graphical user interface of the associated application designed for both 2d and 3d smart devices, audio interface as well as augmented reality and mixed reality interface configurations in accordance with some embodiments.
Figure 6A:
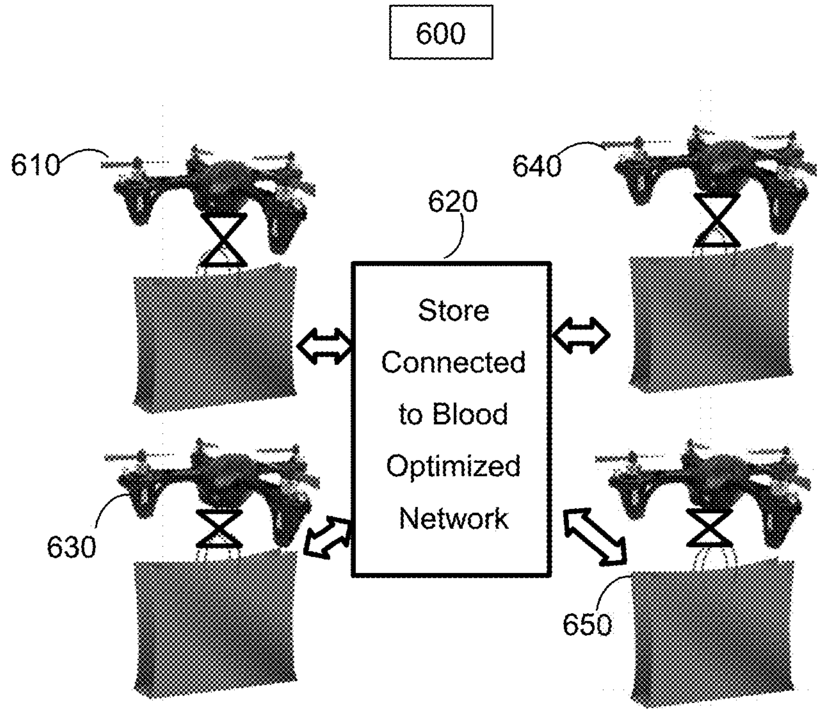
FIGS. 6A and 6B illustrate the implementation of methods of delivery of raw food or prepared food and beverage over the network of stores which are connected to the blood, saliva, hair, urine, stool, fingernail, height, weight and skin sampling analysis optimized network in accordance with some embodiments.
Figure 6B:
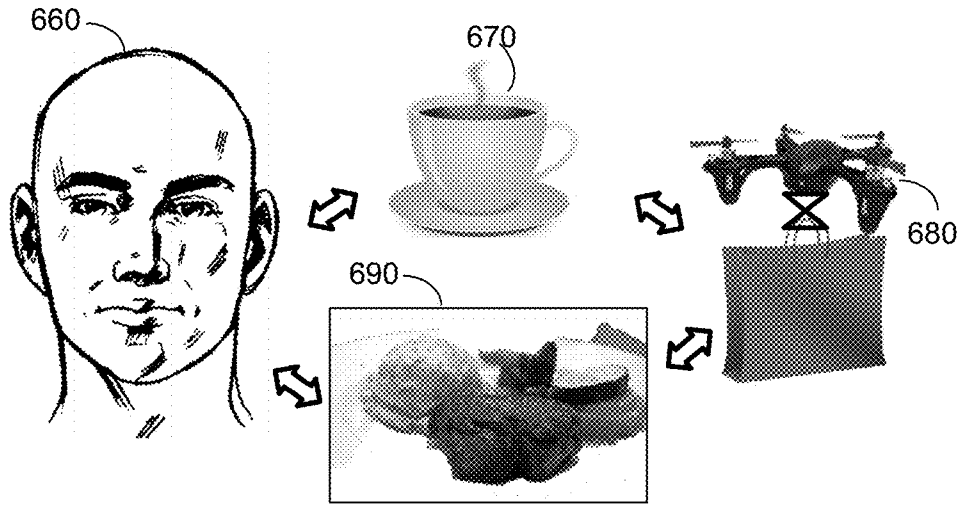

The embodiment illustrated in FIG. 5. illustrates further a user 510 selecting with the graphical user interface pointer 540 a style or country or flavor or ethnicity of food 530 as an input to the vector based system of linear and non-linear equations to optimize blood, saliva, hair, urine, stool, fingernail, height, weight and skin sampling analysis of a user 510 taking into account the style or country or flavor or ethnicity that the user 510 desires The embodiment illustrated in FIG. 6B. illustrates further a user 660 selecting with the graphical user interface a drink 670 and combination of ingredients in the form of a recipe which includes raw ingredients or prepared food 690 which can then be picked up at a specified location or delivered to the user 660 via a drone 680 or a plurality of other delivery methods. The embodiment illustrated in FIG. 6A. illustrates further a user 660 that may be connected to the network of stores that use the blood, saliva, hair, urine, stool, fingernail, height, weight and skin sampling analysis optimized database structure and schema 620 to optimize blood, saliva, hair, urine, stool, fingernail, height, weight and skin sampling analysis chemistry considering food consumption. A plurality of pick up or delivery methods may be utilized that include but are not limited to programmed drones 610, 630, 640, 650. The drones 680 may be operated by humans or may be autonomous.

Figure 7A:
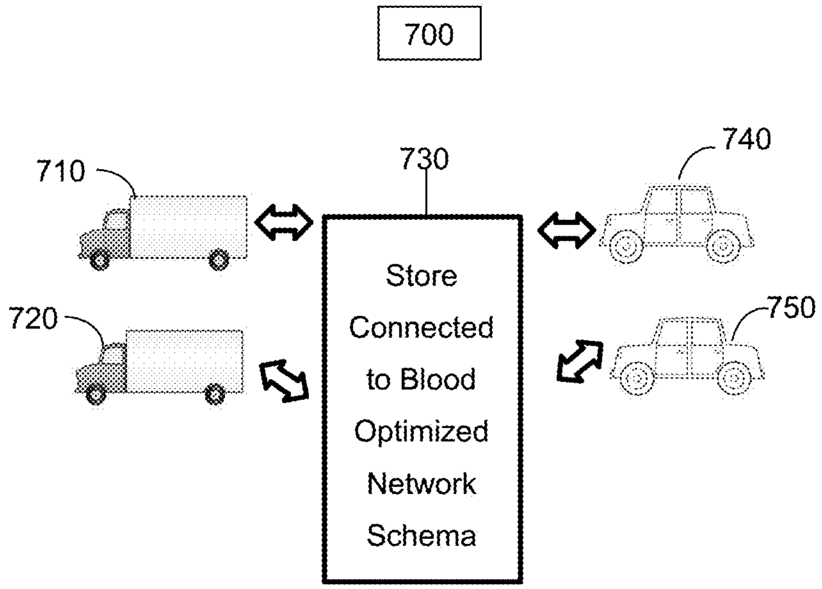
FIGS. 7A and 7B illustrate the implementation of methods of delivery of raw food or prepared food and beverage over the network of stores which are connected to the blood, saliva, hair, urine, stool, fingernail, height, weight and skin sampling analysis optimized network in accordance with some embodiments.
Figure 7B:
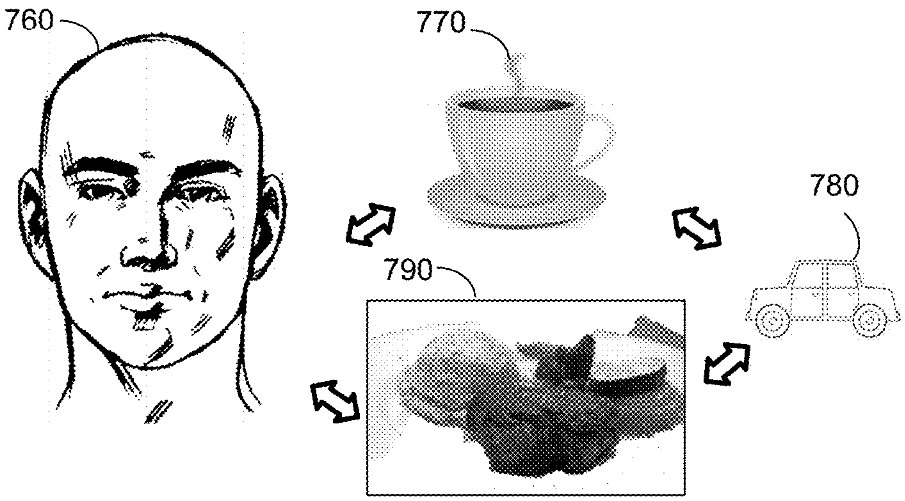

The embodiment illustrated in FIG. 7B. illustrates further a user 760 selecting with the graphical user interface a drink 770 and combination of ingredients in the form of a recipe which includes raw ingredients or prepared food 790 which can then be picked up at a specified location or delivered to the user 760 via a vehicle 780 or a plurality of other delivery methods. The embodiment illustrated in FIG. 6A. illustrates further a user 760 that may be connected to the network of stores that use the blood, saliva, hair, urine, stool, fingernail, height, weight and skin sampling analysis optimized database structure and schema 730 to optimize blood, saliva, hair, urine, stool, fingernail, height, weight and skin sampling analysis chemistry considering food consumption. A plurality of pick up or delivery methods may be utilized that include but are not limited to programmed vehicles 710, 720, 740, 750. The vehicles 780 may be operated by humans or may be autonomous.

Figure 8:
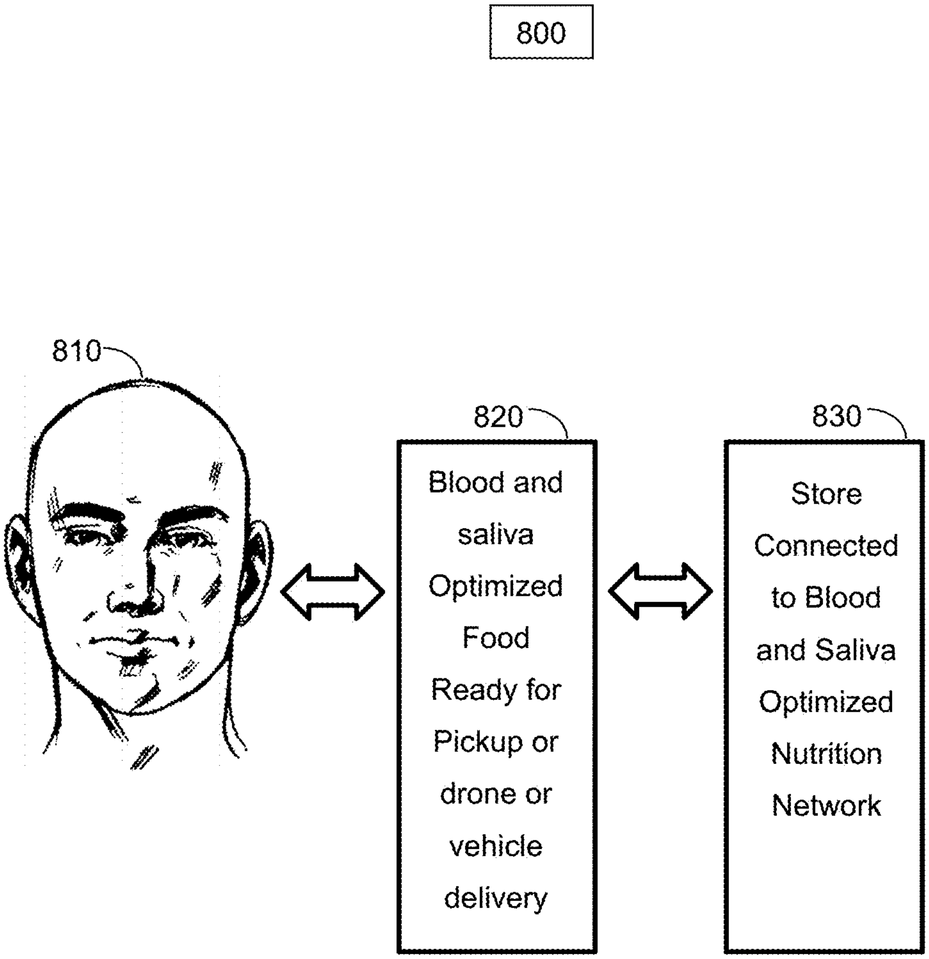
FIG. 8 illustrates the implementation of methods of delivery of raw food or prepared food and beverage over the network of stores which are connected to the blood, saliva, hair, urine, stool, fingernail, height, weight and skin sampling analysis optimized network in accordance with some embodiments.

The embodiment illustrated in FIG. 8. illustrates further a user 810 may select with the graphical user interface blood, saliva, hair, urine, stool, fingernail, height, weight and skin sampling analysis optimized food which is ready for pickup 820 from a store or restaurant or cooking node which is connected to the blood, saliva, hair, urine, stool, fingernail, height, weight and skin sampling analysis optimized network 830. Grocery stores, food warehouses, co-ops, food distribution centers, restaurants, certified kitchens, or a plurality of other nodes capable of providing raw or prepared food may be connected to the blood, saliva, hair, urine, stool, fingernail, height, weight and skin sampling analysis optimized nutrition network 830. Grocery stores, food warehouses, co-ops, food distribution centers, restaurants, certified kitchens, or a plurality of other nodes capable of providing raw or prepared food may prepare the food for pickup 820 or distribute the food via drone or delivery vehicle.

Figure 9:
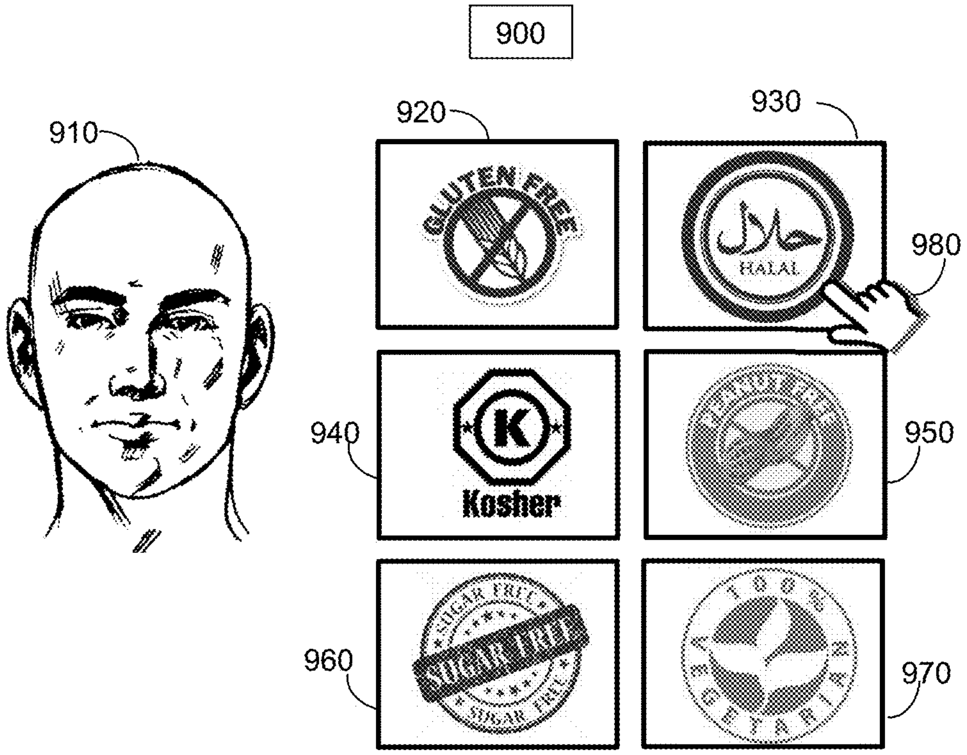
FIG. 9 illustrates the implementation of methods dietary type of style choices in the delivery matrix of raw food or prepared food and beverage over the network of stores which are connected to the blood, saliva, hair, urine, stool, fingernail, height, weight and skin sampling analysis optimized network in accordance with some embodiments.

The embodiment illustrated in FIG. 9. illustrates further a user 910 may select with the graphical user interface pointer 980 blood and saliva optimized food which may have a certain type of food designation such as gluten free 920, halal 930, kosher 940, peanut free 950, sugar free 960, vegetarian 970, or a plurality of other designations that would be in the preference portfolio vector of the user 910.

In one implementation as illustrated in FIG. 10, they method and system may maximize 1010 foodie score, user utility, nutrient content, flavoring, ethnicity, variety, style, preference, health, delivery subject to a plurality of contribution, constraint and variance data comprised from blood, saliva, hair, urine, stool, fingernail, height, weight and skin sampling analysis samples 280 to a certified laboratory 290 through a plurality of options. In some embodiments the biomarker settings may consider blood type, phosphorus levels, platelets, HDL Cholesterol, Thyroid, Hemoglobin, Iron, Vitamin B12, Hematocrit, Ketones, Amylase, Mean Corpuscular Volume, LDL cholesterol, serum protein, blood glucose, magnesium, complete blood count, potassium, red blood cells, calcium, progesterone, white blood cells, electrolytes, creatine kinase, triglycerides, allergen profile, troponin, coagulation panel, celiac, budget, HLA-DQ8 Gene, HLA-DQ2 gene, sums of ingredients, allergies, weight constraints, beta amyloid, serum docosahexaenoic acid, tau phosphorylation, serum low density lipoprotein (LDL) and other measurable biomarkers 1020.

Figure 11:
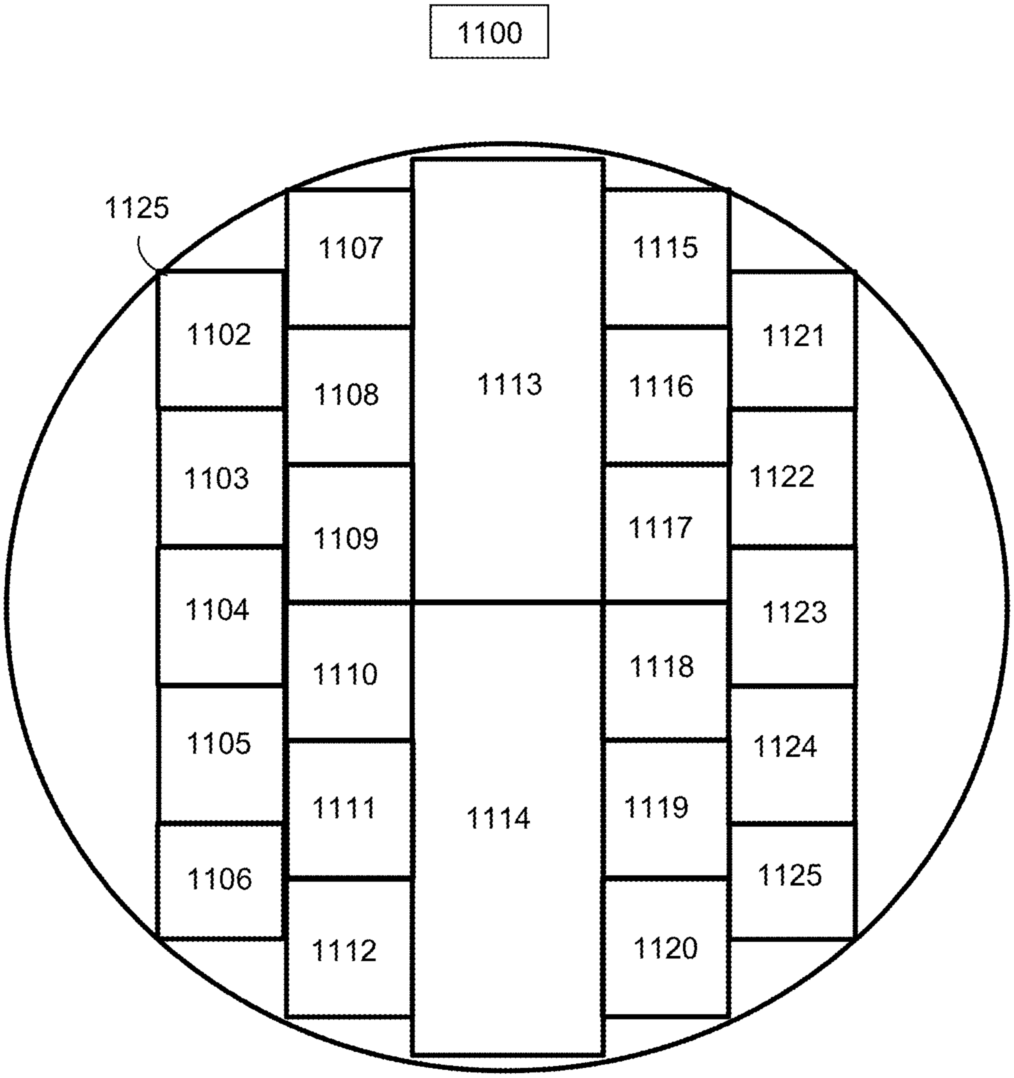
FIG. 11 illustrates a diagram of a mobile computer ball CPU device which may be in accordance with some embodiments.

The embodiment illustrated in FIG. 11. illustrates the mobile network based ball CPU projection device 1125. The blood and saliva optimized food methods and system may be used on any CPU device which is stationary or mobile with access to a network. One configuration of a CPU device which can process the blood and saliva optimized food methods and system may be the device 1125 which may include a memory 1102, a memory controller 1103, one or more processing units (CPUs) 1104, a peripherals interface 1105, RF circuitry 1106, audio circuitry 1108, one or more speakers 1107 and 1115, a microphone 1109, an input/output (I/O) subsystem 1110, input control devices 1111, an external port 1112, optical sensors 1116, camera 1113, one or more laser projection systems 1114, power supply 1117, battery 1118, wifi module 1119, GPS receiver 1120, accelerometer 1121, Ambient light sensor 1122, location sensor 1123, barometer 1124, USB port 1125. The device 1125 may include more or fewer components or may have a different configuration or arrangement of components. The CPUs 1104 run or execute various instructions compiled by software and applications which are stored in the memory 1102 that perform various functions on the device 1125 such as the blood and saliva optimized food methods and system. The RF circuitry 1106 receives and sends RF signals. The RF circuitry 1106 converts electrical signals to/from electromagnetic signals and communicates with communications networks 140 and 150 and other communication devices via the electromagnetic signals. The instructions to perform the mathematic algorithm optimization may be on a local CPU such as 1125 or a cloud based CPU 190. The RF circuitry may be comprised of but not limited to an antenna system, a tuner, a digital signal processor, an analogue signal processor, various CODECs, a SIM card, memory, amplifiers, an oscillator and a transceiver. The wireless communication components may use a plurality of standard industry protocols such as Global System for Mobile Communication ("GSM"), Voice over internet protocol ("VOIP"), long-term evolution ("LTE"), code division multiple access ("CDMA"), Wireless Fidelity ("WiFi"), Bluetooth, Post office Protocol ("POP"), instant messaging, Enhanced Data GSM Environment ("EDGE"), short message service ("SMS"), or other communication protocol invented or not yet invented as of the filing or publish date of this document. The input/output subsystem 1110 couples with input/output peripherals 1105 and other control devices 1111 and other laser projection systems 1114 to control the device 1125. The laser projection system 1114 and camera 1113 take infrared tracking information feedback from the user 120 into the peripheral interface 1105 and CPU 1104 to combine the data with instructions in the CPU 1104 and memory 1102 that provide an iterative instruction for the graphical user interface which is displayed in the waveguide lens 240 or 210 after comparison with information in the memory from the database server 260. The input control devices 1111 may be controlled by user 120 movements that are recorded by the laser projection system 1114 and camera 1113. The audio circuitry 1108, one or more speakers 1107 and 1115 and the microphone 1119 provide an audio interface between the user and the device 1125. The audio circuitry 1108 receives audio data from the peripherals interface 1105, converting the data to an electrical signal, and transmits the electrical signal to the speakers 1107 and 1115. The speakers 1107 and 1115 convert the electrical signals to human audible sound waves which are mechanotransducted into electrical impulses along auditory nerve fibers and further processed into the brain as neural signals. The audio circuitry 1108 also receives electrical signals converted by the microphone 1109 from sound waves. The audio circuitry 1108 converts the electrical signal to audio data and transmits the audio data to the peripherals interface 1105 for processing. Audio data may be retrieved and/or transmitted to memory 1102 and/or the RF circuitry 1106 by the peripherals interface 1105. In some embodiments the RF circuitry may produce ultra-high frequency waves that transmit to wireless headphones which then convert the electrical signals to human audible sound waves which are mechanotransducted into electrical impulses along auditory nerve fibers and further processed into the brain as neural signals. The device 1125 also includes a power supply 1117 and battery 1118 for powering the various components. The USB port 1125 may be used for providing power to the battery 1118 for storage of power. The location sensor 1123 couples with the peripherals interface 1105 or input/output subsystem 1110 to disable the device if the device 1125 is placed in a pocket, purse or other dark area to prevent unnecessary power loss when the device 1125 is not being used. The software instructions stored in the memory 1102 may include an operating system (LINUX, OS X, WINDOWS, UNIX, or a proprietary operating system) of instructions of various graphical user interfaces 1200.

Figure 12:
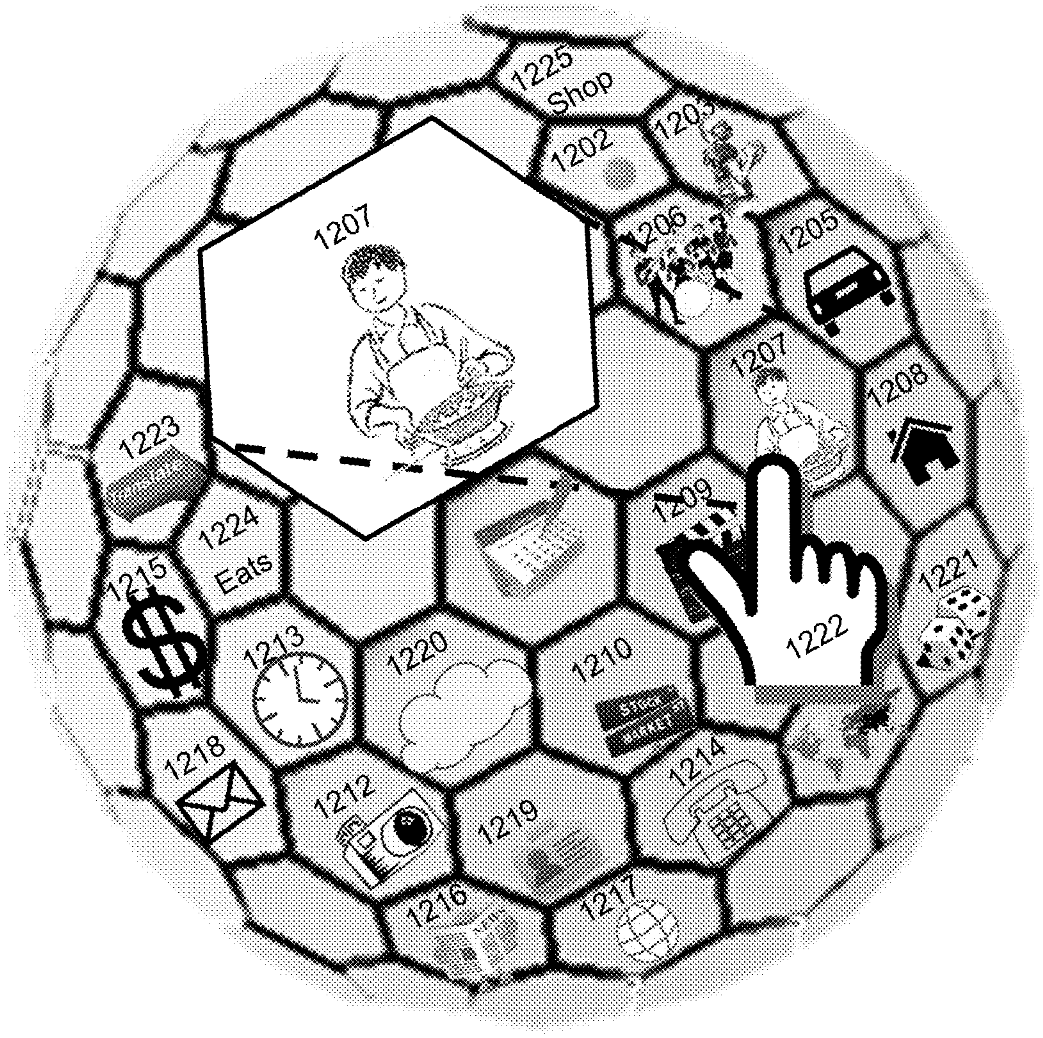
FIG. 12 illustrates an exemplary user interface for selecting a plurality of applications in accordance with some embodiments.

The embodiment illustrated in FIG. 12. illustrates the graphical user interface of the system which may include a network based ball CPU projection device 1125. The system may include instructions for object hologram embodiments of a calendar 1201, photos 1212, camera 1212, videos 1209, maps 1211, weather 1202, credit cards 1215, banking 1215, crypto currency 1215, notes, clocks 1213, music 1206, application hosting servers 1220, settings 1220, physical fitness 1203, news 1216, video conferencing 1209, home security 1208, home lighting 1208, home watering systems 1208, home energy 1208 or temperature settings 1208, home cooking 1207, phone 1214, texting services, mail 1218, internet 1217, social networking 1219, blogs 1219, investments 1210, books, television 1209, movies 1209, device location, flashlights, music tuners 1206, airlines 1205, transportation 1205, identification 1219, translation, gaming 1221, real estate 1208, shopping, food 1207, commodities 1215, technology 1217, memberships, applications 1220, web applications 1217, audio media 1206, visual media 1209, mapping or GPS 1211, touch media 1217, general communication 1214, internet 1217, mail 1218, contacts 1219, cloud services 1220, games 1221, translation services 1223, virtual drive through with geofence location services for nearby restaurants to allow advance ordering of food and payment 1224 such as the food and saliva based algorithm to optimize personal nutrition, virtual shopping with custom measurements through infrared scans 1225, etc. . . . and facilitates communication between various hardware and software components. The blood and saliva optimized food algorithm application may appear as represented in object 1207 or 1224. The application 1207 or 1224 may scan pictures of food which has been set for consumption by the user which has not been ordered through the system so that the ingredients may be identified and the data included in the blood and saliva based optimization models of blood and saliva chemistry.

Figure 13:
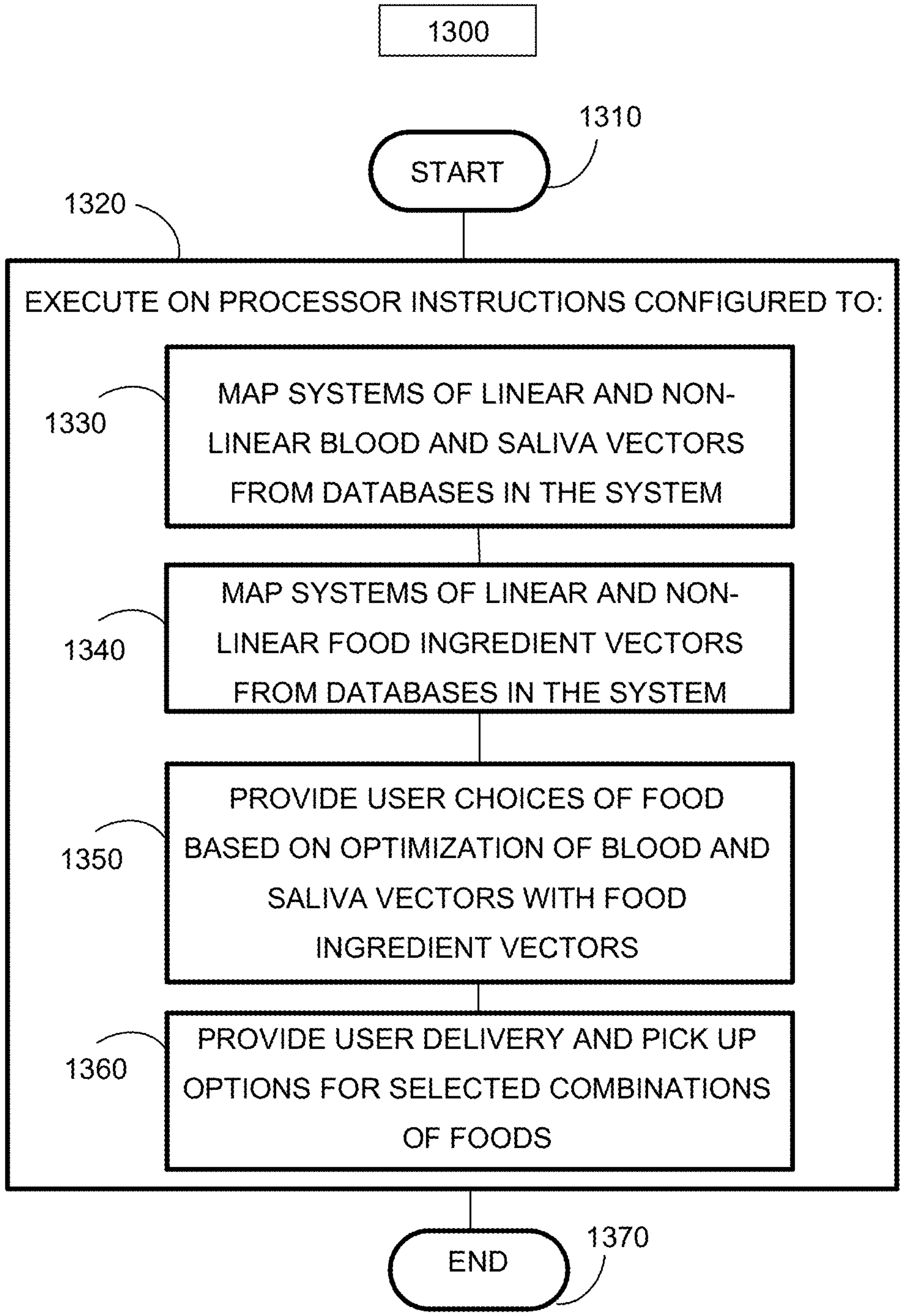
FIG. 13 illustrates an exemplary flow chart of a plurality of applications and iterations of the blood, saliva, hair, urine, stool, fingernail, height, weight and skin sampling analysis chemistry of a user through linear and non-linear vector maximization and minimization equations in accordance with some embodiments in accordance with some embodiments.

The process flow diagram in FIG. 13 illustrates implementations of methods and the system where a user 210 uses the system and methods. A user 210 starts 1310 the implementation of the methods and systems by selecting a plurality of options regarding nutrition, health, variety, flavoring, style, ethnicity and delivery. The system takes the inputs to execute on a processor instructions configured to 1320 complete the following instructions. In one implementation of the methods, the system maps systems of linear and non-linear blood, saliva, hair, urine, stool, fingernail, height, weight and skin sampling analysis vectors from databases in the system 1330. The map of the system of linear and non-linear blood, saliva, hair, urine, stool, fingernail, height, weight and skin sampling analysis vectors forms a matrix which will then form the basis of part of the system of optimization equations used to select food options for the user. The system and methods further map systems of linear and non-linear food ingredient vectors from databases in the system 1340 which form a matrix of food nutrition content. The matrices are then multiplied to optimize the weights of ingredients to ensure optimal blood, saliva, hair, urine, stool, fingernail, height, weight and skin sampling analysis chemistry for the user's body. The variance-covariance matrix is square and symmetric. The optimization equation weights have also considered groups of food ingredients that form the basis of prepared meals and recipes which are combinations of ingredients. The system then provides the user delivery and pick-up options for selected combinations of foods 1360. The implementation of methods is recursive and the optimal weights are being adjusted after each meal considering the historical ingredients consumed and blood, saliva, hair, urine, stool, fingernail, height, weight and skin sampling analysis data that is submitted into the database of the system for node rankings. The techniques and methods discussed herein may be devised with variations in many respects, and some variations may present additional advantages and/or reduce disadvantages with respect to other variations of these and other techniques and methods. Moreover, some variations may be implemented in combination, and some combinations may feature additional advantages and/or reduced disadvantages through synergistic cooperation and reweighting of the models through recursive optimization. The variations may be incorporated in various embodiments to confer individual and/or synergistic advantages upon such embodiments.

The embodiment of the method and system illustrated in FIGS. 14A and 14B illustrates a representative food market with heterogeneous expectations. Traditionally the buyer and seller have very different information. In an exemplary scenario, the seller or manufacturer or cook knows the ingredient attributes whereas the buyer may make a purchase without knowing the ingredient attributes or their chemistry effect on the blood. Surely the buyer can do research on all the ingredients, but generally the buyer does not have the same resources as the producer of the food who has food scientists and research staff to understand the effects of the ingredient attributes on blood chemistry or other aspects of human health. Similarly, a mother or father may make a batch of cookies for their child thinking that the act of making cookies is showing love to their child if consumed in reasonable quantities. However if the father or mother did not know their child was gluten intolerant or had celiac disease in fact they were unknowingly inflicting pain on their child through the dietary choice. The implementation of the method considers that it is very costly for buyers and sellers of food to have homogeneous information or even to reduce heterogeneous information so that people make less sub-optimal food choices as consumers or that stores offer the wrong types of food to their primary demographics and customers. The implementation of the method has provided a solution for these problems and has greatly reduced or nearly eliminated the problem of heterogeneous information on food ingredients relative to personal blood, saliva, hair, urine, stool, fingernail, height, weight and skin sampling analysis chemistry. The implementation of the method allows both the restaurant and the customer to speak the same language of food chemistry for the respective blood and saliva chemistry while considering flavor, ethnicity, or style preferences. The implementation of the method allows both the grocery store and the customer to speak the same language of food chemistry for the respective blood, saliva, hair, urine, stool, fingernail, height, weight and skin sampling analysis chemistry while considering flavor, ethnicity, or style preferences. The implementation of the method allows both the family meal cook and the family member or friend to speak the same language of food chemistry for the respective blood, saliva, hair, urine, stool, fingernail, height, weight and skin sampling analysis chemistry while considering flavor, ethnicity, or style preferences. The implementation of the method allows both host of a party and all the guests to speak the same language of food chemistry for the respective blood, saliva, hair, urine, stool, fingernail, height, weight and skin sampling analysis chemistry of guests while considering flavor, ethnicity, or style preferences. Blood tests and saliva historically have been costly which add to the problem of heterogeneous information between food provider and food consumer. The implementation of the method and system may cover the cost of the blood, saliva, hair, urine, stool, fingernail, height, weight and skin sampling analysis test which can be self-administered with system equipment or administered by a lab in the system and method network. The method and system may reduce the overall food consumption of the user by providing mathematically rigorous and nutritional foods for the consumer's blood, saliva, hair, urine, stool, fingernail, height, weight and skin sampling analysis which reduces food waste and wasted calorie consumption. The blood, saliva, hair, urine, stool, fingernail, height, weight and skin sampling analysis test may be self-administered through method and system equipment that is sent to the user or administered by a lab in the system. To quantify embodiments of the method and system 1400, FIG. 14A illustrates a general utility function. The system and method assigns a utility function or "Foodie Score" 1410 to their diet preferences which ranks through a series of neural network feedback on food styles, ethnicity, variety, flavoring. The equation 1410 has the following variables, F(foodie score) which is the utility function, E(Bblood chemistry) which is the current blood, saliva, hair, urine, stool, fingernail, height, weight and skin sampling analysis chemistry of a portfolio of ingredients minus 0.005 which is a scaling convention that allows the system and method to express the current blood, saliva, hair, urine, stool, fingernail, height, weight and skin sampling analysis chemistry of a portfolio of ingredients and the standard deviation of those ingredients to be a percentage rather than a decimal. The term A in 1410, is an index of the users preference which is derived from using neural networks that have been trained on the users preferences. The term A in 1410 is continually updated in a recursive fashion to reflect the user's preferences in style, ethnicity, flavoring or other characteristics. The sigma term squared in 1410 is the variance is of the blood chemistry of a portfolio of ingredients. The utility function or foodie score 1410 represents the notion that the foodie utility is enhanced or goes up when the blood, saliva, hair, urine, stool, fingernail, height, weight and skin sampling analysis chemistry is within target and diminished or reduced by high variance blood chemistry or blood chemistry which brings the user out of target ranges. The extent by which the foodie or user is negatively affected by blood chemistry variance or blood, saliva, hair, urine, stool, fingernail, height, weight and skin sampling analysis chemistry variance outside of target ranges depends on the term A in 1410 which is the user's preference index. More dietary sensitive foodies or user's may have a higher term A index value as their blood, saliva, hair, urine, stool, fingernail, height, weight and skin sampling analysis chemistry is disadvantaged more by blood, saliva, hair, urine, stool, fingernail, height, weight and skin sampling analysis chemistry variance and out of range blood, saliva, hair, urine, stool, fingernail, height, weight and skin sampling analysis chemistry. Foodie's or user's may pick meals or portfolios of ingredients based on the highest F(foodie score) in the equation 1410. In some embodiments, search recipe or food and beverage combinations may be node ranked based on the distance of the food combination portfolio value and the foodie utility function 1410 or a plurality of other factors. If a food ingredient or portfolio of ingredients has no variance to blood chemistry of the user then a selection will have a utility or Foodie Score of the expected blood chemistry without variance as the sigma term in equation 1410 is equal to zero. Equation 1410 provides a benchmark for the system and method to evaluate meals effect on blood chemistry. In the implementation of the method according to equation 1410, the term A determines preferences of the user which then may cause as certain meal to be accepted or rejected based upon the effect to blood, saliva, hair, urine, stool, fingernail, height, weight and skin sampling analysis chemistry.

The implementation of the system and method is further represented in equations 1420 to take a simple two state case of blood chemistry for an exemplary user. If a user has an initial blood, saliva, hair, urine, stool, fingernail, height, weight and skin sampling analysis chemistry (each biomarker may be represented as short form "blood chemistry") represented as a vector of attributes and assume two possible results after eating an ingredient or a portfolio of ingredients as a meal with a vector of blood, saliva, hair, urine, stool, fingernail, height, weight and skin sampling analysis chemistry attributes. The probability of state one is p for state of Blood Chemistry 1 and a probability of (1-p) for the state two of blood chemistry 2. Accordingly, the expected value of blood chemistry as illustrated in the set of equations 1430 is E(Blood chemistry) equals probability p multiplied by blood, saliva, hair, urine, stool, fingernail, height, weight and skin sampling analysis chemistry state 1 plus probability (1-p) multiplied by blood, saliva, hair, urine, stool, fingernail, height, weight and skin sampling analysis chemistry state 2. The variance or sigma squared of the blood, saliva, hair, urine, stool, fingernail, height, weight and skin sampling analysis chemistry is represented in 1440.

Figures 15A, 15B:
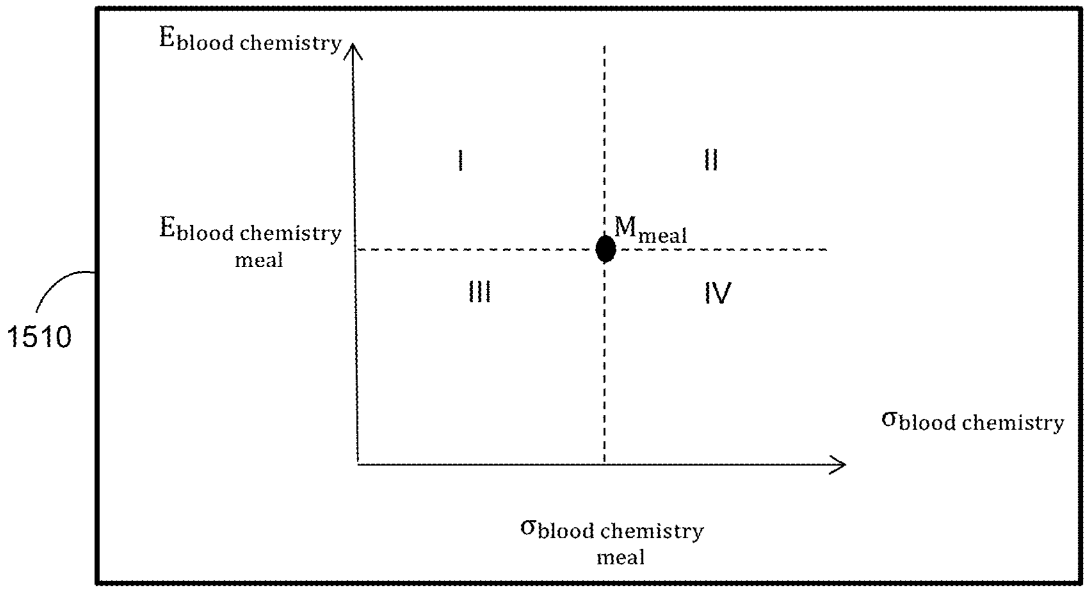
FIGS. 15A and 15B illustrate the embodiment of the method and system in FIG. 15A representing the tradeoff between the standard deviation of blood, saliva, hair, urine, stool, fingernail, height, weight and skin sampling analysis chemistry of a meal and the expected return of the blood, saliva, hair, urine, stool, fingernail, height, weight and skin sampling analysis chemistry of a meal while 15B represents the inequality condition.

The embodiment of the method and system in FIG. 15A represents the tradeoff between the standard deviation of blood, saliva, hair, urine, stool, fingernail, height, weight and skin sampling analysis chemistry of a meal and the expected return of the blood, saliva, hair, urine, stool, fingernail, height, weight and skin sampling analysis chemistry of a meal 1510. Meal M 1510 is preferred by Foodies with a high term A index value 1410 to any alternative meal in quadrant IV 1510 because the expected value of the blood chemistry of the meal is expected to be equal to or greater than any meal in quadrant IV and a standard deviation of the meal blood chemistry is smaller than any meal in that quadrant. Conversely, any meal M in quadrant I is preferable to meal M 1510 because its expected blood chemistry is higher than or equal to meal M 1510 and the standard deviation of the blood chemistry of the meal M is equal to or smaller than meal M 1510. FIG. 15B represents the inequality condition. Accordingly, if the expected value of the blood chemistry of a certain meal 1 is greater than or equal to the expected value of the blood chemistry of a certain meal 2 1520 and the standard deviation of the blood chemistry of a certain meal 1 is less than or equal to the standard deviation of the blood chemistry of a certain meal 2 1520, at least one inequality is strict which rules out inequality 1520.

Figures 16A, 16B:
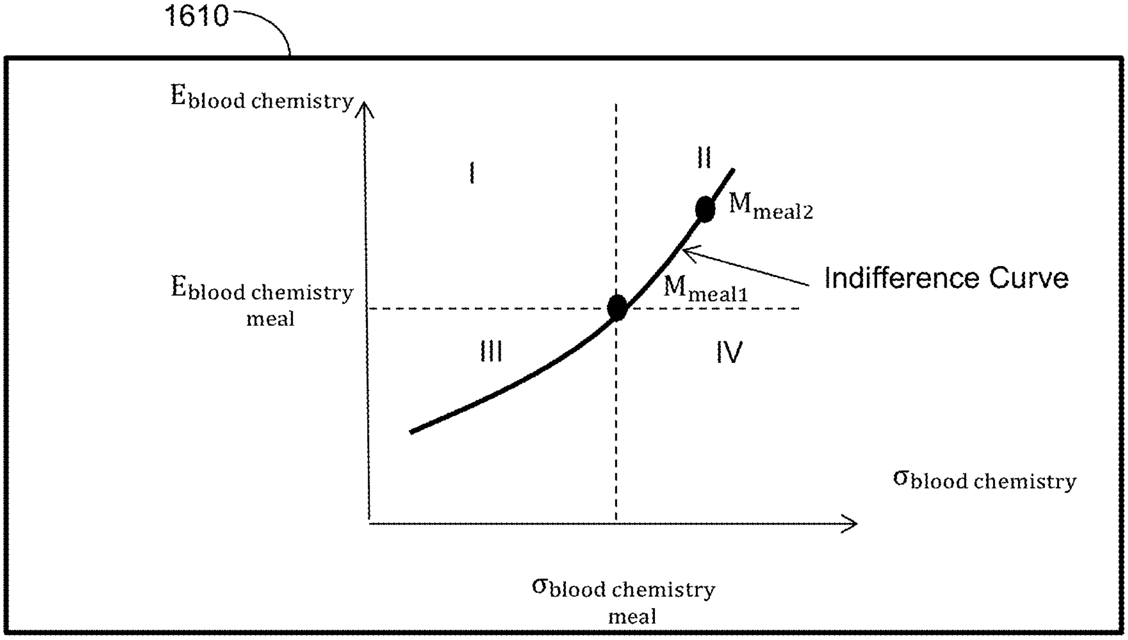
FIG. 16A in the form of a graph and 16B in the form of a table illustrates the points along a Foodies indifference curve where meals have equal utility to the user or Foodie.

The embodiment of the method and system in FIG. 16A supposes a Foodie identifies all the meals that are equally attractive from a utility and blood chemistry perspective to meal M1 1610, starting at point meal M1 1610, an increase in standard deviation of the blood chemistry of the meal lowers utility and must be compensated for by an increase in the expected value of the blood chemistry. Thus meal M2 is equally desirable to the Foodie as meal M1 along the indifference curve 1610. Foodies are equally attracted to meals with higher expected value of blood chemistry and higher standard deviation of blood chemistry as compared to meals with lower expected value of blood chemistry and lower standard deviation of blood chemistry along the indifference curve 1610. Equally desirable meals lie on the indifference meal curve that connects all meals with the same utility value 1610.

The embodiment of the method and system in FIG. 16B examines meals along a Foodies indifference curve with utility values of several possible meals for a Foodie with a term A index value of 4. 1620. The table of combinations of meals 1620 illustrates as one embodiment an expected value of blood chemistry of a meal index of 10 and a standard deviation of the blood chemistry of the meal of 20% 1620. Accordingly the Foodie Score or utility function is therefore 10 minus 0.005 multiplied by 4 multiplied by 400 equals 2 as a utility score. FIG. 16B also illustrates 3 additional examples of various expected values of meal blood chemistry and standard deviation of a meals blood chemistry 1620.

FIG. 14A, FIG. 14B, FIG. 15A, FIG. 15B, FIG. 16A, FIG. 16B discuss the blood chemistry of a meal for a particular Foodie. Such meals are composed of various types of ingredients. Foodies may eat single ingredients or meals which combine ingredients. In some embodiments, adding a certain ingredient increased the utility of a Foodie's blood chemistry, while in some embodiments adding an ingredient decreases the utility. In many contexts, "Health Food" offsets the effects of "Unhealthy Food". In one embodiment, dark chocolate is a power source of antioxidants which raises the utility of the blood chemistry. Chocolate may raise HDL cholesterol and protect LDL Cholesterol against oxidization. Too much chocolate may lower the utility of blood chemistry as it is high in saturated fat and sugar. Excessive sugar spikes the blood glucose chemistry which contributes to calories that do not have much nutrient value for the blood chemistry utility function which puts as risk weight gain and other health complications. In one implementation of the method and system, a Foodie may think it is counterintuitive adding a seemingly indulgent ingredient or recipe that may actually increase the blood chemistry performance as it can reduce the build-up of unwanted attributes and reduce the risk or standard deviation of the Foodie's blood chemistry towards and unwanted outcome. Although chocolate in and of itself may have an uncertain outcome and a negative effect on blood chemistry. Chocolate combined with other ingredients and recipes may have an overall benefit towards blood chemistry. The helpful effects come from a negative correlation of individual ingredients. The negative correlation has the effect of smoothing blood chemistry variance for a certain Foodie user.

The embodiment of the method and system in FIG. 17A examines one exemplary probability distribution of a particular ingredient affecting the blood chemistry of a Foodie or user 1710. State 1 probability of the rapini ingredient is 0.5 in table 1710 and the expected value of the rapini ingredient is to increase the blood chemistry by 25% towards the target blood chemistry range 1710, State 2 probability of the rapini ingredient is 0.3 in table 1710 and the expected value of the rapini ingredient is to increase the blood chemistry by 10% towards the target blood chemistry range 1710, State 3 probability of the rapini ingredient is 0.2 in table 1710 and the expected value of the rapini ingredient is to decrease the blood chemistry by 25% towards the target blood chemistry range 1710. Accordingly the effect on the Foodie's blood chemistry is the mean or expected return on blood chemistry of the ingredient is a probability weighted average of expected return on blood chemistry in all scenarios 1720. Calling Pr(s) the probability scenario s and r(s) the blood chemistry return in scenario s, we may write the expected return E(r) of the ingredient on blood chemistry, as is done in 1720. In FIG. 17B applying the formula of expected return of rapini on blood chemistry 1720 with the three possible scenarios in 1710 the expected return of rapini on blood chemistry of the Foodie is 10.5% toward the target range in example 1720. The embodiment of the method and system in FIG. 17C illustrates the variance and standard deviation of rapini on blood chemistry is 357.25 for variance and 18.99% for standard deviation 1730.

Exemplary embodiments of scenario probabilities vary amongst blood types and composites so the method and system is not limited to a single set of weights, but rather the system learns new weights using neural network probability weightings with iterative feedback from blood sampling to ascertain recursive effects of food chemistry onto blood chemistry.

In an exemplary embodiment in FIG. 18A, the blood chemistry of a vector of ingredients is the weighted average of the blood chemistry of each individual ingredient, so the expected value of the blood chemistry of the meal is the weighted average of the blood chemistry of each individual ingredient 1810. In the exemplary two ingredient combination of rapini and chocolate in 1810, the expected value of the combined blood chemistry is 7.75% toward the target blood chemistry range. The weight of an ingredient may be represented to incorporate serving size and calorie count as part of the measure 1810 of how ingredients affect blood chemistry.

In an exemplary embodiment in FIG. 18B, the standard deviation of the blood chemistry of the combined ingredients is represented in 1820.

Because the variance reduction in the combination since the foods were not perfectly correlated, the exemplary implementation of the method and system illustrates that a Foodie or User may be better off in their blood chemistry by adding ingredients which have a negative correlation yet positive expected value gain to blood chemistry because the variance of the blood chemistry has been reduced. To quantify the diversification of various food ingredients we discuss the terms of covariance and correlation. The covariance measures how much the blood chemistry of two ingredients or meals move in tandem. A positive covariance means the ingredients move together with respect to the effects on blood chemistry. A negative covariance means the ingredients move inversely with their effect on blood chemistry. To measure covariance we look at surprises of deviations to blood chemistry in each scenario. In the following implementation of the method and system as stated in 1830 the product will be positive if the blood chemistry of the two ingredients move together across scenarios, that is, if both ingredients exceed their expectations on effect on blood chemistry or both ingredients fall short together. If the ingredients effect on blood chemistry move in such a way that when Rapini has a positive effect on blood chemistry and chocolate has a negative effect on blood chemistry then the product of the equation in 1830 would be negative. Equation 1840 in FIG. 18D is thus a good measure of how the two ingredients move together to effect blood chemistry across all scenarios which is defined as the covariance.

In an exemplary embodiment in FIG. 19A, an easier statistic to interpret than covariance is the correlation coefficient which scales the covariance to a value between negative 1 (perfect negative correlation) and positive 1 (perfect positive correlation). The correlation coefficient between two ingredients equals their covariance divided by the product of the standard deviations. In FIG. 19A, using the Greek letter rho, we find in equation 1910 the formula for correlation in an exemplary embodiment. The correlation equation 1910 can be written to solve for covariance or correlation. Studying equation 1910, one may observe that foods which have a perfect correlation term of 1, have their expected value of blood chemistry as just the weighted average of the any two ingredients. If the correlation term in 1910 has a negative value, then the combination of ingredients lowers the standard deviation of the combined ingredients. The mathematics of equations 1910 and 1920 show that foods can have offsetting effects which can help overall target blood chemistry readings and health. Combinations of ingredients where the ingredients are not perfectly correlated always offer a better combination to reduce blood chemistry volatility while moving more efficiently toward target ranges.

In an exemplary embodiment in FIG. 19B, the impact of the covariance of individual ingredients on blood chemistry is apparent in the following formula 1920 for blood chemistry variance.

The most fundamental decision of a Foodie is how much of each food should you eat? And how will it affect my health and blood chemistry. Therefore one implementation of the method and system covers the blood chemistry tradeoff between combinations of ingredients or dishes or various portfolios of ingredients or recipes or meals or prepared dishes or restaurant entrees.

In an exemplary embodiment in FIG. 19C, recalling the Foodie Score or Utility equation of a user 1410, the Foodie attempts to maximize his or her utility level or Foodie score by choosing the best allocation of a portfolio of ingredients or menu selection written as equation 1930.

Constructing the optimal portfolio of ingredients or a recipe or menu or meal is a complicated statistical task. The principle that the method and system follow is the same used to construct a simple two ingredient recipe or combination in an exemplary scenario. To understand the formula for the variance of a portfolio of ingredients more clearly, we must recall that the covariance of an ingredient with itself is the variance of that ingredient such as written in FIG. 20A. Wing1 and Wing2 2010 are short for the weight associated with ingredient or meal 1 and ingredient or meal 2. The matrix 2010 is simply the bordered covariance matrix of the two ingredients or meals.

In the embodiment of the method and system in FIG. 20B, the descriptive statistics for two ingredients are listed as the expected value and standard deviation as well as covariance and correlation between the exemplary ingredients 2020. The parameters for the joint probability distribution of returns is shown in FIG. 20B.

Figures 21A, 21B:
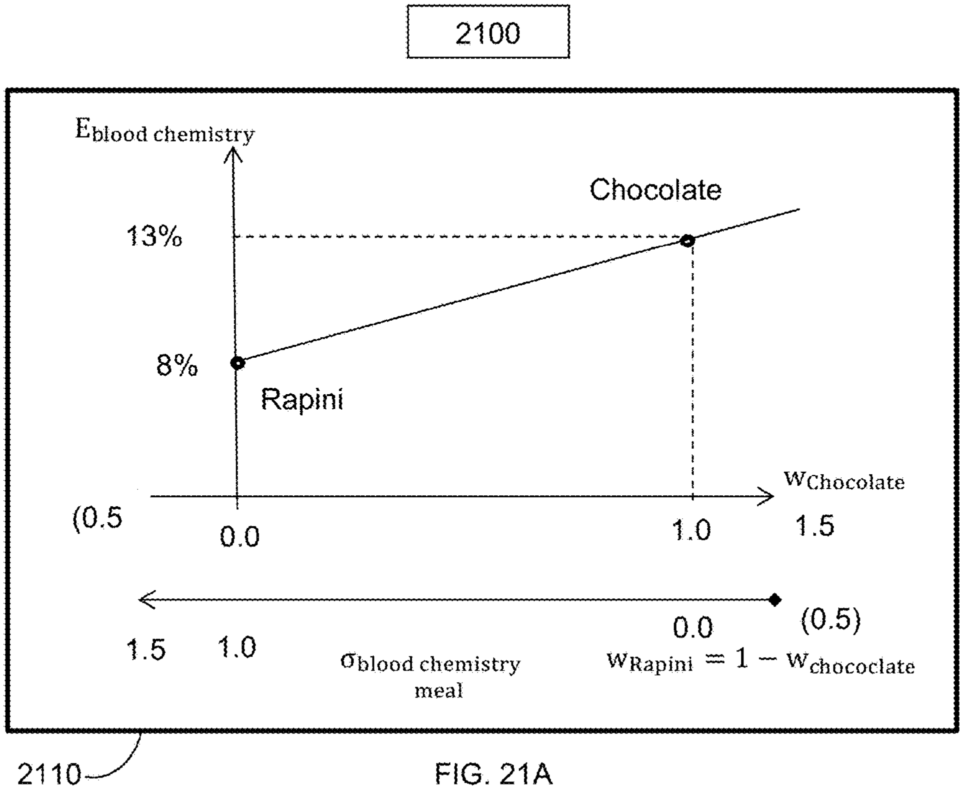
FIGS. 21A and 21B illustrate an exemplary scenario of an experiment with different proportions to observe the effect on the expected blood, saliva, hair, urine, stool, fingernail, height, weight and skin sampling analysis chemistry and variance of blood chemistry with various weightings.

The embodiments of the method and system in FIG. 21A and FIG. 21B illustrate an exemplary scenario of experiment with different proportions to observe the effect on the expected blood chemistry and variance of blood chemistry. Suppose the proportion of the meal weight of rapini is changed. The effect on the blood chemistry is plotted in FIG. 21A. When the proportion of the meal that is rapini varies from a weight of zero to one, the effect on blood chemistry change toward the target goes from 13% (expected blood chemistry of chocolate) to 8% (expected blood chemistry of rapini). Of course, varying proportions of a meal also has an effect on the standard deviation of blood chemistry. FIG. 21B presents various standard deviation for various weights of rapini and chocolate 2120.

Figure 22A:
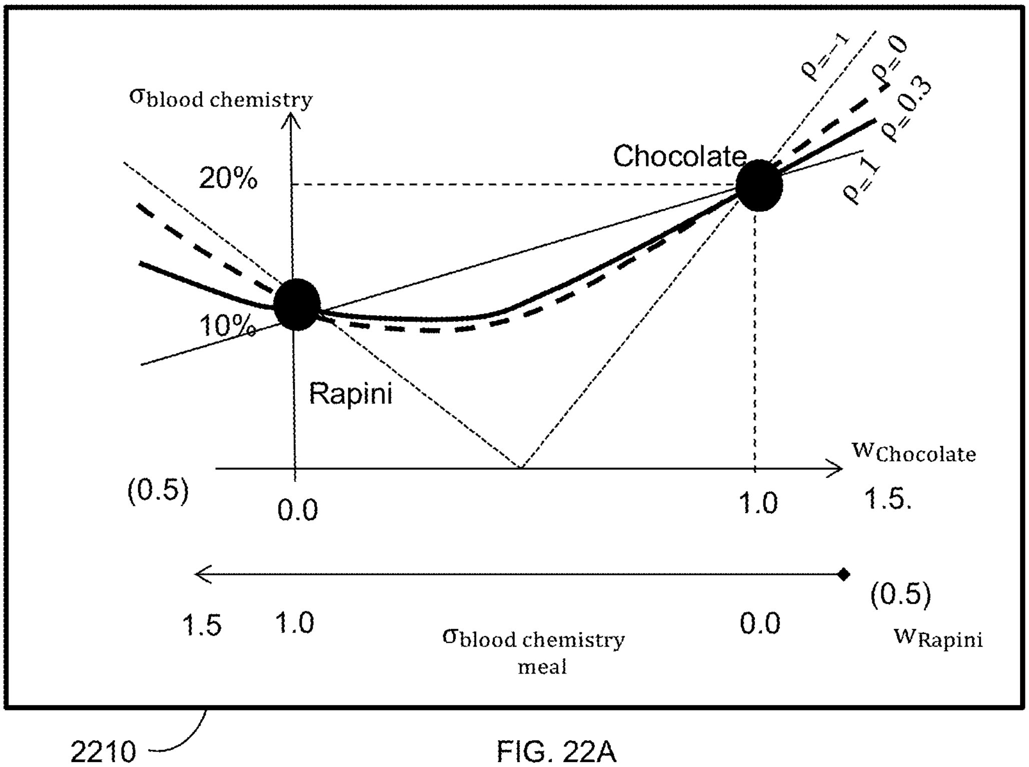
FIGS. 22A and 22B illustrate an exemplary case of the meal combination blood, saliva, hair, urine, stool, fingernail, height, weight and skin sampling analysis chemistry standard deviation when correlation rho is at 0.30.

In the exemplary case of the meal combination blood chemistry standard deviation when correlation rho is at 0.30 in FIG. 22A. The thick curved black line labeled rho=0.3 in FIG. 2210. Note that the combined meal blood chemistry of rapini and chocolate is a minimum variance combination that has a standard deviation smaller than that of either rapini or chocolate as individual ingredients. FIG. 22A highlights the effect of ingredient combinations lowering overall standard deviation. The other three lines in FIG. 22A show how blood chemistry standard deviation varies for other values of the correlation coefficient, holding the variances of the ingredients constant. The dotted curve where rho=0 in FIG. 22A depicts the standard deviation of blood chemistry with uncorrelated ingredients. With the lower correlation between the two ingredients, combination is more effective and blood chemistry standard deviation is lower. We can see that the minimum standard deviation of the meal combination in table 2120 shows a value of 10.29% when rho=0. Finally the upside down triangular broken dotted line represents the potential case where rho=−1 and the ingredients are perfectly negatively correlated 2210. In the rho=−1 case 2210, the solution for the minimum variance combination is a rapini weight of 0.625 and a chocolate weight of 0.375 in FIG. 22A. The method and system can combine FIG. 21A and FIG. 22A to demonstrate the relationship between the ingredients combination's level of standard deviation to blood chemistry and the expected improvement or decline in expected blood chemistry given the ingredient combination parameters 2220.

Figure 22B:
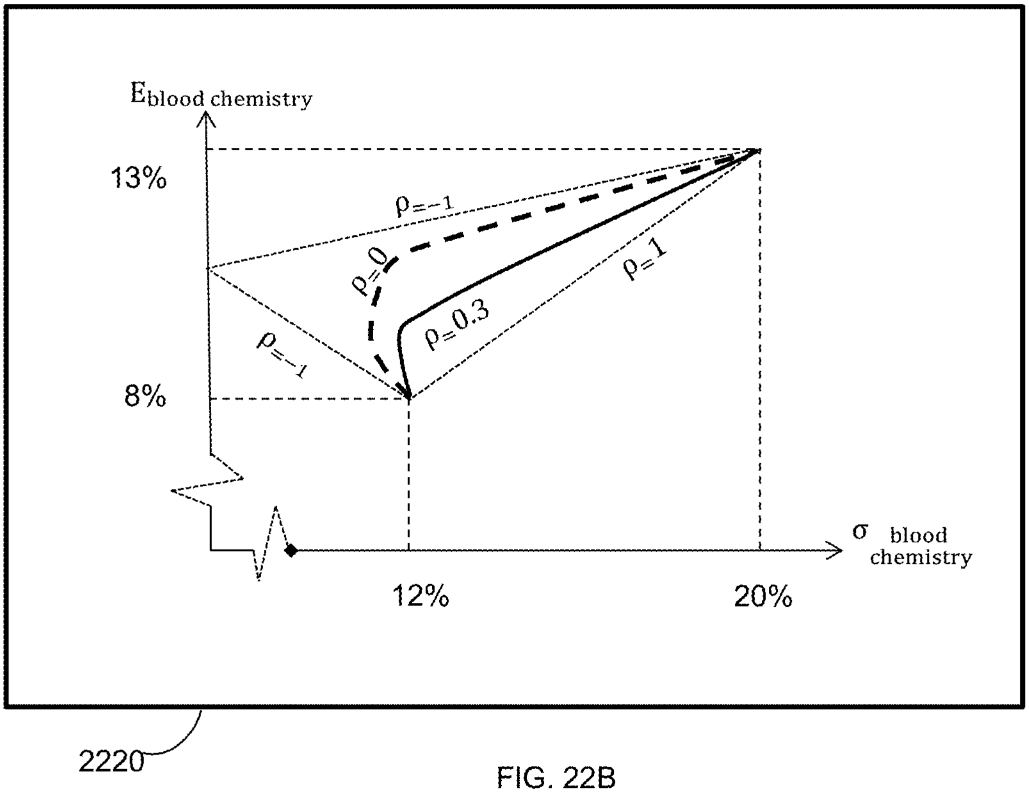

The embodiment illustrated in FIG. 22B shows for any pair of ingredients or meals which may be illustrated for an exemplary case, but not limited to the exemplary case w(chocolate) and w(rapini), the resulting pairs of combinations from 2210 and 2120 and 2110 are plotted in 2220. The solid curved line in 2220 labeled with rho=0.3 shows the combination opportunity set while correlation equals 0.3. The name opportunity set is used because it shows the combination of expected blood chemistry and standard deviation of blood chemistry of all combinations that can be constructed from the two available ingredients. The broken dotted lines show the combination opportunity set for the other values of the correlation coefficient. The line farthest to the right, which is the straight line connecting the combinations where the term rho equals one, shows there are no benefits to blood chemistry from combinations between ingredients where the correlation between the two ingredients is perfectly positive or where the term rho equals one. The opportunity set is not "pushed" to the northwest. The curved dotted line to the left of the curved solid line where the term rho equals zero shows that there are greater benefits to blood chemistry when the correlation coefficient between the two ingredients is zero than when the correlation coefficient is positive 2220. Finally the broken line where the term rho equals negative one shows the effect of perfectly negative correlation between ingredients. The combination opportunity set is linear, but offers the perfect offset between ingredients to move toward target blood chemistry 2220. In summary, although the expected blood chemistry of any combination of ingredients is simply the weighted average of the ingredients expected blood chemistry, this is not true for the combination of ingredients standard deviation. Potential benefits from combinations of ingredients arise when correlation is less than perfectly positive. The lower the correlation coefficient, the greater the potential benefit of combinations. In the extreme case of perfect negative correlation between ingredients, the method and system show a perfect offset to blood chemistry and we can construct a zero-variance combination of ingredients 2220.

Suppose the exemplary case where the Foodie wishes to select the optimal combination from the opportunity set. The best combination will depend upon the Foodie's preferences and aversion to the standard deviation of ingredients. Combinations of ingredients to the northeast in FIG. 22B provide higher movements towards expected target blood chemistry, but impose greater levels of volatility of ingredients on blood chemistry. The best trade-off among these choices is a matter of personal preference. Foodie's with greater desire to avoid volatility in their blood chemistry will prefer combinations of ingredients in the southwest, with lower expected movement toward target blood chemistry, but lower standard deviation of blood chemistry 2220.

Figures 23A, 23B:
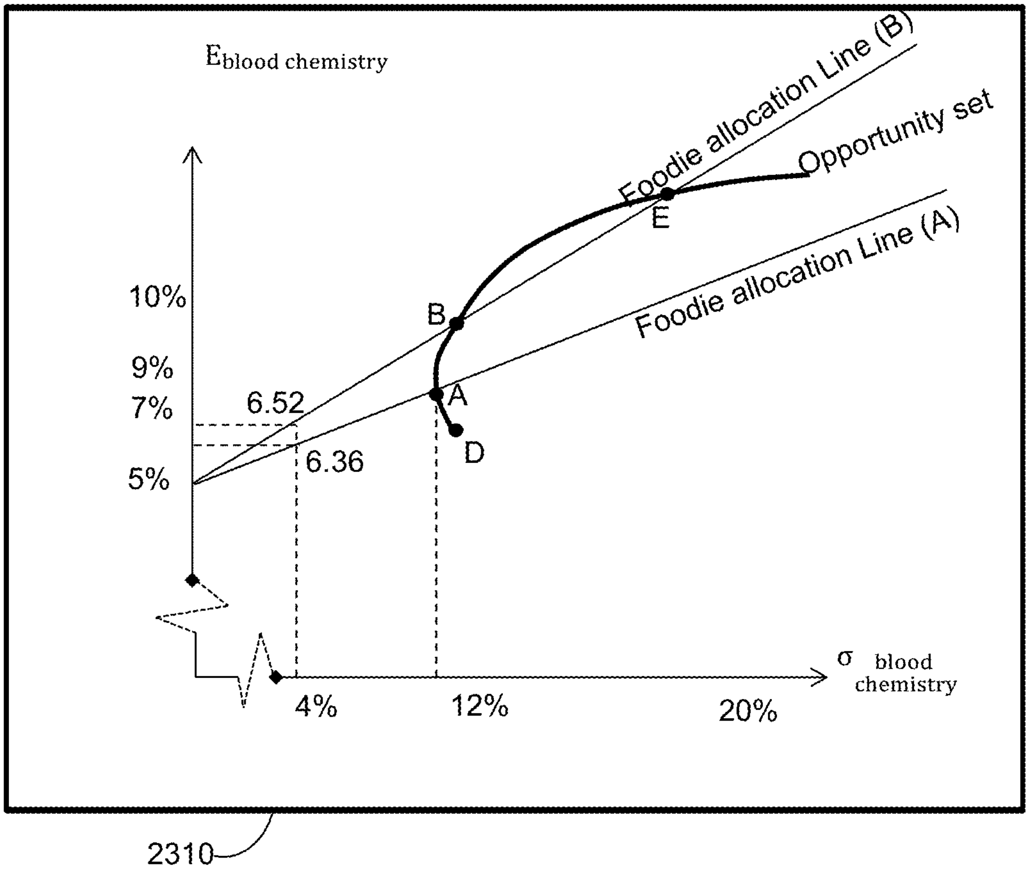
FIGS. 23A and 23B illustrate the opportunity set generated from the joint probability distribution of the combination of ingredients of rapini and chocolate using the data from FIG. 20B as well as the slope of the reward to variability ratio or Foodie allocation line (A).

In the embodiment illustrated in FIG. 22B, most Foodie's recognize the really critical decision is how to divvy up their selection amongst ingredients or meal combinations. In the embodiment of the method and system in FIG. 23A, the exemplary diagram is a graphical solution. FIG. 23A shows the opportunity set generated from the joint probability distribution of the combination of ingredients rapini and chocolate using the data from FIG. 21B. Two possible allocation lines are drawn and labeled "Foodie allocation line". The first Foodie allocation line (A) is drawn through the minimum variance ingredient combination point A which is divided as 82% rapini and 18% chocolate. The ingredient combination has an expected target blood chemistry movement of 8.9% and its standard deviation is 11.45% blood chemistry 2310. The reward to variability ratio or slope of the Foodie allocation line combining a zero variance ingredient (which may be certain types of water) with rapini and chocolate with the aforementioned weights of 82% rapini and 18% chocolate, forms an equation listed in FIG. 23B. Accordingly the exemplary slope 2320 of Foodie Allocation Line (A) is 0.34. Considering the embodiment in FIG. 23A of Foodie allocation line (B), the ingredient combination was 70% rapini and 30% chocolate, the expected movement towards target blood chemistry is 9.5%. Thus the reward to variability ration or slope of Foodie allocation line(B) is 9.5 minus 5 divided by 11.7 which equals 0.38 or a steeper slope as illustrated in FIG. 23A. If the Foodie allocation line (B) has a better reward to variability ratio than the Foodie allocation line (A), then for any level of standard deviation that a Foodie is willing to bear, the expected target blood chemistry movement is higher with the combination of point B. FIG. 23B illustrates the aforementioned exemplary case, showing that Foodie allocation line (B) intersection with the opportunity set at point B is above the Foodie allocation line (A) intersection with the opportunity set point A. In this case, point B allocation combination dominates point A allocation combination. In fact, the difference between the reward to variability ratio is the difference between the two Foodie allocation line (A) and (B) slopes 2320. The difference between the two Foodie allocation line slopes is 0.38−0.34=0.04. This means that the Foodie gets four extra basis points of expected blood chemistry movement toward the target with Foodie allocation line (B) for each percentage point increase in standard deviation of blood chemistry 2310. If the Foodie is willing to bear a standard deviation of blood chemistry of 4%, the Foodie can achieve a 5.36% (5+4×0.34) expected blood chemistry movement to the target range along Foodie allocation line (A) and with Foodie allocation line (B) the Foodie can achieve an expected movement of blood chemistry to the target of 6.52% (5+4×0.38) 2310. Why stop at point B? The Foodie can continue to ratchet up the Foodie allocation line until it ultimately reaches the point of tangency with the Opportunity set 2310. This aforementioned exemplary scenario in FIG. 23A must yield the Foodie allocation line with the highest feasible reward to variability ratio.

The embodiment illustrated in exemplary scenario FIG. 24A shows the highest sloping Foodie allocation line (C) at point P intersecting with the opportunity set. Point P is the tangency combination of ingredients where the expected blood chemistry target movement is the highest relative to the opportunity set and standard deviation of ingredients or meal combinations 2410. The optimal combination or allocation of ingredients is labeled point P. At Point P, the expected blood chemistry movement to the target is 11% while the standard deviation of point P is 14.2%. In practice, we obtain the solution to the method and system with a computer program with instructions to perform the calculations for the Foodie 2410. The method process to obtain the solution to the problem of the optimal mix of ingredients or dish combinations of weight rapini and weight chocolate or any other combination of ingredients is the objective of the method and system. In some embodiments, node rankings from the food and beverage database may be determined by the relative ranking of the ratio of expected blood chemistry target to the opportunity set and standard deviation of the ingredients and meal combinations 2410.

There are many approaches toward optimization which are covered under method and system to optimize blood chemistry through food ingredients which are may be utilized for computational efficiency, but the method and system may use as one approach of many approaches where the method finds the weights for various ingredients that result in the highest slope of the Foodie allocation line (C) 2410. In other words, the method and system may find the weights that result in the variable combination with the highest reward to variability ratio. Therefore the objective function of the method and system may maximize the slope of the Foodie allocation line for any possible combination of ingredients 2410. Thus the objective function of the method and system may show the slope as the ratio of the expected blood chemistry of the combination of ingredients less the blood chemistry of a zero standard deviation blood chemistry ingredient (perhaps water) divided by the standard deviation of the combination of ingredients illustrated in FIG. 24B. For the combination of ingredients with just two ingredients, the expected blood chemistry movement toward the target and standard deviation of blood chemistry of the combination of ingredients is illustrated in FIG. 24B. When the method and system maximize the objective function which is the slope of the foodie allocation line subject to the constraint that the combination weights sum to one or one hundred percent 2420. In other words the weight of the rapini plus the weight of the chocolate must sum to one. Accordingly, the method and system may solve a mathematical problem formulated as FIG. 25A which is the standard problem in calculus. Maximize the slope of the foodie allocation line subject to the condition that the sum of the weight of all the ingredients will sum to one.

In the embodiment case illustrated in FIG. 25B, the exemplary case may include two ingredients or meal combinations, but the system and method are able to process any amount of ingredients or meal combinations with an extension of the calculus equations 2510. In the exemplary case of only two ingredients, FIG. 25B illustrates the solution for the weights of the optimal blood chemistry combination of ingredients. Data from 2110, 2120, 2310, 2410, 2420, 2510 have been substituted in to give the weights of rapini and chocolate in FIG. 25B an exemplary case. The expected blood chemistry has moved 11% toward the target blood chemistry which incorporates the optimal weights for rapini and chocolate in this exemplary case 2410 and the standard deviation is 14.2% in FIG. 24A. The foodie allocation line using the optimal combination in 2510 and 2520 has a slope of $0.42=(11-5)/14.2$ which is the reward to variability ratio of blood chemistry. Notice how the slope of the foodie allocation line exceeds the slope of foodie allocation line (B) and foodie allocation line (A) in FIG. 23A as it must if it is to be the slope of the best feasible foodie allocation line. A foodie with a coefficient term A in FIG. 14A equal to 4 would then make a combination as follows in FIG. 25C. Thus the foodie would select 74.39% of her/his food allocation in the combination of rapini and chocolate and 25.61% in water or an ingredient which has zero standard deviation to blood chemistry 2530. Of the 74.39% of the food ingredient selection, 40% of the 74.39% or ($0.4\times 0.7439=0.2976$) would go to rapini and 60% of 74.39% or ($0.60\times 0.7439=0.4463$) would go toward chocolate. The graphical solution of the equations in FIG. 25A, FIG. 25B and FIG. 25C is illustrated in FIG. 26A.

Once the specific two ingredient case has been explained for the method and system, generalizing the embodiment to the case of many ingredients is straightforward. The summarization of steps are outlined in FIG. 26B.

Figure 27A:
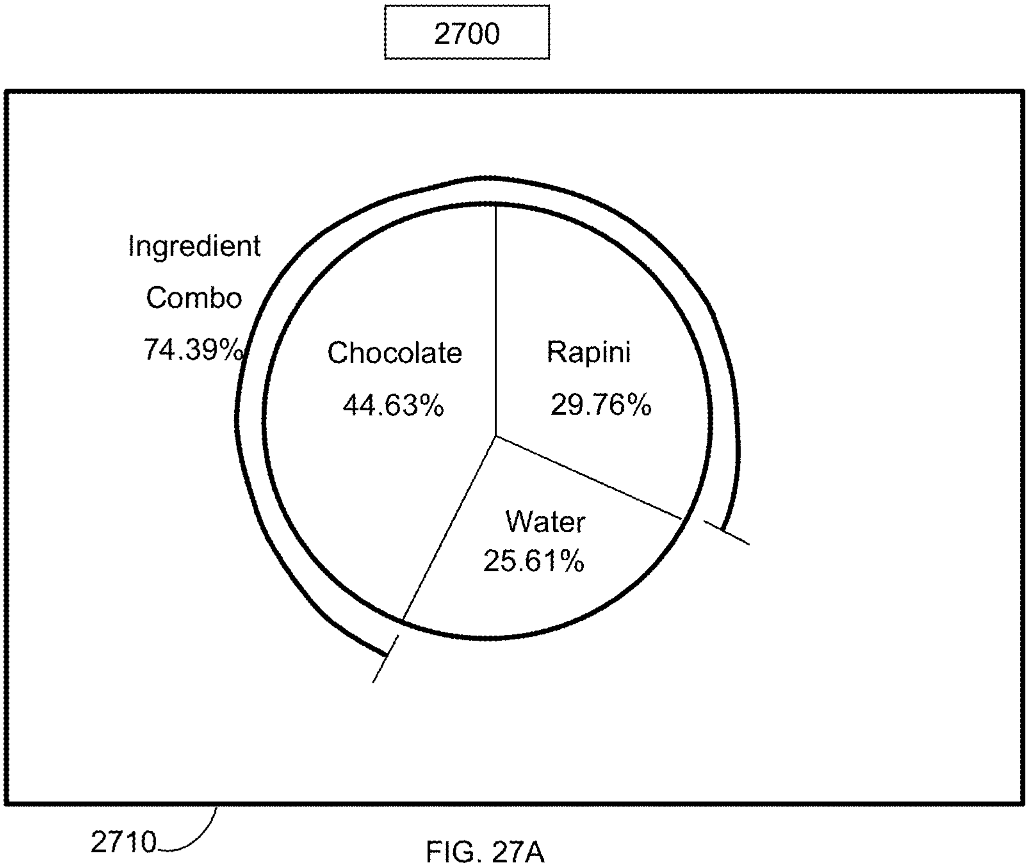
FIGS. 27A and 27B illustrate the graphical solution of the user ingredient allocation method as well as the minimum variance frontier of ingredients which is the graph of the lowest possible ingredient variance combination for a given target food chemistry and its effect on blood, saliva, hair, urine, stool, fingernail, height, weight and skin sampling analysis chemistry.

The embodiment of FIG. 27A illustrates a combination of ingredients for the optimal combination in the form of a pie chart. Before moving on it is important to understand that the two ingredients described could be meals or combinations of ingredients. Accordingly the method and system may consider the blood chemistry characteristics of single ingredients or combinations of ingredients which can then form an ingredient as a meal which would act as an ingredient which characteristics such as expected blood chemistry, variance and covariance and correlation. Accordingly there can be diversification within ingredients as some ingredients are combinations of ingredients.

Now we can generalize the two ingredient embodiment of the method and system to the case of many ingredients alongside water or an ingredient with near zero blood chemistry variance or standard deviation. As in the case of the two ingredient embodiment, the problem is solved by the method and system in three parts. First, we identify the expected blood chemistry contribution of the ingredient and standard deviation of that ingredient contribution to blood chemistry. Second, the method and system identifies the optimal combination of ingredients by finding the combination weights that result in the steepest foodie allocation line. Last, the method and system may choose an appropriate complete combination by mixing the combination of water or a zero blood chemistry standard deviation ingredient with the combination of ingredients that carry various standard deviation and correlations. The ingredient opportunities available to the Foodie must be determined in the method and system. These ingredient opportunities are summarized by the minimum variance blood chemistry frontier of ingredients. This frontier is a graph of the lowest possible combination variances that can be attained for a given combination of expected blood chemistry contribution. Given the set of data for expected blood chemistry contribution, variances and covariance's of blood chemistry and expected covariance's of blood chemistry of combinations, we can calculate the minimum blood chemistry variance combination for any targeted blood chemistry contribution. Performing such as calculation for many such expected blood chemistry combinations results in a paring between expected blood chemistry contributions and minimum variance blood chemistry contribution that offer the expected blood chemistry contributions. The plot of these expected blood chemistry contribution and standard deviation pairs are presented in FIG. 27B. Notice that all ingredients lie to the right of the frontier. This tells us that combinations that consist only of a single ingredient are inefficient relative to combinations. Adding many ingredients leads to combinations with higher expected blood chemistry contribution and lower standard deviations 2720. All the combinations in FIG. 27B that lie on the minimum variance frontier from the global minimum variance portfolio and upward, provide the best expected blood chemistry contribution and standard deviation of blood chemistry combinations and thus are candidates for the optimal combination 2720. The part of the frontier that lies above the global minimum variance combination is called the efficient frontier 2720. For any combination on the lower portion of the minimum variance frontier, there is a combination with the same standard deviation of blood chemistry but higher expected blood chemistry contribution positioned directly above it. Hence the bottom part of the minimum variance frontier is inefficient.

The second part of the optimization plan involves water or a zero standard deviation blood chemistry ingredient. As before, the method and system search for the foodie allocation line with the highest reward to variability ratio (that is the steepest slope) as shown in FIG. 26A. The foodie allocation line that is supported by the optimal combination point P 2610, is, as before, the combination that is tangent to the efficient frontier. This foodie allocation line dominates all alternative feasible lines. Therefore, combination P in FIG. 26A is the optimal ingredient combination.

Finally, the last part of the embodiment of the method and system, the Foodie chooses the appropriate mix between the optimal ingredient combination and a zero blood chemistry variance ingredient which may include water. In FIG. 26A, the point where Foodie allocation line (C) has a zero standard deviation value is where the expected blood chemistry target movement is 5% or point F 2610.

Now let us consider in the method and system each part of the combination construction problem in more detail. In the first part of the Foodie problem, the analysis of the expected blood chemistry of the ingredient, the Foodie needs as inputs, a set of estimates of expected blood chemistry target movement for each ingredient and a set of estimates for the covariance matrix which the method and system provide for the Foodie through the system application.

Suppose that the time period of the analysis for the combination of ingredients between biomarker tests was one year. Therefore all calculations and estimates pertain to a one year plan under the method and system. The database system contains the variable n ingredients where n could be any amount of ingredients. As of now, time zero, we observed the expected biomarker chemistry of the ingredients such that each ingredient is given the variable label i and an index number of n at time zero. Then the system and method determine how the ingredient effects the Foodies blood chemistry at the end of one year or time equal to one year. The covariance's of the ingredients effects on blood chemistry are usually estimated from historical data for both the Foodie and from Foodie users in the database with similar characteristics. Through the method and system, the Foodie is now armed with the n estimates of the expected effect on blood chemistry of each ingredient and then the n×n estimates in the covariance matrix in which the n diagonal elements are estimates of the variances of each ingredient and then the n squared minus n equals n multiplied by the quantity of n minus 1 off diagonal elements are the estimates of the covariances between each pair of ingredient blood chemistries. We know that each covariance appears twice in the aforementioned table, so actually we have $n(n-1)/2$ different covariance estimates. If the Foodie user considers 50 ingredients or meal combinations, the method and system needs to provide 50 estimates of expected blood chemistry results for each respective ingredient or meal combination and $(50\times 49)/2=1{,}225$ estimates of covariance's which is a daunting task without the assistance of the method and system computer application program. Once these estimates are compiled by the method and system, the expected blood chemistry and variance of any combination of ingredients with weights for any of the respective ingredients can be calculated by the general formulas in FIG. 28A.

Figure 27B:
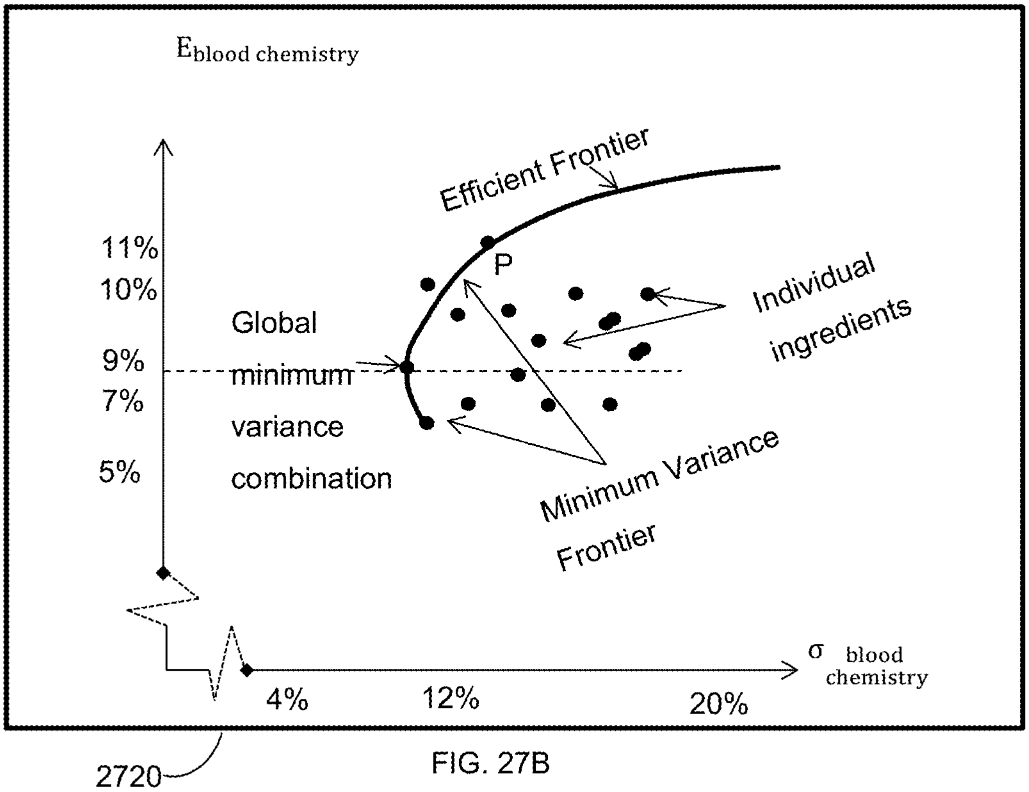
Figures 28A, 28B:
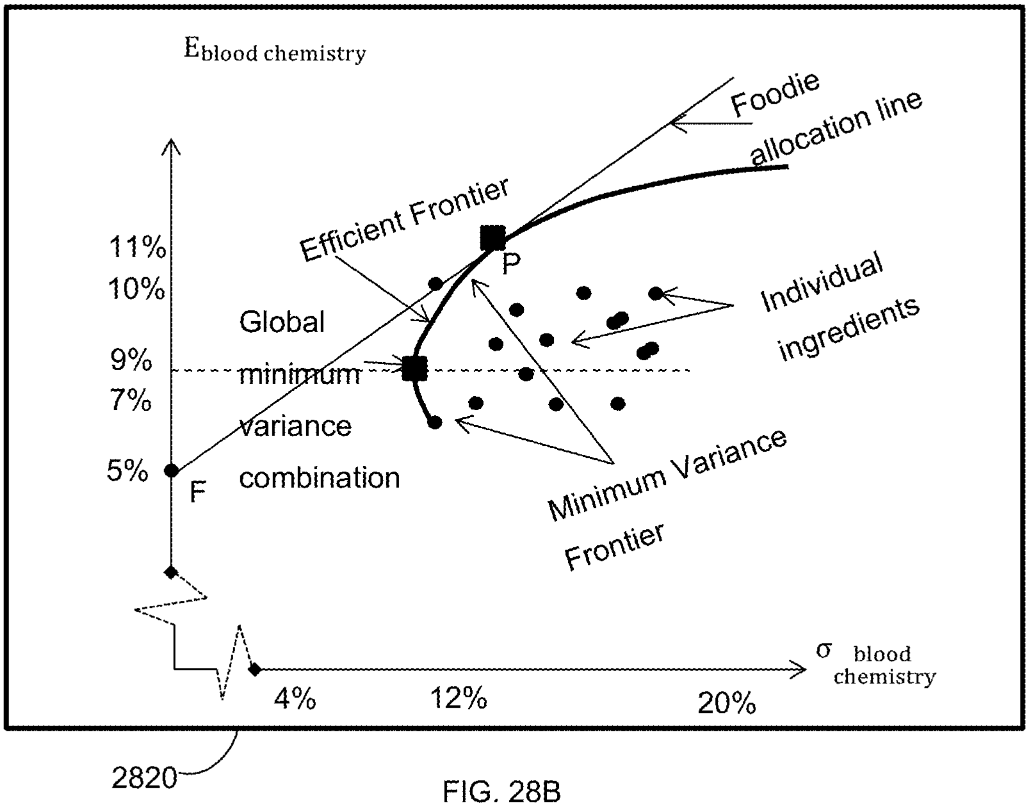
FIGS. 28A and 28B illustrate the expected movement of a users blood, saliva, hair, urine, stool, fingernail, height, weight and skin sampling analysis chemistry from the ingredient combination as well as the expected variance of blood, saliva, hair, urine, stool, fingernail, height, weight and skin sampling analysis chemistry.

The general embodiment of an exemplary case of the method and system in FIG. 28A states the expected blood chemistry toward the target blood chemistry of each ingredient and the variance of the blood chemistry of each ingredient such that the weights of each ingredient can be calculated 2810. While many people say "eat a wide variety of food" or "eat a balanced diet" or "don't put all your eggs in one basket", no method or system has attempted to accurately quantify these statements in such a way that mathematics and science can be used to easily make a map for eating. The system and method have coined the phrase, as GPS is to driving, Foodie Body or the blood and saliva to food algorithms are to eating. No longer will Foodies or user guess at how nutrition is effecting their blood and overall health, math and science will map their progress with a quantitative method and system. The principle behind the method and system is that a foodie can quantify the set of ingredient combinations that give the highest blood chemistry result to maximize human health and productivity. Alternatively, the efficient frontier in FIG. 27B is the set of ingredient combinations that minimize the variance of blood chemistry for any target blood chemistry. In some embodiments, In some embodiments, node rankings from the food and beverage database may be determined by the relative ranking of the ratio of expected blood chemistry target to the opportunity set and standard deviation of the ingredients and meal combinations which are represented by the plurality of meals or recipe combinations that are points with expected blood chemistry values and blood chemistry variances in the opportunity set from the search input term 2720. The result is the most efficient method empirically and quantitatively to consume food for human health.

The points marked by rectangles in the exemplary embodiment in FIG. 28B are the result of variance—minimization calculations in the method and system. First we draw the constraint, that is, a horizontal line at the level of required expected blood chemistry target. We then look for the combination of ingredients (point P) with the lowest standard deviation that plots on the Foodie allocation line 2820. We then discard the bottom of the minimum variance frontier below the global minimum variance combination as it is inefficient 2820 and points above the global minimum variance combination have higher blood chemistry contribution to the target, but a similar standard deviation. Restating the solution that the method and system has completed thus far. The estimate generated by the Foodie utilizing the method and system transformed ingredients and ingredient combinations into a set of expected blood chemistry statistics toward the users blood chemistry and a covariance matrix of how the ingredients are correlated. This group of estimates shall be called the input list. This input list is then fed into the optimization system and method. Before we proceed to the second step of choosing the optimal combination of ingredients for blood or saliva chemistry, some Foodies may have additional constraints. For example, many Foodies have allergies which preclude certain food ingredient types. The list of potential constraints is large and the method and system allows for the addition of constraints in the optimization method and system. Foodie users of the system and method may tailor the efficient set of ingredients to conform to any desire of the Foodie. Of course, each constraint carries a price tag in the sense that an efficient frontier constructed subject to extra constraints may offer a reward to variability ratio inferior to that of a less constrained set. The Foodie is made aware of this cost through the system and method application and should carefully consider constraints that are not mandated by law or allergies.

Proceeding to step two in the method and system, this step introduces water or a zero variance blood chemistry ingredient that has positive blood chemistry attributes. As before we ratchet up the Foodie allocation line by selecting different combinations of ingredients until combination P is reached 2820 which is the tangency point of a line from point F to the efficient frontier 2820. Ingredient combination P maximizes the reward to variability ratio, the slope of the Foodie allocation line from point F to combinations on the efficient frontier set 2820.

The method and system embodiment of the general exemplary case may be written in one form as in FIG. 29. Vectors are used to capture variable d inputs or as many inputs as are required to weight in FIG. 29. The method as system may use other techniques to express combination blood and saliva expected target chemistry and variances, but it is convenient to handle large combinations of ingredients in matrix form in FIG. 29.

Figure 30:
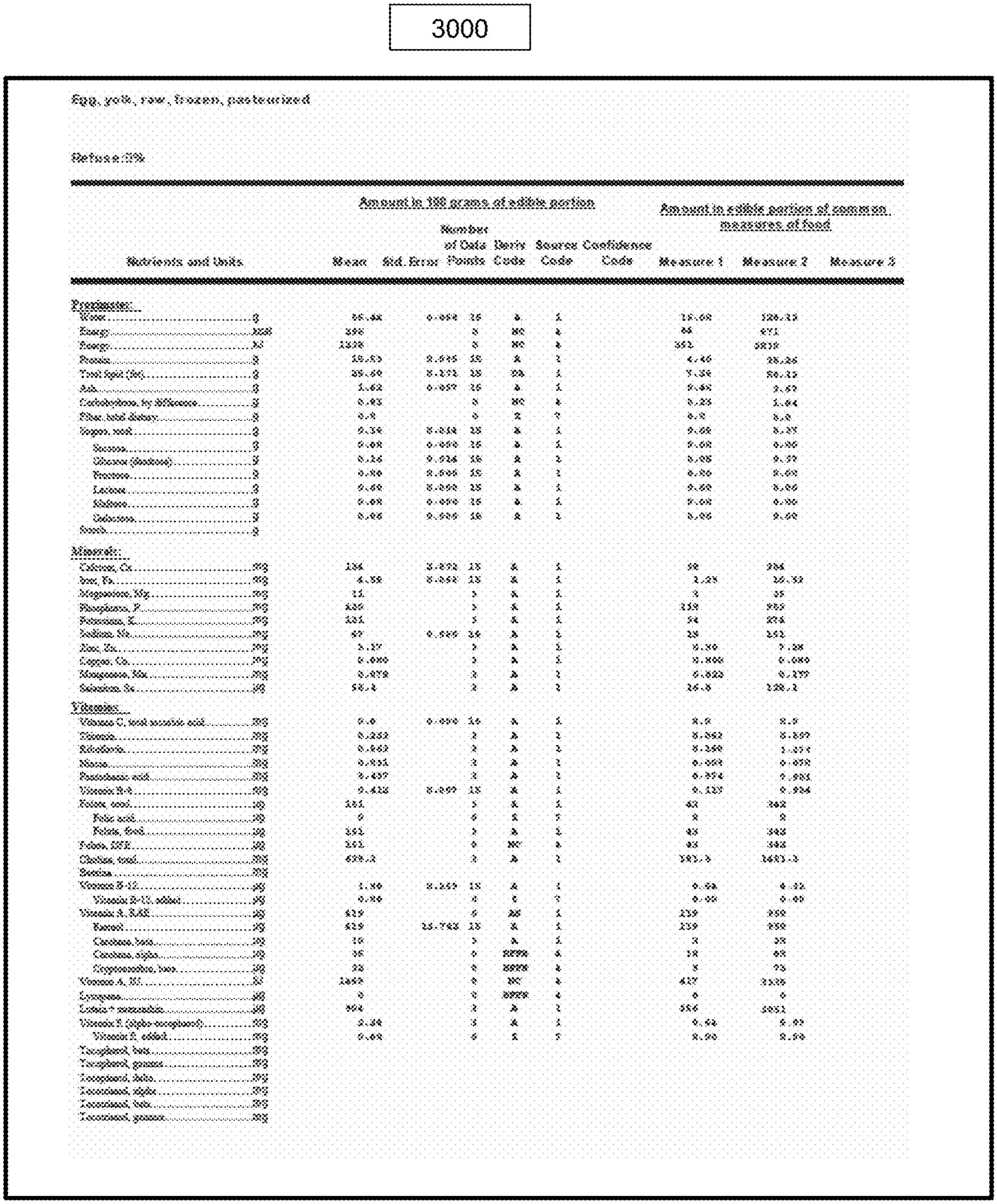
FIG. 30 illustrates a specific embodiment of the components of food chemistry elements and their expected values.

The method and system embodiment in FIG. 30, FIG. 31 and FIG. 32 illustrate one exemplary entry in the system database which measures the nutrition content and standard deviation toward blood and saliva chemistry for egg, yolk, raw, frozen or pasteurized. The method and system database for food 240 may have a mixture of United States Department of Agriculture data and proprietary merchant or cook food data that has higher degrees of differentiation in nutrition levels.

Figure 33:
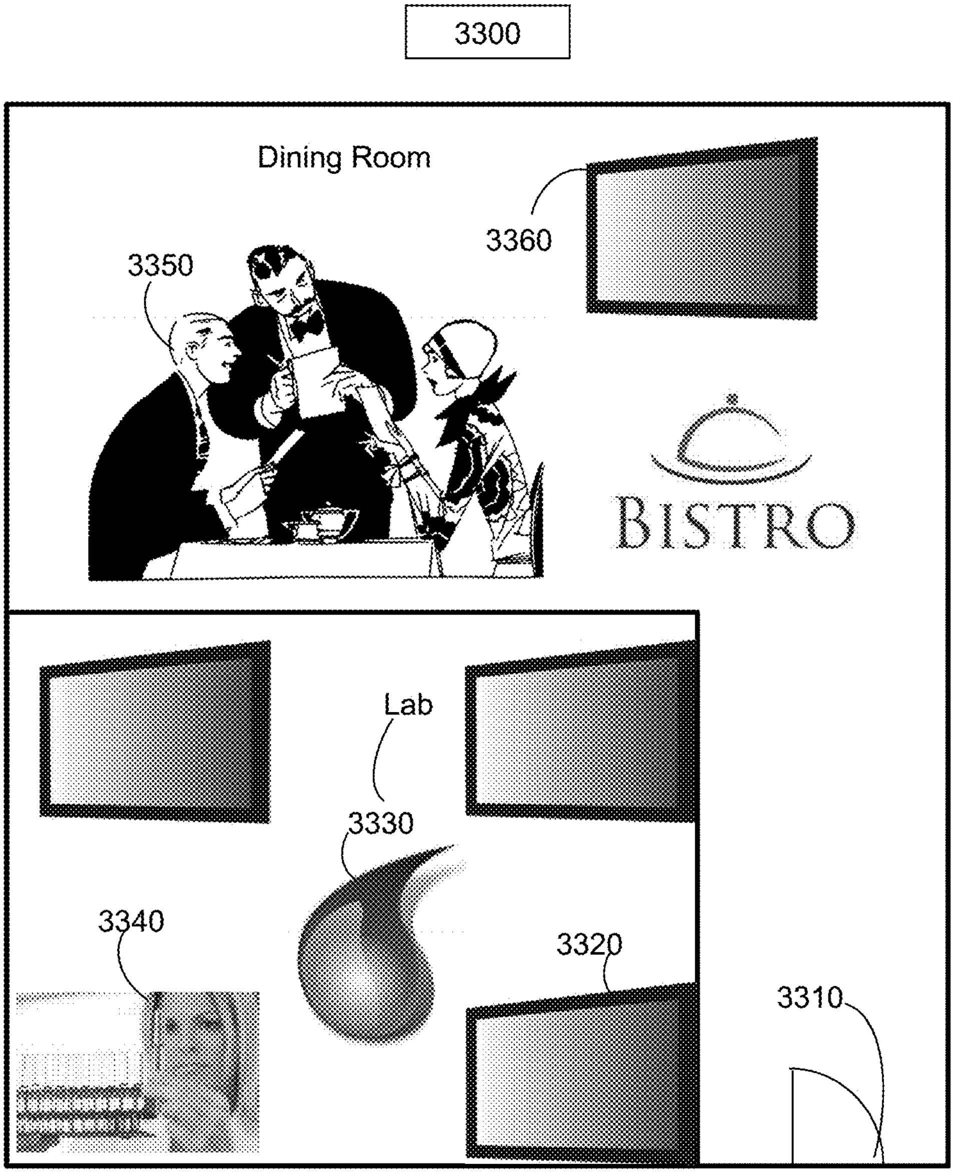
FIG. 33 illustrates a specific education center food establishment where both blood, saliva, hair, urine, stool, fingernail, height, weight and skin sampling analysis work and a restaurant that has the ability utilize the equations of the methods and teach the users how blood, saliva, hair, urine, stool, fingernail, height, weight and skin sampling analysis and food interact in the method embodiment.

The method and system embodiment illustrated in FIG. 33 may be one of many distribution and education channels where a retail concept store combines a food database laboratory and a dining experience for the foodie or user. A Foodie may walk into the door 3310 of the retail experience and be given an opportunity to move into the blood laboratory 3330 where they will be given appetizers in a high tech learning center blood lab 3330. Monitor screens or projection devices both in 2D and 3D and mixed reality or augmented reality may project visualizations of blood chemistry interactions with food chemistry 3320. After the lab technician secures a blood and saliva sample from the foodie 3340, the user may go into the dining room 3350. In the dining room of the concept retail experience 3350 Foodie experts will assist Foodies with menu selection of blood and saliva optimized food 3360. While FIG. 33 illustrates a retail concept store for the method and system, the method and system may have many outlets such as any grocery store, restaurant, computing device or food distribution point.

Figure 34:
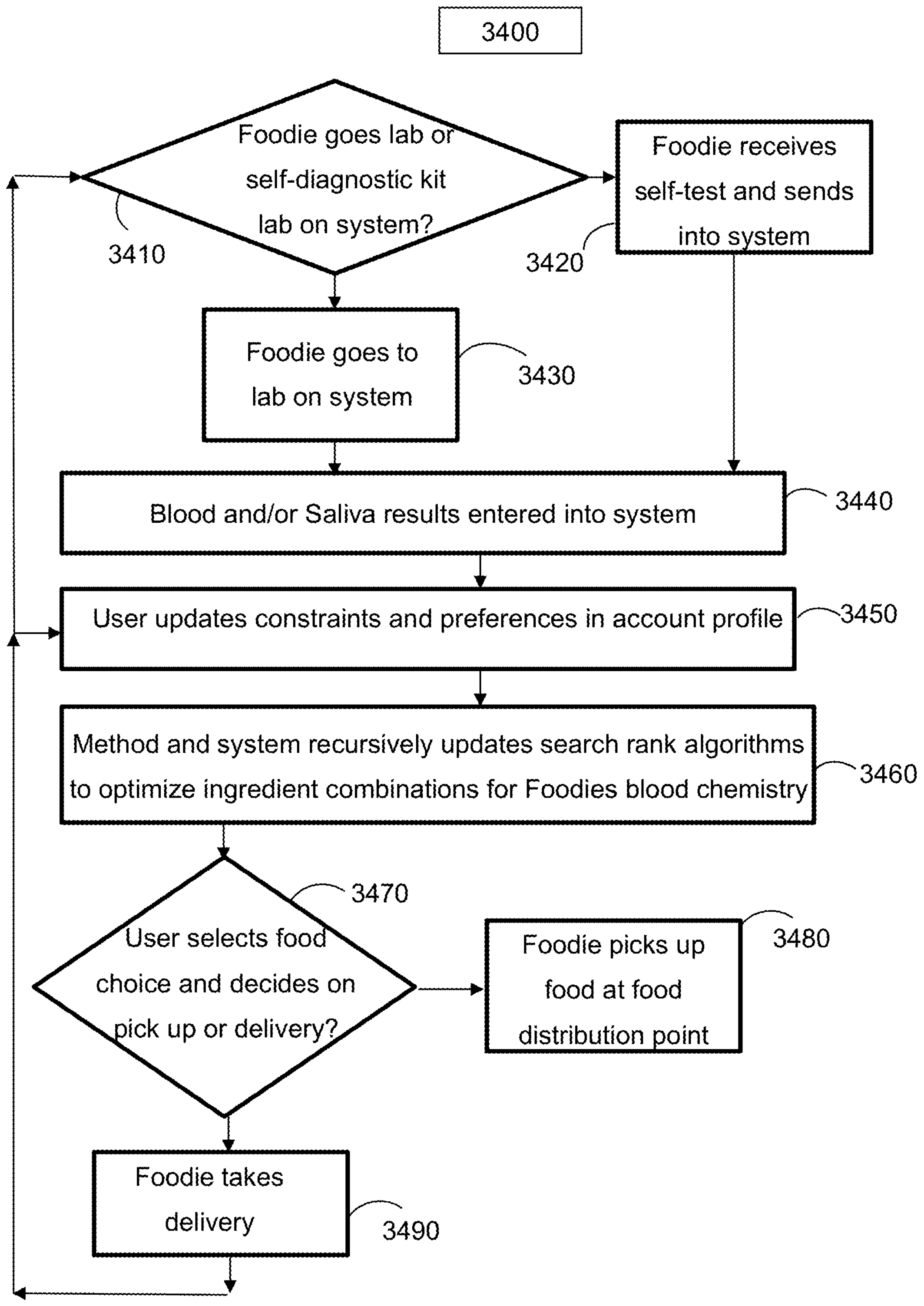
FIG. 34 illustrates an embodiment of one potential flow chart of the method and system processes.

The flow chart illustrated in FIG. 34 for an exemplary scenario of the method and system, a Foodie goes to a lab or orders a self-diagnostic kit 3410. Depending on the Foodies decision 3410 the Foodie either sends in self-test to system 3420 or the lab sends in the results to the system 3430. The blood and/or saliva samples are then entered into the blood and saliva database 3440. The user or Foodie interacts with the system and method to update or select constraints and preferences in their account profile on the system 3450. The method and system recursively updates the algorithm weights and selection combination ingredients based on the optimization program from the system and method based on the foodies blood and saliva chemistry 3460. The Foodie or user then selects either pick up at a food distribution point (grocery store, convenience store, restaurant or other food distribution point) or selects delivery to a point the user desires 3470. The user or foodie may take delivery 3490 or pick up the food at a food distribution point 3480.

Figure 35:
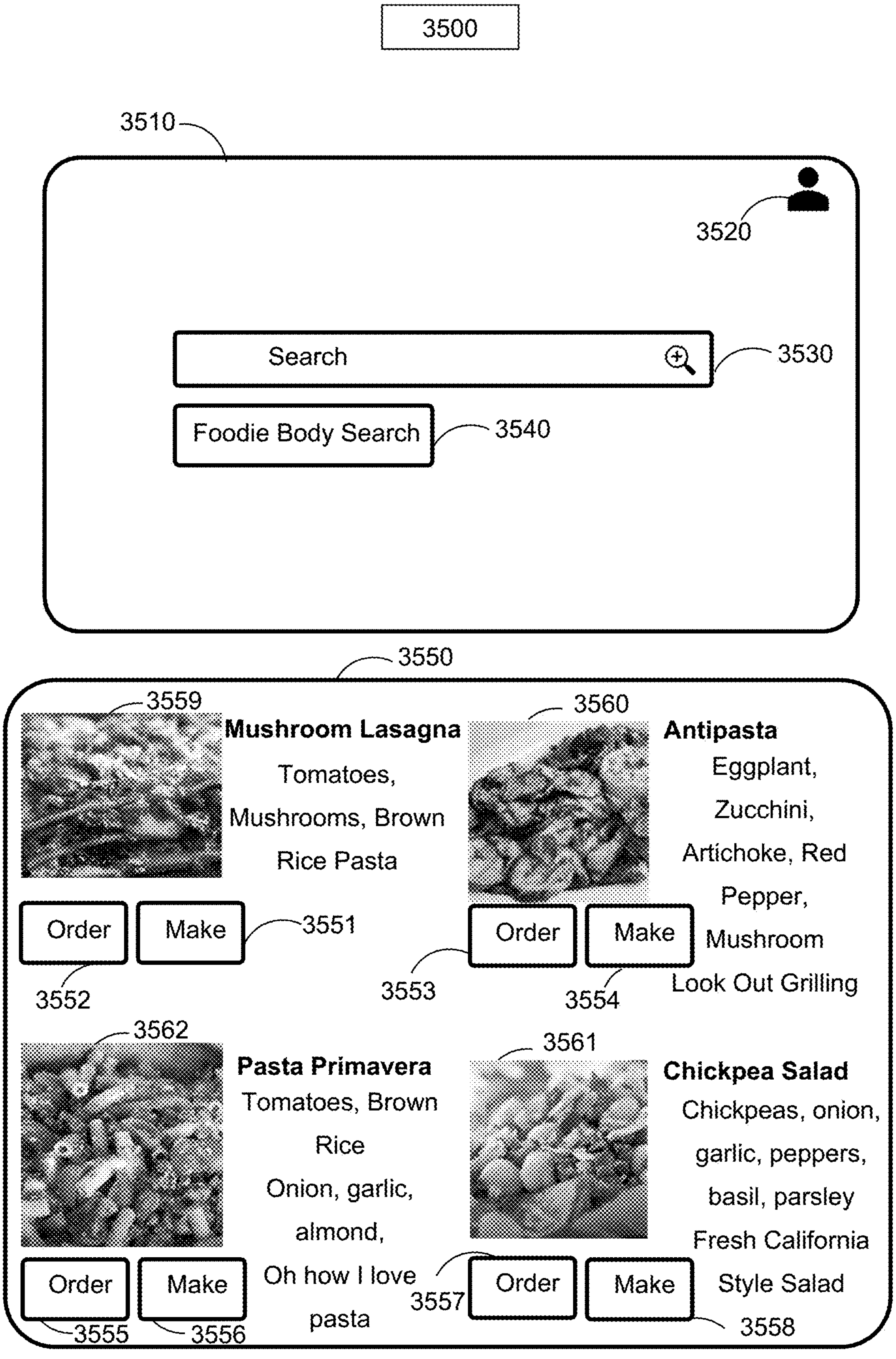
FIG. 35 illustrates an embodiment of an exemplary search engine interface to input search requests to query node ranked optimized food and beverage based on blood, saliva, hair, urine, stool, fingernail, height, weight and skin sampling analysis from machine learning elements of the method.

FIG. 35 illustrates a food and beverage database search interface 3510 in accordance with some embodiments. In some embodiments, the user 3520 profile may have uploaded biomarker data into their user profile or signed an agreement for a lab or physician or other medical provider to release their biomarker data to the biomarker database 220. In some embodiments the user 3520 may input a searchable term or sequence of terms into the search database interface input window 3530. The searchable term or searchable term sequence input window 3530 may suggest similar input terms based on the foodie opportunity set of highest ratio of blood chemistry contribution to blood chemistry variance or location or other constraints. In some embodiments, the user may use voice interface, visual interface, gesture interface or type input and button interface 3540 to instantiate the query of node ranked food and beverage items from the food and beverage database 240 in a category based on food type, ethnicity, style, flavor, location, nutrition, health, variety and delivery of prepared and raw ingredients. In some embodiments by way of example but not limiting by example, the user 3520 may have entered "Italian" as the search term into the search interface input window 3530 and the resulting output interface 3550 may rank a plurality of biomarker ranked food and beverage options based on the highest ratio of blood chemistry contribution to blood chemistry variance or location or other constraints of the exemplary user 3520. In some embodiments for a specific user 3520, mushroom lasagna 3559 may be the highest ratio of blood chemistry contribution to blood chemistry variance in the opportunity set node ranked database for a search input category such as Italian. In some embodiments, the user 3520 may select the Make button 3551 to perform instructions to display a how to ingredient recipe and how to ingredient video of the food or beverage recipe. In some embodiments, the user 3520 may select the Order button 3552 to either pick up the food or beverage combination at a distribution point or have the food or beverage combination delivered to a specified location. In some embodiments, a partial ingredient list, picture, audio, and food score may accompany an additional specific food or beverage combination such as antipasta 3560 with partial ingredients of eggplant, zucchini, artichoke, red pepper, mushroom and a plurality of other ingredients that may be displayed on further drill down search database options. In some embodiments for a specific user 3520, antipasta 3560 may be the second highest ratio of blood chemistry contribution to blood chemistry variance in the opportunity set node ranked database for a search input category such as Italian. In some embodiments, the user 3520 may select the Make button 3554 to perform instructions to display a how to ingredient recipe and how to ingredient video of the food or beverage recipe. In some embodiments, the user 3520 may select the Order button 3553 to either pick up the food or beverage combination at a distribution point or have the food or beverage combination delivered to a specified location. In some embodiments, a partial ingredient list, picture, audio, and food score may accompany a specific food or beverage combination such as antipasta 3560 with partial ingredients of eggplant, zucchini, artichoke, red pepper, mushroom and a plurality of other ingredients that may be displayed on further drill down search database options. In some embodiments, a partial ingredient list, picture, audio, and food score may accompany an additional specific food or beverage combination such as pasta primavera 3562 with partial ingredients of tomatoes, brown rice, onion, garlic, almond and a plurality of other ingredients that may be displayed on further drill down search database options. In some embodiments for a specific user 3520, pasta primavera 3560 may be the third highest ratio of blood chemistry contribution to blood chemistry variance in the opportunity set node ranked database for a search input category such as Italian. In some embodiments, the user 3520 may select the Make button 3556 to perform instructions to display a how to ingredient recipe and how to ingredient video of the food or beverage recipe. In some embodiments, the user 3520 may select the Order button 3555 to either pick up the food or beverage combination at a distribution point or have the food or beverage combination delivered to a specified location. In some embodiments, a partial ingredient list, picture, audio, and food score may accompany a specific food or beverage combination such as pasta primavera 3562 with partial ingredients of tomatoes, brown rice, onion, garlic, almond and a plurality of other ingredients that may be displayed on further drill down search database options. In some embodiments for a specific user 3520, chickpea salad 3561 may be the fourth highest ratio of blood chemistry contribution to blood chemistry variance in the opportunity set node ranked database for a search input category such as Italian. In some embodiments, the user 3520 may select the Make button 3558 to perform instructions to display a how to ingredient recipe and how to ingredient video of the food or beverage recipe. In some embodiments, the user 3520 may select the Order button 3557 to either pick up the food or beverage combination at a distribution point or have the food or beverage combination delivered to a specified location. In some embodiments, a partial ingredient list, picture, audio, and food score may accompany a specific food or beverage combination such as chickpea salad 3561 with partial ingredients of chickpeas, onions, garlic, peppers, basil, parsley and a plurality of other ingredients that may be displayed on further drill down search database options.

FIG. 36 illustrates a food and beverage database search interface 3610 in accordance with some embodiments with additional drill down to a specific search selection. In some embodiments, search engine exemplary logo, foodie body 3620 or another exemplary logo may be displayed. In some embodiments, an exemplary search input window 3630 may allow a user additional search input or input variation from a current search term and food or beverage combination. In some embodiments, the search input visual or audio interface window 3630 may be instantiated from a search term button or an optimize button 3640. In some embodiments, a picture of the drill down food or beverage combination such as mushroom lasagna 3670 may be displayed with a text or audio title 3680. In some embodiments, detailed ingredient lists may accompany the food or beverage combination title 3680. In some embodiments, an ingredient quantity list 3691 and instructions may accompany the selection. In some embodiments a preparation instruction or cooking or chef video may accompany the selection 3690. In some embodiments, a list of participating food or beverage distribution locations 3650 may accompany the food or beverage combination with an option to order from the food distribution location 3650 or receive delivery. In some embodiments, an option to order the food or beverage combination may accompany the selection to order from a restaurant or receive delivery 3660.

Figure 37:
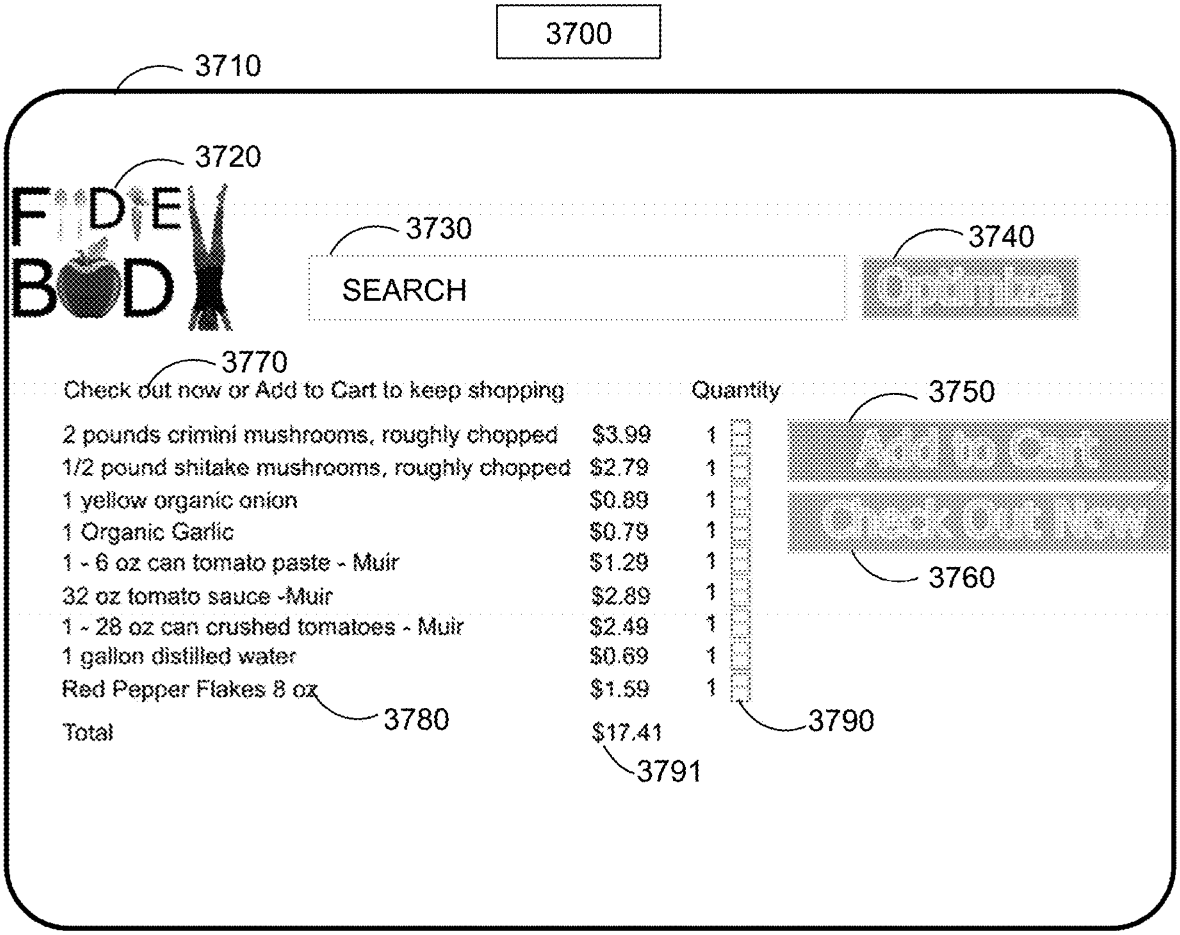
FIG. 37 illustrates an exemplary embodiment of a check out scenario drill down of a certain selected element of the node ranked database of food and beverage which may have been optimized to consider blood, saliva, hair, urine, stool, fingernail, height, weight and skin sampling analysis based on machine learning algorithms.

FIG. 37 illustrates a food and beverage database search interface 3710 in accordance with some embodiments with additional drill down to a specific search selection. In some embodiments, the recipe interface 3610 may be converted into a order quantity interface 3710 for a specific food and beverage combination. In some embodiments, search engine exemplary logo, foodie body 3720 or another exemplary logo may be displayed. In some embodiments, an exemplary search input window 3730 may allow a user additional search input or input variation from a current search term and food or beverage combination. In some embodiments, the search input visual or audio interface window 3730 may be instantiated from a search term button or an optimize button 3740. In some embodiments, the recipe or food combination list 3691 is converted to a check out ready order list 3770, 3780 by associating the recipe quantity with unit sizes at the food or beverage distribution location. In some embodiments, recipe order sizes 3790 may be modified to higher or lower quantities 3790 to serve the customer selection along with information on unit pricing 3791. In some embodiments, an add to cart button 3750 may allow for further shopping or check out now button options 3760 for order conclusion and confirmation.

Figure 38:
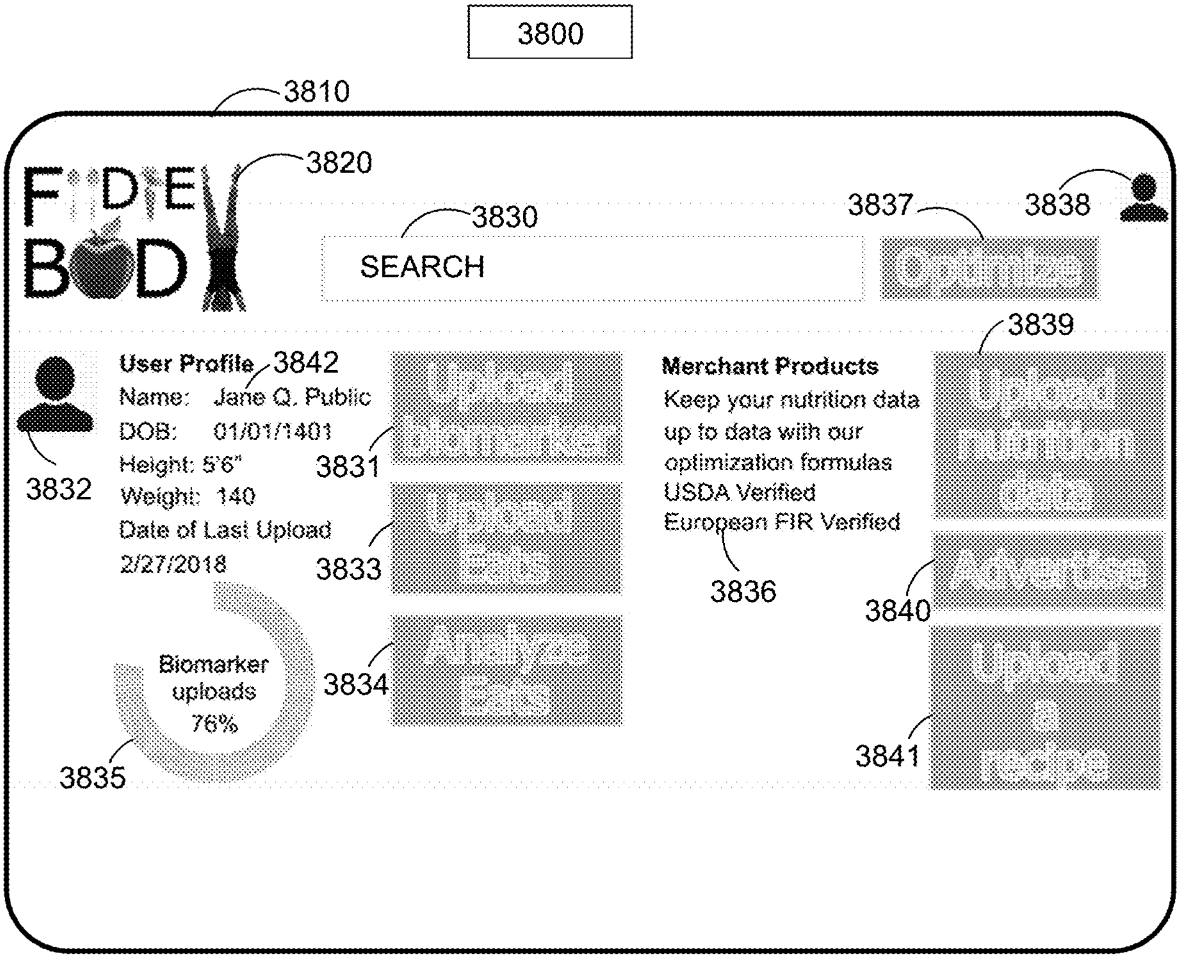
FIG. 38 illustrates an exemplary embodiment of a user biomarker upload interface and merchant nutrition data interface to consider blood, saliva, hair, urine, stool, fingernail, height, weight and skin sampling analysis based on machine learning algorithms.

FIG. 38 illustrates a food and beverage database search interface 3810 in accordance with some embodiments with user biomarker information and options to modify user 3838 biomarker data or upload merchant seller data 3836 to the marketplace. In some embodiments, the user profile 3832 includes name, date of birth, height, weight, most current upload date, and a plurality of other data 3842. In some embodiments, the percentage of available biomarker uploads included for a specific user profile is indicated 3835. In some embodiments, search engine exemplary logo, foodie body 3820 or another exemplary logo may be displayed. In some embodiments, an exemplary search input window 3830 may allow a user additional search input or input variation from a current search term and food or beverage combination. In some embodiments, the search input visual or audio interface window 3830 may be instantiated from a search term button or an optimize button 3837. In some embodiments, a user 3838 or 3832 may update their profile by uploading additional biomarker information with the upload biomarker button 3831. In some embodiments, the user 3832 or 3838 may upload additional eating or consumption data 3833 from a plurality of search, audio, photo, visual or network inputs. In some embodiments, the user 3832 or 3838 may analyze eating and biomarker data by pushing the analyze button 3834. In some embodiments, merchants may upload products 3836 that conform to proprietary standards or the standards of USDA verified or European FIR verified 3836. In some embodiments, merchants my upload products and nutrition data through the upload nutrition data button 3839. In some embodiments, the merchant or user 3832 or 3838 may advertise on the search engine and marketplace method and system of biomarker optimized food and beverage search 3830. In some embodiments, a user 3832 or 3838 may upload a recipe 3841 to the method and system for optimization on the biomarker network and network algorithms. In some embodiments, the search engine and optimization network allows a marketplace for users to contribute recipe content 3841, cooking content 3841, chef preparation content 3841, biomarker content 3831, nutrition content 3839 and user profile 3832 and merchant profile content 3836.

Figure 39:
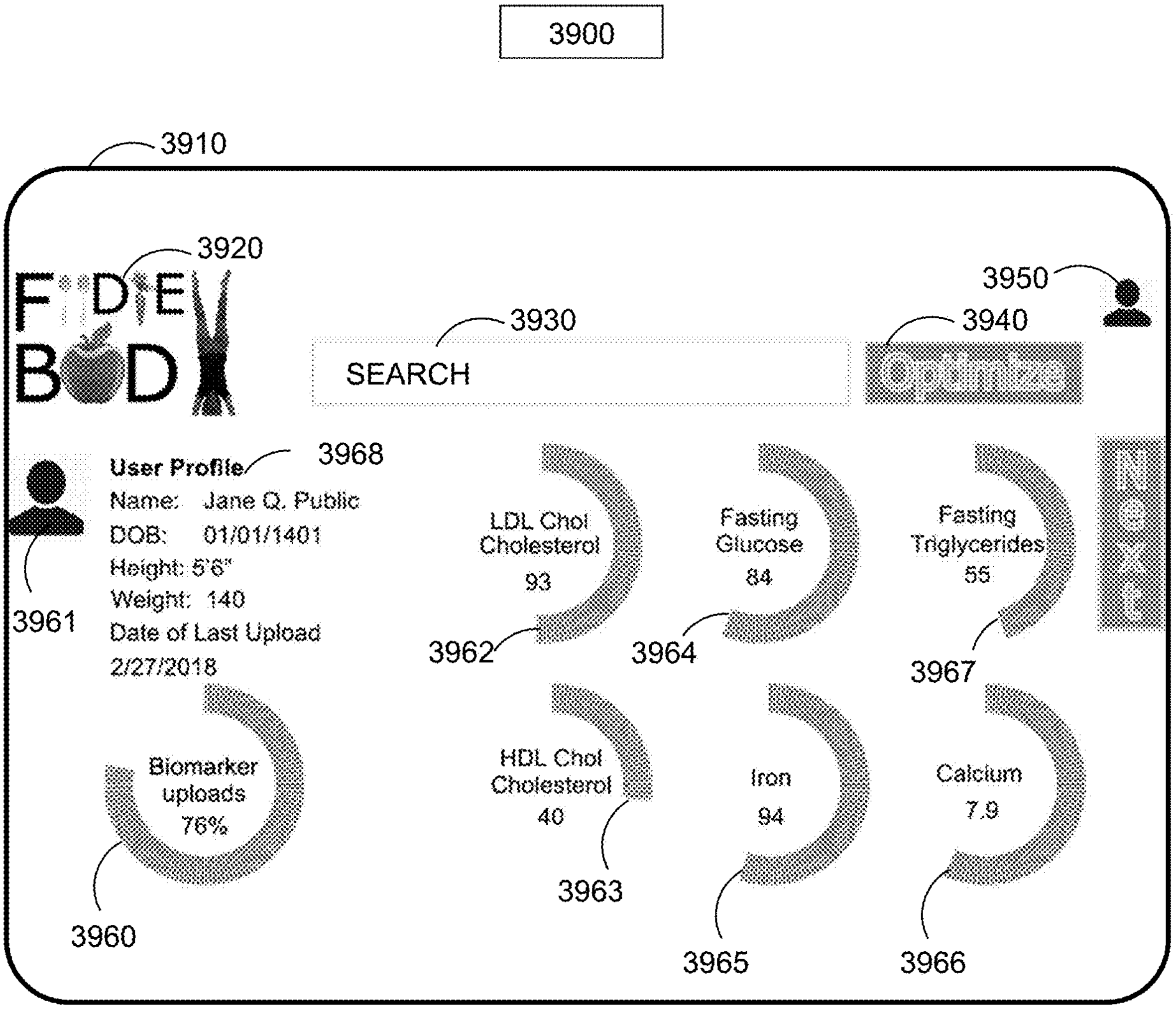
FIG. 39 illustrates an exemplary embodiment of a user interface to consider biomarker data readings based on blood, saliva, hair, urine, stool, fingernail, height, weight and skin sampling analysis based on machine learning algorithms.

FIG. 39 illustrates a food and beverage database search interface 3910 in accordance with some embodiments with user biomarker information and options to modify user biomarker uploads as well as monitor biomarker performance contemporaneously and over time in time series to the marketplace and biomarker search engine. In some embodiments, the percentage of available biomarker uploads included for a specific user profile 3961 is indicated 3960. In some embodiments, search engine exemplary logo, foodie body 3920 or another exemplary logo may be displayed. In some embodiments, an exemplary search input window 3930 may allow a user 3950 additional search input or input variation from a current search term and food or beverage combination. In some embodiments, the search input visual or audio interface window 3930 may be instantiated from a search term button or an optimize button 3940. In some embodiments, the user profile data 3968 may include a superset or subset of name, date of birth, height, weight, date of last upload or other biomarker data 3968. In some embodiments, the percentage of available biomarker upload data fields utilized 3960 by a user 3961 may be displayed. In some embodiments, user 3961 LDL cholesterol levels may be shown for analysis 3962, fasting glucose levels 3964, fasting triglyceride levels 3967, HDL cholesterol levels 3963, iron levels 3965, calcium levels 3966 and a plurality of other biomarkers may be accessed through the continuation to next biomarker data 3910. In some embodiments, over 800 biomarkers are utilized from various measurable biomarker chemistry sources which change due to food and beverage input into the body. In some embodiments, biomarker chemistry may be measured by graph or scan data to represent changes in the body in magnetic resonance imaging tests, echocardiogram tests, nuclear perfusion studies, positron emission tomography tests or thousands of other biomarker scan and chemistry tests where data may be measured with numeric representations.

Figure 40:
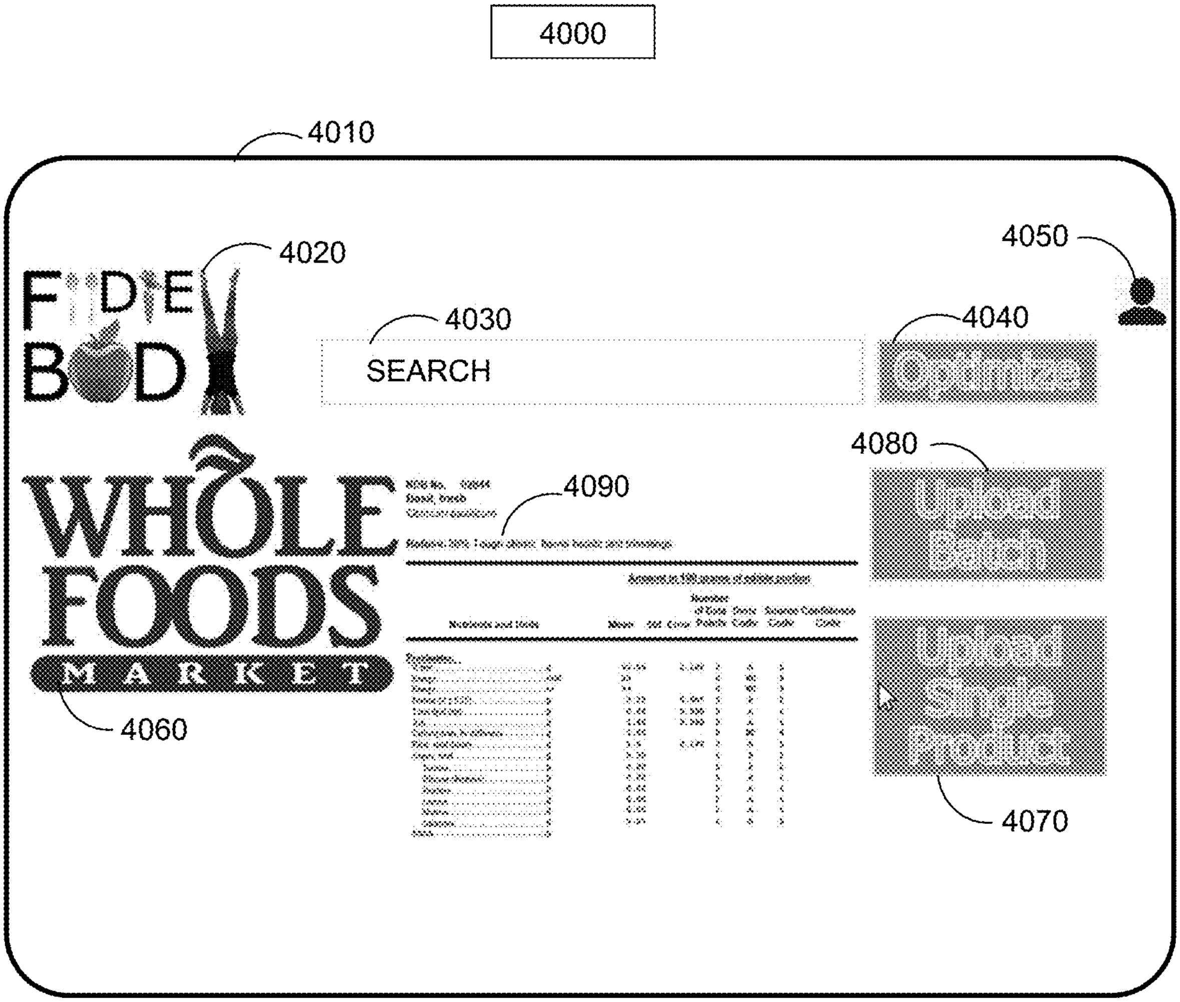
FIG. 40 illustrates an exemplary embodiment of a food or beverage merchant interface to upload nutrition data to the database and machine learning algorithm method.

FIG. 40 illustrates a food and beverage database search interface 4010 in accordance with some embodiments with merchant nutrition 4090 and product upload 4070 or batch product upload 4080 for participation in the biomarker search engine for food and beverages. In some embodiments, search engine exemplary logo, foodie body 4020 or another exemplary logo may be displayed. In some embodiments, an exemplary search input window 4030 may allow a user 4050 additional search input 4030 or input variation from a current search term and food or beverage combination. In some embodiments, the search input visual or audio interface window 3930 may be instantiated from a search term button or an optimize button 4040. In some embodiments, an exemplary food or beverage distribution vendor or supplier 4060 may be displayed for their account 4050 to upload nutrition information for entire batches 4080 or single products 4070. In some embodiments, vendors 4060 may license the method and system to participate in the search for food and beverages based on a plurality of biomarker data of individual users.

Figure 41:
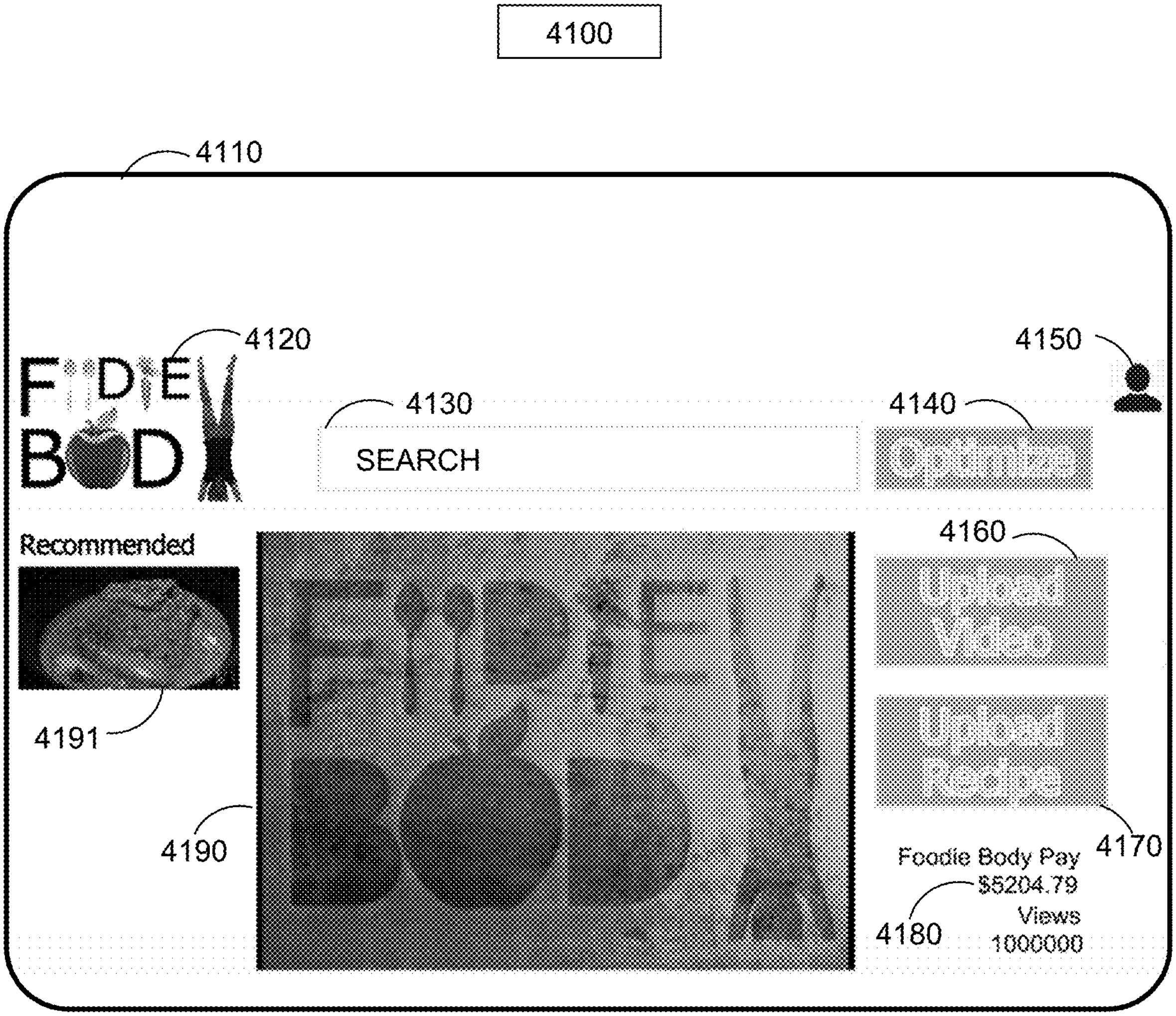
FIG. 41 illustrates an exemplary embodiment of a recipe and cooking video upload and display interface for the video search node ranked optimization based on blood, saliva, hair, urine, stool, fingernail, height, weight and skin sampling analysis based on machine learning algorithms.

FIG. 41 illustrates a food and beverage database search interface 4110 in accordance with some embodiments with recipe or cooking content videos 4190 for the biomarker based search engine for food and beverages. In some embodiments, search engine exemplary logo, foodie body 4120 or another exemplary logo may be displayed. In some embodiments, an exemplary search input window 4130 may allow a user 4150 additional search input 4130 or input variation from a current search term and food or beverage combination. In some embodiments, the method and system may recommend additional food and recipe videos 4191 based on popularity, linked recipe types, efficient ratios of blood chemistry expected values to blood variance values in the opportunity set. In some embodiments, the user 4150 may upload a video 4160 with cooking content and recipe content that has been optimized for the user's biomarkers. In some embodiments, the user may upload recipes and nutrition data to the network for ranking in the search node ranking database or related video ranked node database with nutrition data of the underlying recipe from the food database 240. In some embodiments, the user 4150 may receive rewards such as foodie body pay 4180 for videos that are popular or receive high views 4180 because they are well done with efficient blood chemistry values to blood chemistry variance as a ratio.

Figure 42:
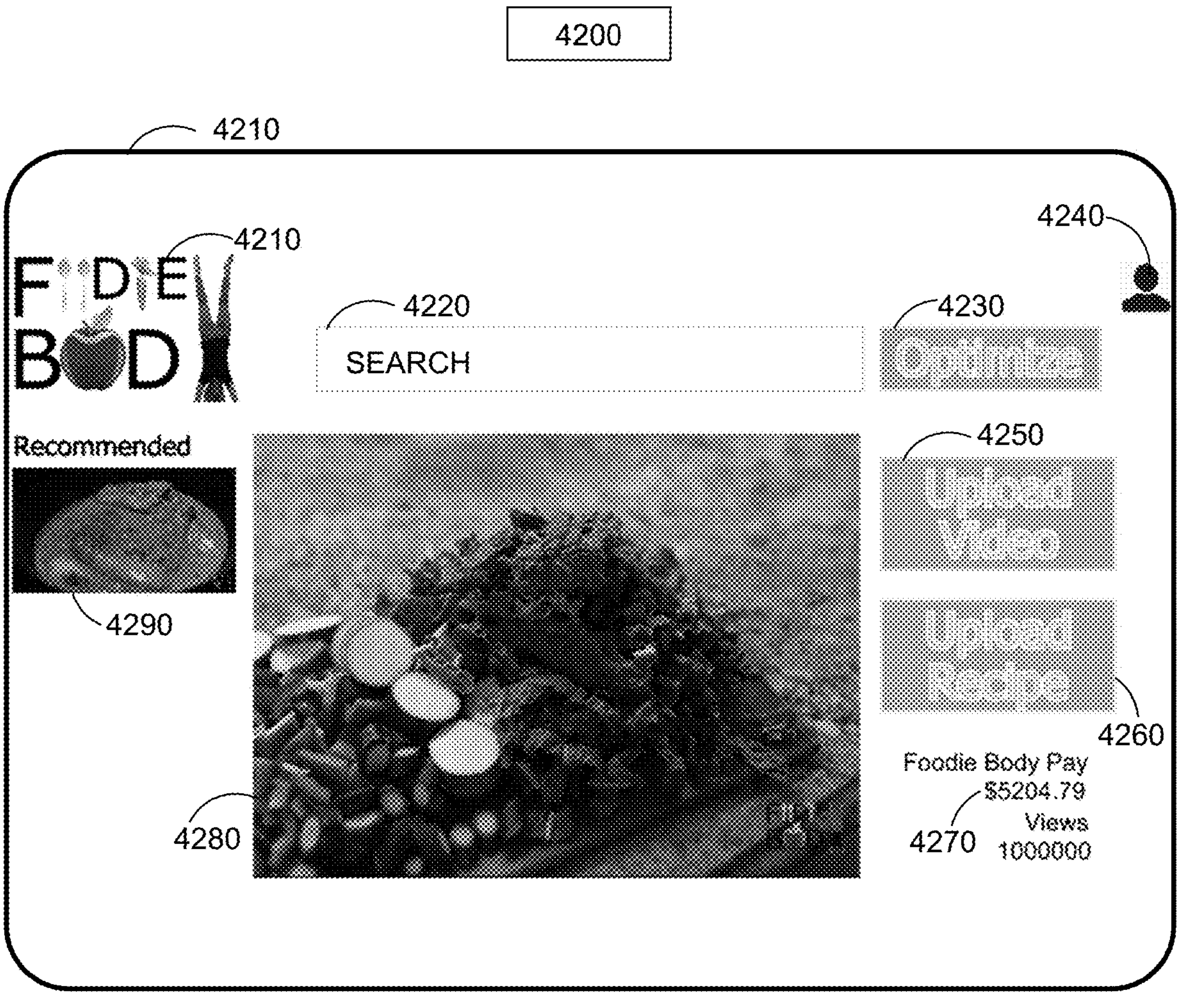
FIG. 42 illustrates an additional exemplary embodiment of a recipe and cooking video upload and display interface for the video search node ranked optimization based on blood, saliva, hair, urine, stool, fingernail, height, weight and skin sampling analysis based on machine learning algorithms.

FIG. 42 illustrates a food and beverage database search interface 4210 in accordance with some embodiments with additional recipe or cooking content videos 4280 for the biomarker based search engine for food and beverages. In some embodiments, search engine exemplary logo, foodie body 4210 or another exemplary logo may be displayed. In some embodiments, an exemplary search input window 4220 may allow a user 4240 additional search input 4220 or input variation from a current search term and food or beverage combination video 4280. In some embodiments, the method and system may recommend additional food and recipe videos 4290 based on popularity, linked recipe types, efficient ratios of blood chemistry expected values to blood variance values in the opportunity set. In some embodiments, the user 4240 may upload a video 4250 with cooking content and recipe content that has been optimized for the user's biomarkers. In some embodiments, the user 4240 may upload recipes and nutrition data 4260 to the network for ranking in the search node ranking database or related video ranked node database with nutrition data of the underlying recipe from the food database 240. In some embodiments, the user 4240 may receive rewards such as foodie body pay 4270 for videos that are popular or receive high views 4270 because they are well done with efficient blood chemistry values to blood chemistry variance as a ratio.

Figure 43:
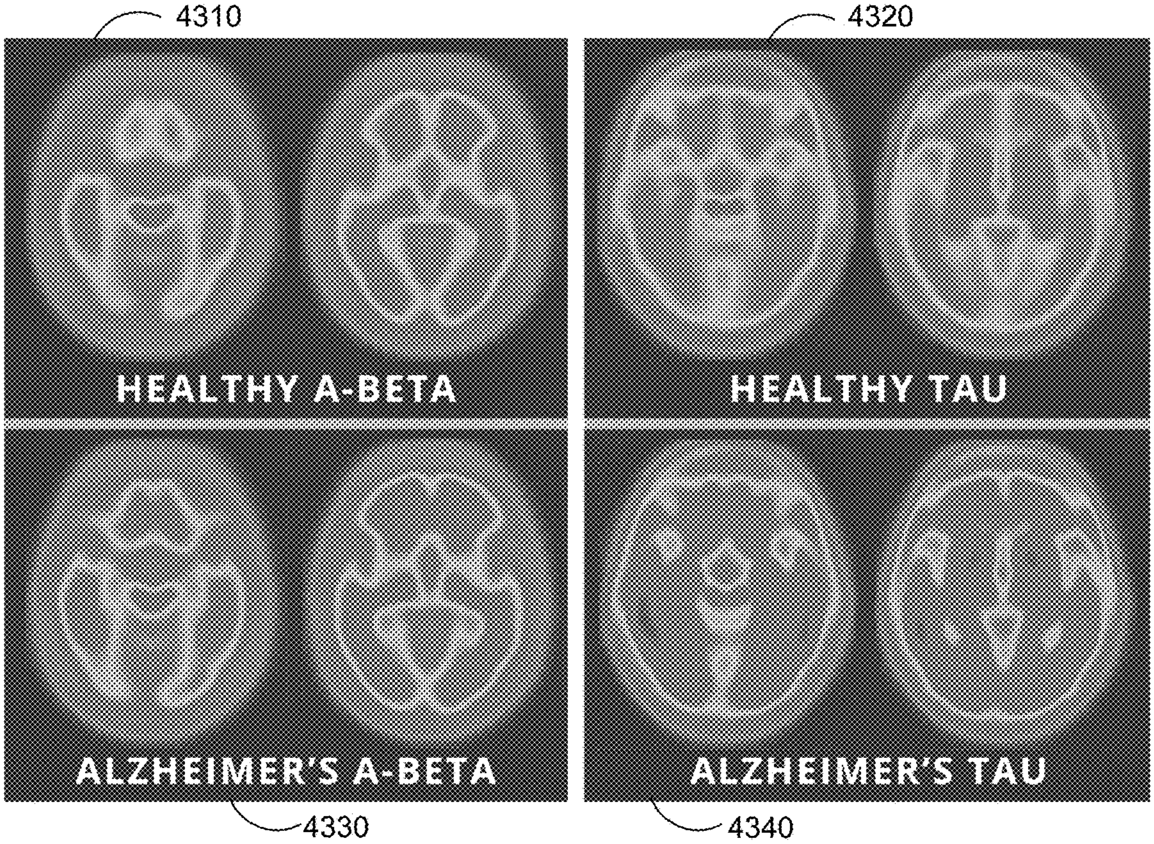
FIG. 43 illustrates an exemplary embodiment of a biomarker Alzheimer's positron emission tomography attribute machine learning model equation sequence to node rank foods and beverages with specified optimization constraints and predictive sequences.

FIG. 43 illustrates a positron emission tomography output 4300 with a plurality of various conditions such as a health brain with low levels of beta amyloid 4310, high levels of beta-amyloid 4330 and resulting Alzheimer's, healthy levels of hyperphosphorylated protein tau 4320 and no resulting Alzheimer's and high levels of hyperphosphorylated protein tau 4340 with resulting Alzheimer's. In some embodiments, data is transformed with progressive machine learning equation fitting models including but not limited to linear regression, logistic regression, linear discriminant analysis, classification or regression trees, naïve bayes, k nearest neighbors, leaning vector quantization, support vector machines, bagging and random forest, boosting and adaboost models to update best fit historical equations for a user's time series data of biomarker panels considering food and beverage consumption. In some embodiments, exemplary models may include but are not limited to the following machine learning model outputs such as Alzheimer's indicator equation 4350 beta amyloid plaque level equaling 141.76 plus 63.46 multiplied by X sub i index which represents cholesterol intake less the quantity of 12.96 X squared sub i index which represents cholesterol intake plus 0.93 multiplied by X cubed sub i, where X is again the level of cholesterol intake over time period i. In some embodiments, exemplary models may include but are not limited to the following machine learning model outputs such as Alzheimer's indicator equation 4360 hyperphosphorylated protein tau level equaling 11.76 plus 66.6 multiplied by X sub i index which represents cholesterol intake less the quantity of 1.21 X squared sub i index which represents cholesterol intake plus 0.32 multiplied by X cubed sub i, where X is again the level of cholesterol intake over time period i. In some embodiments, exemplary models may include but are not limited to the following machine learning model outputs such as Alzheimer's indicator equation 4370 neurofibrillary tangles level equaling 8.88 plus 15.47 multiplied by X sub i index which represents cholesterol intake less the quantity of 2.06 X squared sub i index which represents cholesterol intake plus 0.10 multiplied by X cubed sub i, where X is again the level of cholesterol intake over time period i. In some embodiments, exemplary models may include but are not limited to the following machine learning model outputs such as Alzheimer's indicator equation 4380 ApoE3 beta amyloid plaques level equaling 1.2 plus dummy variable δ sub 0 which indicates the presence of the ApoE3 gene plus 63.46 multiplied by X sub i index which represents cholesterol intake less the quantity of 12.96 X squared sub i index which represents cholesterol intake plus 0.93 multiplied by X cubed sub i, where X is again the level of cholesterol intake over time period i. In some embodiments, machine learning models continue to iterate model fitting until error minimization has been achieved and therefore, model fitting in the method is not limited to equations 4350, 4360, 4370, 4380, but rather the method to fit models to minimize the error terms in obtaining the food and beverage sequences which maximize the ratio of the biomarker chemistry value improvement over the variance of the biomarker chemistry resulting in the most efficient path to health improvement as measured by biomarker analysis as well as the node ranking of a plurality of search category food and beverage items as defined by their ranking of maximizing the ratio of biomarker chemistry improvement over the variance of the biomarker chemistry improvement. In some embodiments, the machine learning model fitting technique and resulting node ranking of food and beverage sequences which maximize the ratio of the biomarker chemistry value improvement over the variance of the biomarker chemistry improvement resulting in the most efficient path to health improvement as measured by biomarker analysis may be applied to any biomarker indicator of health condition such as Alzheimer's, heart disease, echocardiogram, nuclear perfusion studies, magnetic resonance imaging, hemoglobin A1C diabetes test, glycohemoglobin test, leukocyte antigen HLA-DQ2 or HLA-DQ8 tests, TSH thyroid stimulating hormone or total T4 free thyroxine, free T4, total T3, free T3, reverse T3, anti TPO ab, anti thyroglobulin Ab, broad thyroid panels, iron, vitamin D, vitamin b12, magnesium, calcium, complete metabolic panels, complete blood count, homocysteine, hsCRO inflammatory marker, homocysteine level, amino acid levels, white blood cell count, red blood cell count, hemoglobin, hematocrit, mean corpuscular volume, platelet count, LDL low density lipoprotein cholesterol, HDL high density lipoprotein cholesterol, sodium, potassium, chloride, carbon dioxide, blood urea nitrogen, creatine, glucose, total protein, albumin, bilirubin, alkaline phosphatase, aspartate aminotransferase, alanine am inotransferase, methylmalonic acid, glycated hemoglobin, prothrombin time, international normalized ratio (prothrombin time), brain natriuretic peptide, ferritin, bone marrow biopsy, barium enema, bone scan, breast MRI, colonoscopy, computed tomography scan, digital rectal exam, hypercholesterolemia, atherosclerotic plaque level, plasma level, endoscopy, fecal occult blood tests, mammography, MUGA scan, pap test, sigmoidoscopy, circulating tumor cell, flow cytometry, cytogenetic analysis, immunophenotyping, fluorescence in situ hybridization, karyotype test, polymerase chain reaction, white cell differential, general biopsies with change analysis indicator variables or any biomarker test.

FIG. 44 illustrates a low density lipoprotein LDL cholesterol output 4400 over time series between two points in time with the user eating foods and beverages recommended by the search engine that node ranks the ratio of biomarker chemistry change over biomarker chemistry variance during the time period from a starting point at time of t=0 before changing diet to items recommended by search engine. In some embodiments, the biomarker of low density lipoprotein LDL cholesterol may be measured over time 4410 as the user eats the search items node ranked by the method. In some embodiments, machine learning models may fit the user relationship of cholesterol in food and beverages to low density lipoprotein with the equation 4411 where low density protein equals negative 1.2 multiplied by the natural log of X sub i, where X is the level of cholesterol in food and beverages ingested between time period t=0 and t=i plus 140+a dummy variable δ sub 0 that may indicate the presence of phytosterols, soluble fibers, phospholipids, stearic acid or other cholesterol absorption inhibitors. In some embodiments, each biomarker time series represented in the machine learning model 4410 may have different best fit models for each user as each model is generated from time series of users or users with similar characteristics as a proxy until appropriate time series may be logged in the biomarker database server 220. In some embodiments, calcium biomarkers may be measured from a base state of time equaling zero 4420 before the user commences use of the method to maximize the biomarker ratio or ratio sequence of biomarker value contribution over biomarker variance contribution in the node ranked database which may be utilized in search engine results. In some embodiments, the biomarker calcium contribution may be measured by calcium biomarker sub i equals 1.3 multiplied by the natural log of X sub i, where X is the food or beverage contribution to the biomarker in the form of calcium plus 8.8. In some embodiments, the users may be represented by time series in the graph 4420 each having their own minimization of error machine learning model in accordance with then the maximization of the ratio of biomarker value contribution over biomarker variance contribution in the node ranked database.

Figure 45:
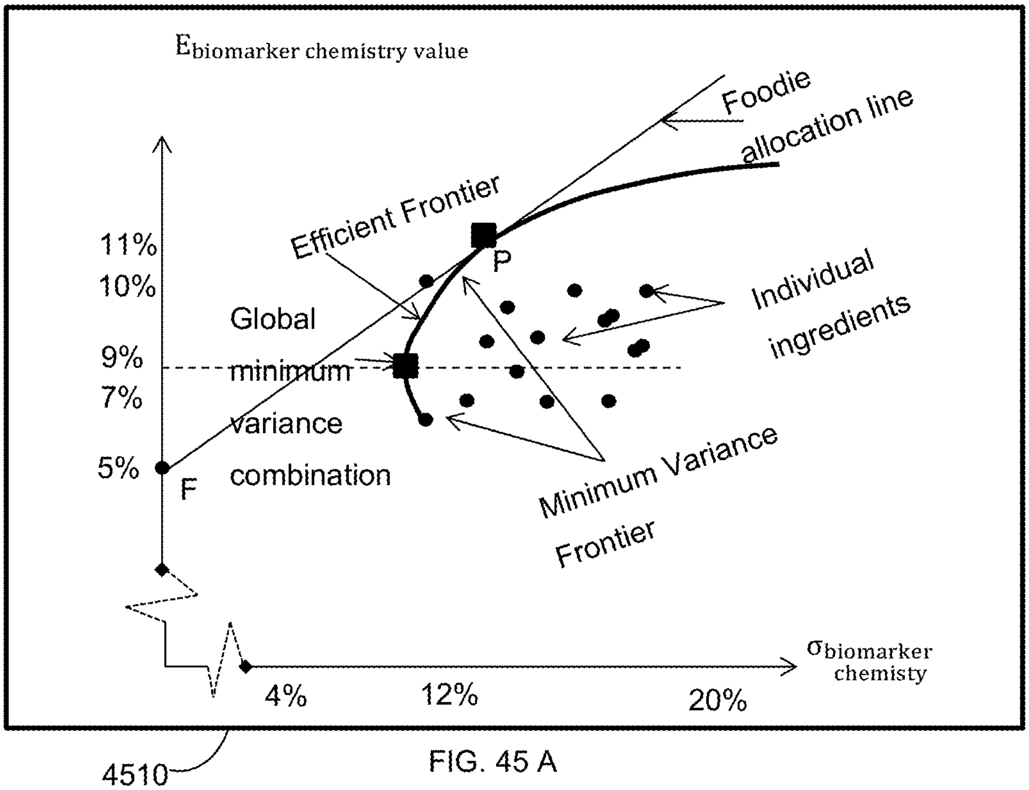
FIGS. 45A and 45B illustrate an exemplary embodiment of a biomarker or plurality of biomarkers general equation graphic representation of a plurality of machine learning models with minimized errors or other best fit parameters contributing to a desired biomarker chemistry value or sequence.
Figure 45:
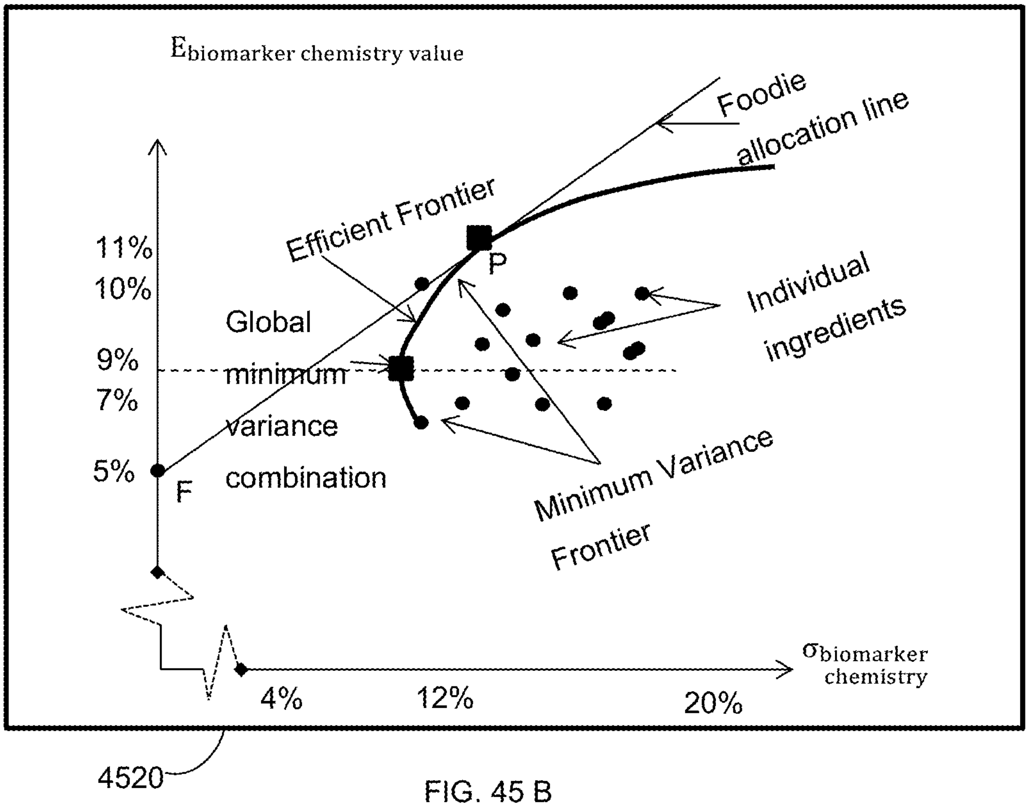

FIGS. 45A and 45B illustrate an exemplary embodiment of the foodie allocation line relative to the opportunity set of food and beverage combinations 4500 as ranked by the node food and beverage node database server 240. In some embodiments, the expected value of the biomarker chemistry value is represented by the vertical Y axis as the contribution of food or beverage to the representative biomarker or vector of biomarkers in N dimensional space 4510. In some embodiments, the variance of the biomarker chemistry value is represented by the X horizontal axis in N dimensional space 4510. In some embodiments, portfolios of various food and beverage combinations, recipes, meals, restaurant or food ordered deliveries are shown at various levels which may be node ranked in a database based on the ratio of expected contribution of biomarker chemistry contribution value to a target over the variance of the biomarker chemistry value contribution. In some embodiments, an optimal or most efficient food and beverage combination represented by point P in diagram 4510 may be achieved at the highest point where the foodie allocation line matches the minimum variance frontier for the plurality of various food and beverage combinations for a specific user. In some embodiments, the general framework 4510 may select a vector or matrix of food combinations and a vector and matrix of biomarkers which may be fundamentally different than another vector and matrix of biomarkers or food and beverage combinations represented in model 4520. In some embodiments, node ranked food and beverage combinations based on the efficiency ratio of expected biomarker value contribution over variance of biomarker value considering the foodie allocation line and efficient minimum variance frontier may be updated based on machine learning model updates for minimization of errors in food and beverage combination contribution to biomarker values.

Figure 46:
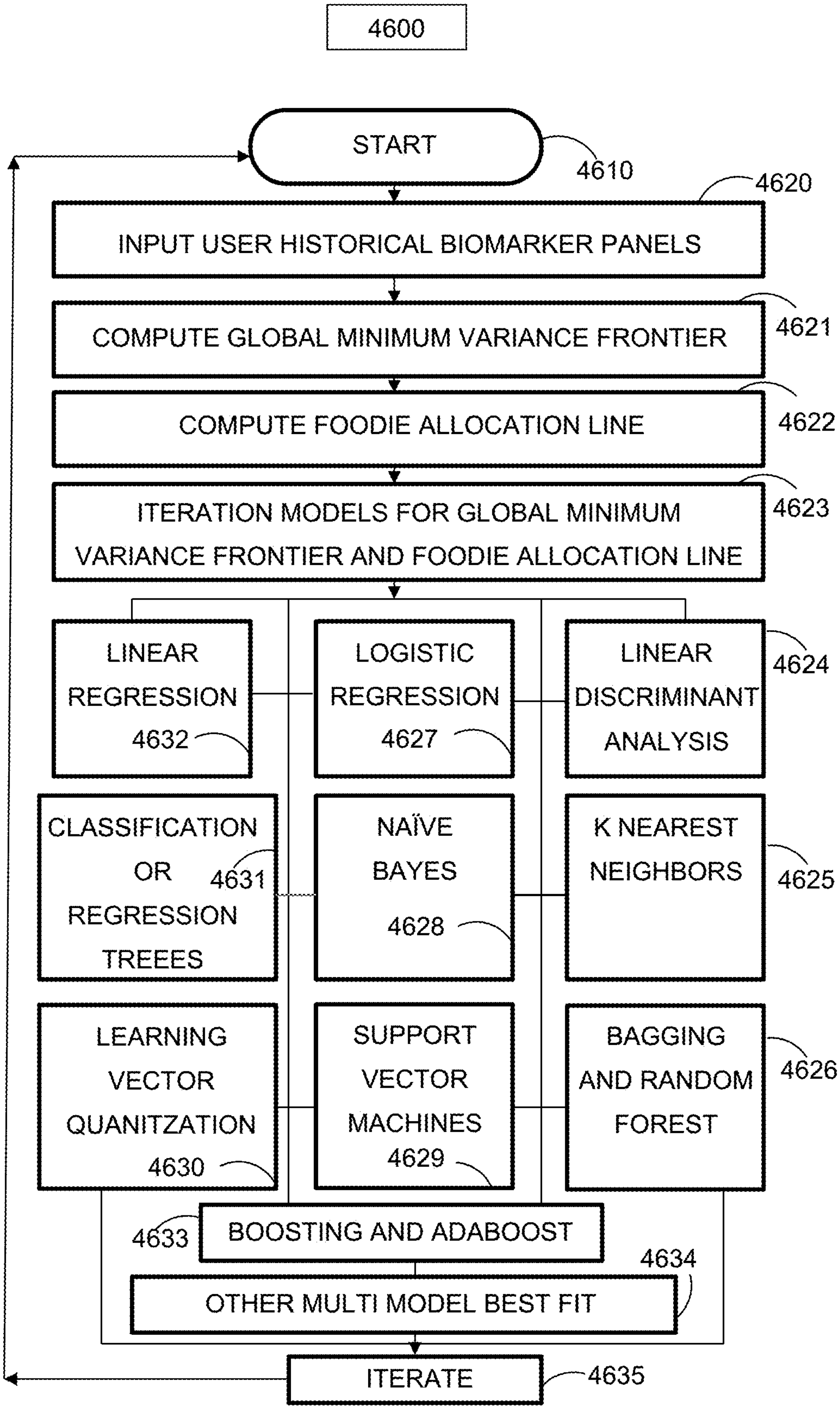
FIG. 46 illustrates an exemplary flow chart or sequence chart of computing minimum variance frontiers, foodie allocation lines, machine learning models which report best fit analytics to optimization sequences to node rank food and beverages.

FIG. 46 illustrates an exemplary embodiment of a flow chart construction of the iterative loop for constructing sets of biomarker panels 4620, food and beverage contribution to biomarker global minimum variance frontiers and portfolios 4621, foodie allocation lines 4622, machine learning models 4632, 4627, 4624, 4631, 4628, 4625, 4630, 4629, 4626, 4633, 4634 to test historical datasets of user food and beverage interaction with biomarker values which form the basis of the method to node rank food and beverage combinations for users 4600. In some embodiments, the user 210 obtains self test or lab test biomarkers and updates the system 4620 to form the basis of a time series or comparison data for comparable users. In some embodiments, the computation of the global minimum variance frontier of food and beverage contributions to biomarker values and variance of biomarker values to form ratios of biomarker value contribution over variance of biomarker contributions in the node ranked database for food and beverage combinations 4621. In some embodiments, the foodie allocation line is constructed based on a plurality of utility attributes of the user such as but not limited to flavor, ethnicity, location, style, hunger, genetics or other utility characteristics 4622. In some embodiments, the search input may then instruct the system to iterate the foodie allocation line over a minimum variance frontier of food and beverage combination categories 4623. In some embodiments, the machine learning models determine the best fit by minimizing errors of a plurality of functions 4624 for food and beverage contribution to expected biomarker values of users and the resulting maximization of the ratio of expected biomarker contribution value over expected biomarker contribution variance and then node ranking lower from the highest ratio value in accordance with the foodie allocation line 4622 and minimum variance frontier 4621. In some embodiments, machine learning best fit models determining food and beverage contribution to biomarker values or ratio of biomarker values over variance of biomarker value may be comprised of but not limited to linear regression 4632, logistic regression 4627, linear discriminant analysis 4624, classification or regression trees 4631, naïve bayes 4628, k nearest neighbors 4625, learning vector quantization 4630, support vector machines 4629, bagging and random forest 4626, boosting and adaboost 4633, ARIMA processes, Box-Jenkins, posterior density functions, natural conjugate prior, recursion, Bayesian pretest, ridge regression, independent stochastic regressors, general stochastic regression models, general non-linear hypothesis, LaGrange multiplier test, Likelihood ratio test, autoregressive processes, moving average processes, ARMA processes, GLS, EGLS, NLS, ML estimation, AR(1), AR(2), Wald test, Durbin-Watson test, King's locally optimal bounds, Geary's sign change test, MA(1), Monte Carlo, finite distributed lags, almon distributed lag, polynomial spline distributed lag, Shiller's distributed lag, Harmonic Lag, gamma distributed lag, exponential lag, heteroscedastic specifications, Breusch-Pagan Test, Barlett Test, Godfeld Quandt test, Szroeters Class of tests, Whites Test, nonparametric tests, vector ARMA processes, ARMAX models, vector autoregressive processes, path analysis, binary choice models, multinomial logit, multinomial probit, truncated samples, two stage models, Amemiya's principle model, simultaneous equation model, piecewise regression, seasonality models, Akaike information Criterion, Jeffrey-Bayes Posterior odds ratio, conditional mean, Stein-Rule formulation model, Cox test model, J test model, quasi-Newton method model, Gauss method model, gradient method model, Marquardt's method model, Gauss-Seidel model, Grid Search, reparameterization model, penalty function model, augmented Lagrangian method model, Kalman Filter model or other models for use in determining food and beverage contribution to biomarkers in construction of a ratio to place the expected contribution value of the biomarker over the variance of the biomarker contribution value for a node ranked database for food and beverage combinations. In some embodiments, each of the aforementioned processes and transformations are then iterated continuously 4635 based on updates to machine learning fit models, food and beverage inputs, biomarker test results, computation of minimum variance frontiers, computation of foodie allocation lines or other model updates.

Figure 47:
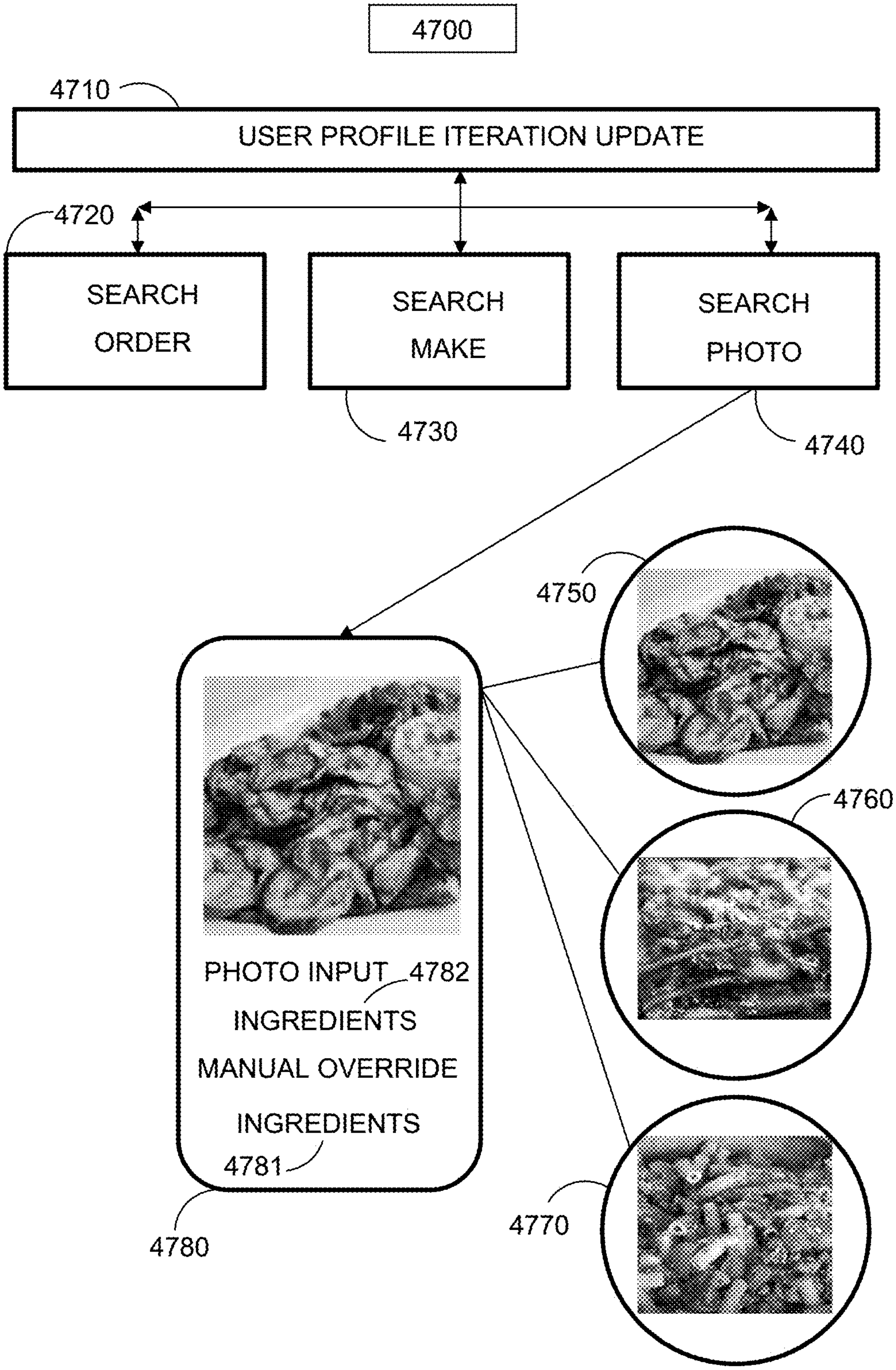
FIG. 47 illustrates an exemplary search input interface that considers voice, text, visual or other inputs to search for a food or beverage type order, search recipe to make for oneself or search input based on a picture, scan or manual override input.

FIG. 47 illustrates an exemplary embodiment of a user profile iteration update from a search order 4720, search for making a recipe 4730, or search from photo 4740, audio or visual recognition of foods or beverages. In some embodiments, a CPU device 4780 with visual, photo, recognition, voice or other interface may update from a plurality of inputs including but not limited to visual scan recognition of ingredients or food or beverage 4782. In some embodiments, a manual override 4781 may allow the user to update the search or order of food and beverage to update the user profile intake of food and beverage. In some embodiments a sequence of foods 4750, 4760, 4770 may be input into the system by a user using the CPU device 4780. In some embodiments, food and beverage search, ordering, making of recipes, audio interface, scan interface or photo interface 4782 may update the user profile 4710 with food and beverage combinations 4750 to the system may estimate user performance between biomarker test periods.

Figure 48:
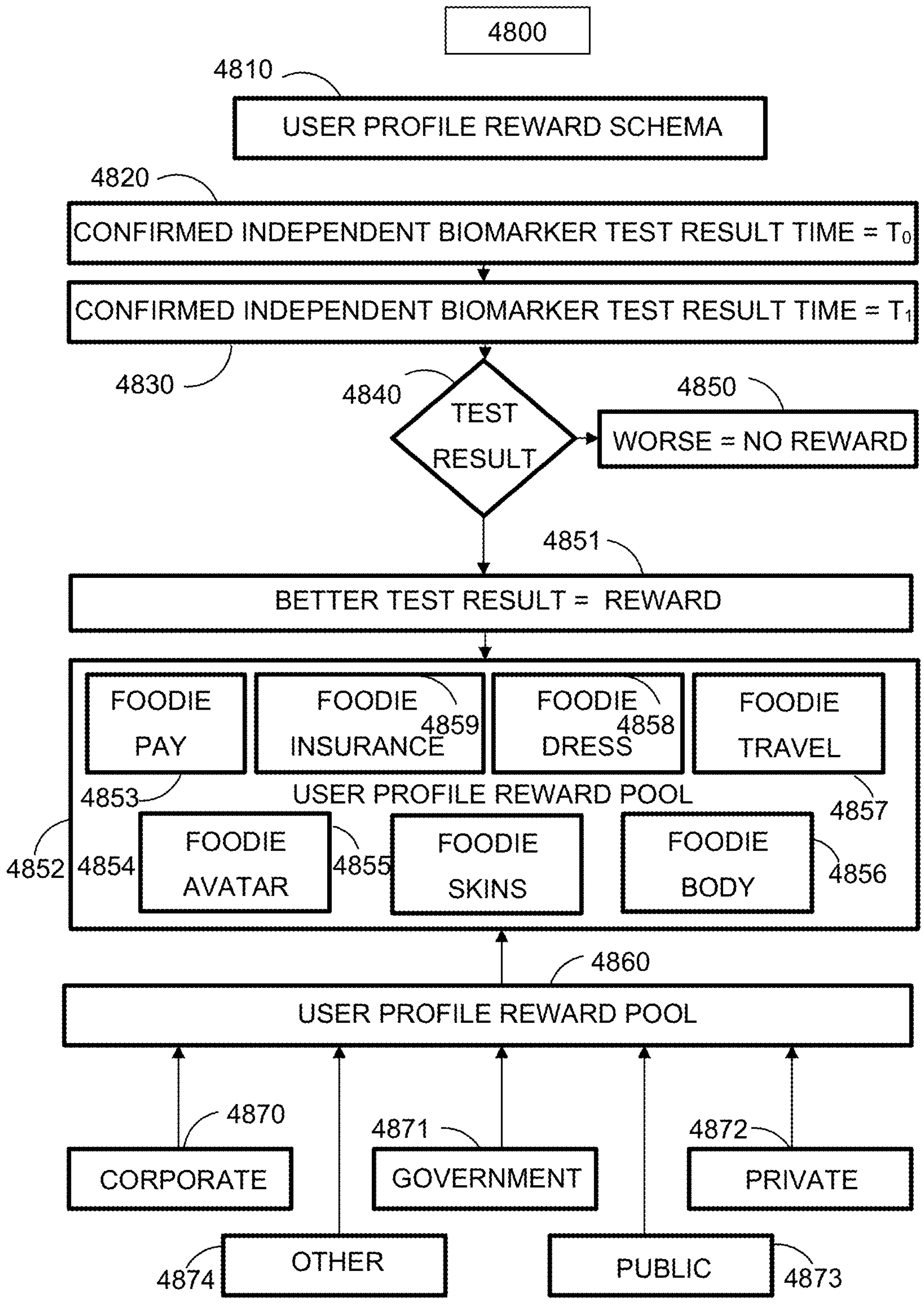
FIG. 48 illustrates and exemplary user award schema and contribution schema utilizing independent test results for blood, saliva, hair, urine, stool, fingernail, height, weight and skin sampling analysis based on machine learning algorithms.

FIG. 48 illustrates an exemplary user profile reward schema for confirmed biomarker improvements for target biomarker input in the system as a result of food and beverage combination improvements to the user 4800. In some embodiments, it is well known that diets do not work or they are unsustainable, it is also well known that companies or governments usually do not pay or incentivize people with any significant reward to eat well with the opportunity independently confirmed and rewarded by an independent biomarker measurement lab or facility. In some embodiments, a typical user profile reward schema 4810 may include a baseline biomarker test on time t=0 confirmed by an independent test or lab 4820. In some embodiments, a user may perform or be evaluated by a second biomarker test or lab at time t=1 4830. In some embodiments, a reward may be given to the user based on achieving a specified biomarker test level over a period or time which may include one time period or a sequence of time periods or other combinations of time. In some embodiments, the biomarker test result 4840 is performed or evaluated by an independent biomarker lab. In some embodiments, if the biomarker target value was not achieved, no reward is given to the user or a penalty may be given 4850. In some embodiments, if the target biomarker test result is achieved 4851, a reward may be given 4852. In some embodiments, rewards 4852 may include but are not limited to foodie pay 4853, foodie insurance 4859, foodie dress 4858, foodie travel 4857, foodie avatars 4855, foodie skins 4854, foodie body 4856 or other rewards 4852. In some embodiments, the user profile award pool 4860 may be comprised of but not limited to corporates 4870, government 4871, private sector 4872, other entities 4874, public entities 4873. In some embodiments, the reward pool 4860 may be calculated in conjunction with performance of reducing an employers insurance payout, government insurance payout or other payouts due to high health care costs which have been avoided or reduced, environmental benefits, pollution reduction, based on improved biomarker performance or any other metric chosen by an entity contributing to the reward pool. In some embodiments the user profile reward schema 4810 may be updated instantly or over time.

Figure 49:
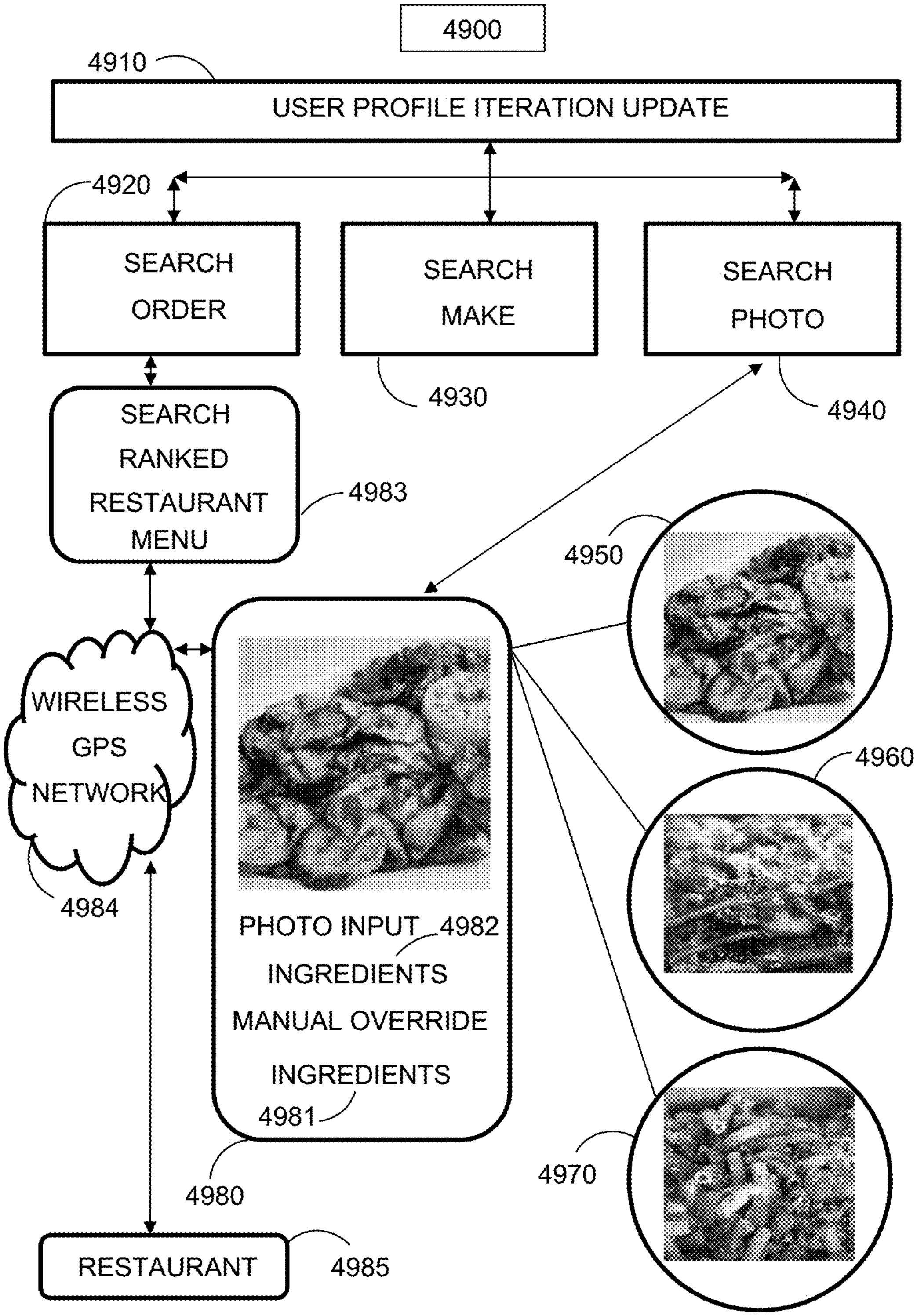
FIG. 49 illustrates an exemplary search input interface that considers voice, text, visual or other inputs to search for a food or beverage type order, search recipe or geolocation proximity to make for oneself or search input based on a picture, scan, geolocation or manual override input.

FIG. 49 illustrates an exemplary user iteration update 4910 based on search order input 4920, search that was made form a searched recipe 4930, search from an audio or visual or photo input 4940 from a CPU device 4980. In some embodiments, the user CPU device 4980 may update with a food distribution point menu 4983 with node ranked search results based on the user's location from a wireless GPS network 4985. In some embodiments, the food distribution point may be a restaurant 4985 or any food distribution establishment. In some embodiments, the user GPS location of the CPU device 4980 may improve the speed or feature display to pre-update ranked menu offerings 4983 based on node ranking from the food and beverage contribution to biomarker contribution to a target. In some embodiments, the food and beverage contribution may be the food and beverage contribution to the biomarker change or optimized by the ratio of the biomarker contribution value over the variance of the biomarker contribution value considering the foodie allocation line and minimum variance frontier of the food and beverage contribution to the biomarker.

Figure 50:
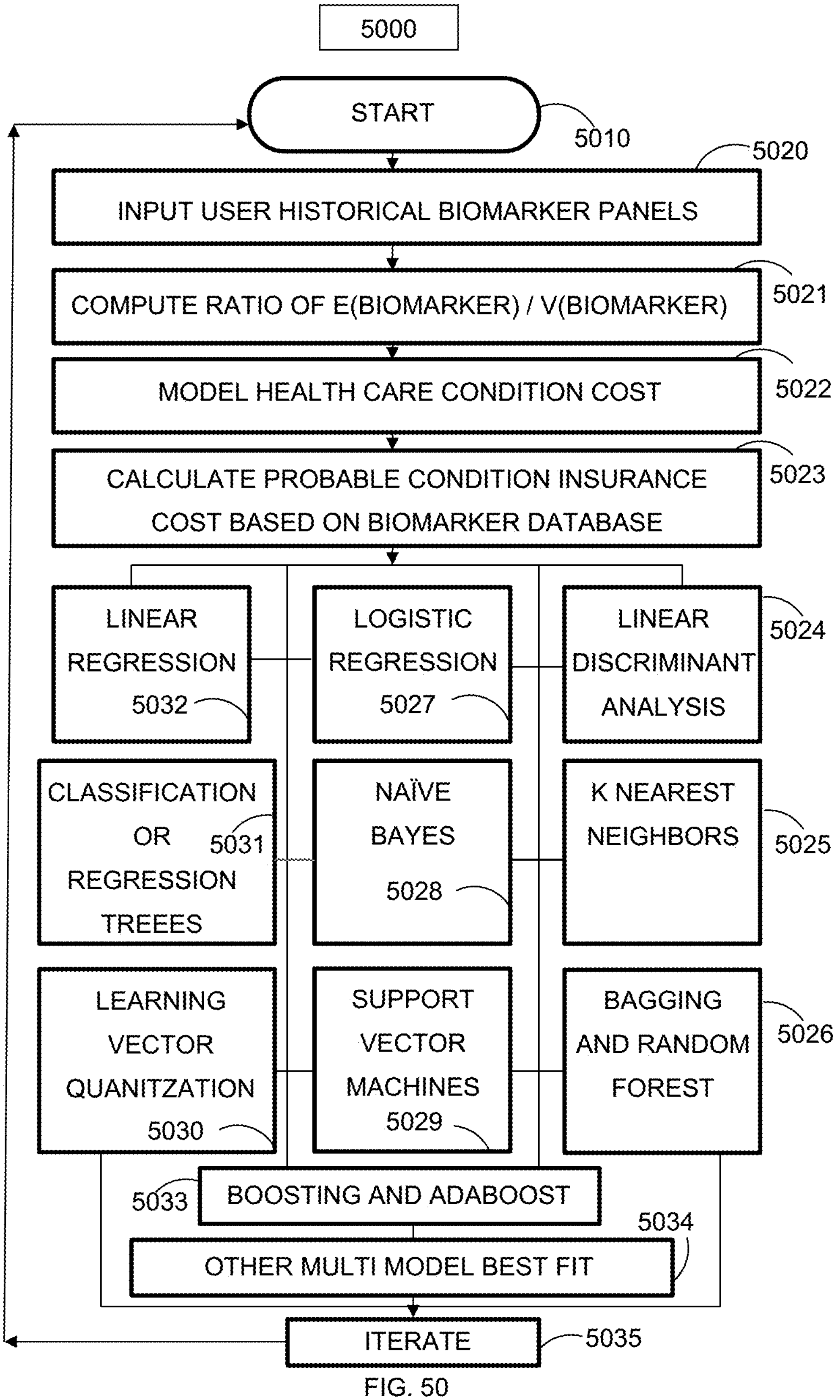
FIG. 50 illustrates an exemplary embodiment of the logic step sequence of exemplary machine learning models which may best fit biomarker panels with food or beverage combinations in a node ranked database and steps to calculate insurance costs of exemplary conditions in time series or contemporaneously.

FIG. 50 illustrates an exemplary machine learning model using the biomarker time series data to price health insurance 5000. In some embodiments, the process of pricing health insurance starts 5010 with the user inputting historical biomarker panels 5020. In some embodiments, the search node ranking and scoring may be derived from the computation of the expected value of the biomarker contribution from food or beverage combinations divided by the variance of the biomarker contribution from food or beverage combinations 5021. In some embodiments, actuary tables or tables of health care cost 5022 of various health conditions may be stored as a general table in the biomarker database 220. In some embodiments, machine learning models may best fit minimizing the errors of health care costs from the table of health care costs 5022 in the biomarker database 220 compared to a time series of biomarkers 5020 and probabilities health care costs are needed for a user. In some embodiments, health care cost models may be fit against biomarker samples and panels with linear regression 5032, logistic regression 5027, linear discriminant analysis 5024, classification or regression trees 5031, naïve bayes 5028, k nearest neighbors 5025, learning vector quantitation 5030, support vector machines 5029, bagging and random forest 5026, boosting and adaboost models 5033, other best fit models may included but are not limited to ARIMA processes, Box-Jenkins, posterior density functions, natural conjugate prior, recursion, Bayesian pretest, ridge regression, independent stochastic regressors, general stochastic regression models, general non-linear hypothesis, LaGrange multiplier test, Likelihood ratio test, autoregressive processes, moving average processes, ARMA processes, GLS, EGLS, NLS, ML estimation, AR(1), AR(2), Wald test, Durbin-Watson test, King's locally optimal bounds, Geary's sign change test, MA(1), Monte Carlo, finite distributed lags, almon distributed lag, polynomial spline distributed lag, Shiller's distributed lag, Harmonic Lag, gamma distributed lag, exponential lag, heteroscedastic specifications, Breusch-Pagan Test, Barlett Test, Godfeld Quandt test, Szroeters Class of tests, Whites Test, nonparametric tests, vector ARMA processes, ARMAX models, vector autoregressive processes, path analysis, binary choice models, multinomial logit, multinomial probit, truncated samples, two stage models, Amemiya's principle model, simultaneous equation model, piecewise regression, seasonality models, Akaike information Criterion, Jeffrey-Bayes Posterior odds ratio, conditional mean, Stein-Rule formulation model, Cox test model, J test model, quasi-Newton method model, Gauss method model, gradient method model, Marquardt's method model, Gauss-Seidel model, Grid Search, reparameterization model, penalty function model, augmented Lagrangian method model, Kalman Filter model or other models 5034. In some embodiments, the overall insurance pricing process may be iterated 5035 over many times and time period combinations. In some embodiments, probabilities of health conditions may be updated given user interaction with the plurality of interfaces of the food and beverage node rankings, searching, scoring and consumption patterns. In some embodiments, by example, but not limiting by example, annual health care costs of a type II diabetes user may be $14,000 USD each year as a cost to the employer. In some embodiments, the user may submit biomarker data to the method and system and use the node ranking system for selecting food and beverage choices. In some embodiments, the type II diabetes condition may be reversed eliminating the $14,000 annual health cost of the condition. In some embodiments the reward shema 4800 may pay the user $4,000 as a reward from an employer for reversing the type II diabetes condition through verified test results 4840 over a period of time. In some embodiments, machine learning models may calculate the reduced medical costs of the user and provide outputs which price insurance based on biomarker patterns from the method and system considering but not limited to the following models of linear regression 5032, logistic regression 5027, linear discriminant analysis 5024, classification or regression trees 5031, naïve bayes 5028, k nearest neighbors 5025, learning vector quantitation 5030, support vector machines 5029, bagging and random forest 5026, boosting and adaboost models 5033, other best fit models may included but are not limited to ARIMA processes, Box-Jenkins, posterior density functions, natural conjugate prior, recursion, Bayesian pretest, ridge regression, independent stochastic regressors, general stochastic regression models, general non-linear hypothesis, LaGrange multiplier test, Likelihood ratio test, autoregressive processes, moving average processes, ARMA processes, GLS, EGLS, NLS, ML estimation, AR(1), AR(2), Wald test, Durbin-Watson test, King's locally optimal bounds, Geary's sign change test, MA(1), Monte Carlo, finite distributed lags, almon distributed lag, polynomial spline distributed lag, Shiller's distributed lag, Harmonic Lag, gamma distributed lag, exponential lag, heteroscedastic specifications, Breusch-Pagan Test, Barlett Test, Godfeld Quandt test, Szroeters Class of tests, Whites Test, nonparametric tests, vector ARMA processes, ARMAX models, vector autoregressive processes, path analysis, binary choice models, multinomial logit, multinomial probit, truncated samples, two stage models, Amemiya's principle model, simultaneous equation model, piecewise regression, seasonality models, Akaike information Criterion, Jeffrey-Bayes Posterior odds ratio, conditional mean, Stein-Rule formulation model, Cox test model, J test model, quasi-Newton method model, Gauss method model, gradient method model, Marquardt's method model, Gauss-Seidel model, Grid Search, reparameterization model, penalty function model, augmented Lagrangian method model, Kalman Filter model or other models 5034.

The aforementioned description, for purpose of explanation, has been described with reference to specific embodiments. However the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

What is claimed is:

1. A method, comprising:

acquiring biomarker data corresponding to a user, wherein the biomarker data comprises data corresponding to one or more measurement values of one or more biomarkers for the user for one or more time periods;

receiving, by one or more computing systems, nutritional data corresponding to a plurality of food ingredients;

determining, by the one or more computing systems, a plurality of food combinations based on the plurality of food ingredients, wherein a respective food combination comprises two or more food ingredients of the plurality of food ingredients;

training, by the one or more computing systems, one or more machine learning models to determine a plurality of optimized weightings for the respective food combination for the user based on the biomarker data and the nutritional data, wherein a respective optimized weighting corresponds to a serving proportion for a respective food ingredient of the respective food combination, and wherein the plurality of optimized weightings corresponds to probability weightings with iterative feedback based on at least the biomarker data;

determining, by the one or more computing systems, a plurality of optimized food combinations based on the plurality of optimized weightings, wherein the plurality of optimized food combinations is a subset of the plurality of food combinations;

generating, by the one or more computing systems, node rankings of the plurality of optimized food combinations based on a ranking function utilizing the plurality of optimized weightings; and receiving, via one or more user interfaces of a user device, a selection from the user, wherein the selection corresponds to one or more selected food combinations from the plurality of optimized food combinations.

2. The method of claim 1, wherein:

the biomarker data further comprises complete blood count data, red blood cell data, white blood cell data, platelets data, hemoglobin data, hematocrit data, mean corpuscular volume data, blood chemistry tests data, basic metabolic panel data, blood glucose data, calcium data, electrolytes data, kidneys data, blood enzyme test data, troponin data, creatine kinase data, cholesterol data, LDL cholesterol data, HDL cholesterol data, triglyceride data, lipoprotein panel data, coagulation panel data, echocardiogram data, nuclear perfusion study data, magnetic resonance imaging data, positron emission tomography data, or combinations thereof;

the nutritional data comprises fat data, sugar data, caloric data, or combinations thereof;

the biomarker data further corresponds to a plurality of biological samples obtained from the user during the one or more time periods, wherein the plurality of biological samples was obtained before and after the user consumed at least a subset of the plurality of food ingredients during the one or more time periods;

the serving proportion for the respective food ingredient comprises a serving size proportion for the respective food ingredient, a calorie count proportion for the respective food ingredient, or combinations thereof; or combinations thereof.

3. The method of claim 1, wherein acquiring the biomarker data comprises:

obtaining biological samples data corresponding to the user before and after the user consumed at least a subset of the plurality of food ingredients during the one or more time periods; and determining, by the one or more computing systems, the biomarker data based on the biological samples data.

4. The method of claim 1, wherein receiving, via the one or more user interfaces of the user device, the selection from the user comprises receiving, by the one or more computing systems, selection data from the user device.

5. The method of claim 1, wherein receiving, via the one or more user interfaces of the user device, the selection from the user comprises:

generating a database search engine based on the plurality of optimized food combinations;

providing a search interface for the database search engine to the user device, wherein the search interface is configured to be displayed by the user device;

receiving search query input data from the user, wherein the search query input data corresponds to the plurality of food ingredients;

generating search results data based on the search query input data, the biomarker data, the nutritional data, and the one or more machine learning models, wherein the search results input data corresponds to at least a subset of the plurality of optimized food combinations;

providing a results interface to the user device based on the search results data, wherein the results interface includes at least the subset of the plurality of optimized food combinations ordered based on the node rankings, and wherein the results interface is configured to be displayed by the user device; and receiving the selection from the user via the results interface of the user device.

6. The method of claim 5, wherein generating the search results data comprises:

determining location data corresponding to the user device using one or more satellite navigation systems, wherein the location data corresponds to a geographic location of the user device; and generating the search results data based on the location data, the search query input data, the biomarker data, the nutritional data, and the one or more machine learning models.

7. The method of claim 1, wherein:

the one or more machine learning models are configured to use linear and non-linear optimization systems, wherein the linear and non-linear optimization systems comprise one or more vector maximization and minimization equations;

the one or more machine learning models comprise one or more neural networks, one or more linear regression models, one or more logistic regression models, one or more linear discriminant analysis models, one or more classification or regression tree models, one or more naïve Bayes models, one or more learning vector quantization models, one or more posterior density function models, one or more independent stochastic regressor models, one or more general stochastic regression models, one or more general non-linear hypothesis models, or combinations thereof; or combinations thereof.

8. The method of claim 1, wherein:

the plurality of optimized food combinations comprises a subset of the plurality of food ingredients; and training, by the one or more computing systems, the one or more machine learning models to determine the plurality of optimized weightings for the respective food combination for the user comprises:

mapping, from one or more databases, linear and non-linear systems of the biomarker data to generate a first matrix;

mapping, from the one or more databases, linear and non-linear systems of the nutritional data to generate a second matrix; and performing one or more matrix multiplications of at least the first and the second matrices to generate a first optimized weighting of the plurality of optimized weightings, wherein the first optimized weighting corresponds to one or more food ingredients of the plurality of food ingredients.

9. The method of claim 1, further comprising determining, by the one or more computing systems, one or more health care costs based on the biomarker data, the selection, and the one or more machine learning models.

10. The method of claim 1, wherein training, by the one or more computing systems, the one or more machine learning models to determine the plurality of optimized weightings for the respective food combination for the user comprises:

determining a plurality of return values of the plurality of food ingredients for the user based on the biomarker data, wherein a respective return value of the respective food ingredient corresponds to an increase or a decrease of the one or more measurement levels towards one or more target values after the respective food ingredient has been consumed by the user;

determining a plurality of expected return values of the plurality of food ingredients for the user based on the plurality of return values; and determining a plurality of standard deviation values of the plurality of food ingredients for the user based on the plurality of return values and the plurality of expected return values.

11. The method of claim 10, wherein training, by the one or more computing systems, the one or more machine learning models to determine the plurality of optimized weightings for the respective food combination for the user further comprises:

determining a plurality of candidate weight value sets for the respective food combination;

determining a plurality of combined expected return values for the respective food combination for the user based on the plurality of candidate weight value sets and the plurality of expected return values;

determining a plurality of covariance values for the plurality of food combinations based on the plurality of return values and the plurality of expected return values, wherein a respective covariance value corresponds to the respective food combination;

determining a plurality of combined standard deviation values for the respective food combination based on the plurality of candidate weight value sets, the plurality of standard deviation values of the plurality of food ingredients, and the respective covariance value; and determining the plurality of optimized weightings for the respective food combination based on the plurality of combined expected return values, the plurality of combined standard deviation values, and the respective covariance value.

12. The method of claim 11, wherein determining the plurality of optimized weightings for the respective food combination based on the plurality of combined expected return values, the plurality of combined standard deviation values, and the respective covariance value comprises:

determining a plurality of ratio values for the respective food combination, wherein a respective ratio value corresponds to a ratio of a respective combined expected return value to a respective combined standard deviation value for a respective candidate weight value set;

determining a maximum ratio value of the plurality of ratio values; and determining the plurality of optimized weightings for the respective food combination based on the maximum ratio value, the plurality of expected return values, the plurality of standard deviation values of the plurality of food ingredients, and the respective covariance value.

13. The method of claim 12, wherein generating, by the one or more computing systems, the node rankings of the plurality of optimized food combinations comprises:

generating the node rankings based on respective ratio values for the plurality of optimized food combinations.

14. A computing system, comprising:

one or more processors; and at least one memory, comprising program instructions which, when executed by the one or more processors, cause the one or more processors to:

acquire biomarker data corresponding to a user, wherein the biomarker data comprises data corresponding to one or more measurement values of one or more biomarkers for the user for one or more time periods;

receive nutritional data corresponding to a plurality of food ingredients;

determine a plurality of food combinations based on the plurality of food ingredients, wherein a respective food combination comprises two or more food ingredients of the plurality of food ingredients;

generate one or more machine learning models to determine a plurality of optimized weightings for the respective food combination for the user based on the biomarker data and the nutritional data, wherein a respective optimized weighting corresponds to a serving proportion for a respective food ingredient of the respective food combination, and wherein the plurality of optimized weightings corresponds to probability weightings with iterative feedback based on at least the biomarker data;

determine a plurality of optimized food combinations based on the plurality of optimized weightings, wherein the plurality of optimized food combinations is a subset of the plurality of food combinations;

generate node rankings of the plurality of optimized food combinations based on a ranking function utilizing the plurality of optimized weightings; and receive, via one or more user interfaces of a user device, a selection from the user, wherein the selection corresponds to one or more selected food combinations from the plurality of optimized food combinations.

15. The computing system of claim 14, wherein the biomarker data further corresponds to a plurality of biological samples obtained from the user during the one or more time periods, wherein the plurality of biological samples were obtained before and after the user consumed at least a subset of the plurality of food ingredients during the one or more time periods.

16. The computing system of claim 14, wherein the program instructions which, when executed by the one or more processors, cause the one or more processors to receive, via the one or more user interfaces of the user device, the selection from the user further cause the one or more processors to:

generate a database search engine based on the plurality of optimized food combinations;

provide a search interface for the database search engine to the user device, wherein the search interface is configured to be displayed by the user device;

receive search query input data from the user, wherein the search query input data corresponds to the plurality of food ingredients;

generate search results data based on the search query input data, the biomarker data, the nutritional data, and the one or more machine learning models, wherein the search results input data corresponds to at least a subset of the plurality of optimized food combinations;

provide a results interface to the user device based on the search results data, wherein the results interface includes at least the subset of the plurality of optimized food combinations ordered based on the node rankings, and wherein the results interface is configured to be displayed by the user device; and receive the selection from the user via the results interface of the user device.

17. The computing system of claim 14, wherein:

the one or more machine learning models are configured to use linear and non-linear optimization systems, wherein the linear and non-linear optimization systems comprise one or more vector maximization and minimization equations;

the one or more machine learning models comprise one or more neural networks, one or more linear regression models, one or more logistic regression models, one or more linear discriminant analysis models, one or more classification or regression tree models, one or more naïve Bayes models, one or more learning vector quantization models, one or more posterior density function models, one or more independent stochastic regressor models, one or more general stochastic regression models, one or more general non-linear hypothesis models, or combinations thereof; or combinations thereof.

18. A non-transitory computer-readable medium having stored thereon a plurality of computer-executable instructions which, when executed by a computer, cause the computer to:

acquire biomarker data corresponding to a user, wherein the biomarker data comprises data corresponding to one or more measurement values of one or more biomarkers for the user for one or more time periods;

receive nutritional data corresponding to a plurality of food ingredients;

determine a plurality of food combinations based on the plurality of food ingredients, wherein a respective food combination comprises two or more food ingredients of the plurality of food ingredients;

train one or more machine learning models to determine a plurality of optimized weightings for the respective food combination for the user based on the biomarker data and the nutritional data, wherein a respective optimized weighting corresponds to a serving proportion for a respective food ingredient of the respective food combination, and wherein the plurality of optimized weightings corresponds to probability weightings with iterative feedback based on at least the biomarker data;

determine a plurality of optimized food combinations based on the plurality of optimized weightings, wherein the plurality of optimized food combinations is a subset of the plurality of food combinations;

generate node rankings of the plurality of optimized food combinations based on a ranking function utilizing the plurality of optimized weightings; and receive, via one or more user interfaces of a user device, a selection from the user, wherein the selection corresponds to one or more selected food combinations from the plurality of optimized food combinations.

19. The non-transitory computer-readable medium of claim 18, wherein the plurality of computer-executable instructions which, when executed by the computer, cause the computer to receive, via the one or more user interfaces of the user device, the selection from the user further cause the computer to:

generate a database search engine based on the plurality of optimized food combinations;

provide a search interface for the database search engine to the user device, wherein the search interface is configured to be displayed by the user device;

receive search query input data from the user, wherein the search query input data corresponds to the plurality of food ingredients;

generate search results data based on the search query input data, the biomarker data, the nutritional data, and the one or more machine learning models, wherein the search results input data corresponds to at least a subset of the plurality of optimized food combinations;

provide a results interface to the user device based on the search results data, wherein the results interface includes at least the subset of the plurality of optimized food combinations ordered based on the node rankings, and wherein the results interface is configured to be displayed by the user device; and receive the selection from the user via the results interface of the user device.

20. The non-transitory computer-readable medium of claim 18, wherein:

the one or more machine learning models are configured to use linear and non-linear optimization systems, wherein the linear and non-linear optimization systems comprise one or more vector maximization and minimization equations;

the one or more machine learning models comprise one or more neural networks, one or more linear regression models, one or more logistic regression models, one or more linear discriminant analysis models, one or more classification or regression tree models, one or more naïve Bayes models, one or more learning vector quantization models, one or more posterior density function models, one or more independent stochastic regressor models, one or more general stochastic regression models, one or more general non-linear hypothesis models, or combinations thereof; or combinations thereof.

* * * * *